United States Patent
Wang et al.

(10) Patent No.: US 12,139,509 B2
(45) Date of Patent: Nov. 12, 2024

(54) Fc GLYCAN REMODELING PLATFORM METHOD FOR SITE-SPECIFIC ANTIBODY CONJUGATION AND APPLICATIONS THEREOF

(71) Applicant: University of Maryland, College Park, MD (US)

(72) Inventors: Lai-Xi Wang, Ellicott City, MD (US); Xiao Zhang, Xuzhou (CN)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 1 day.

(21) Appl. No.: 18/163,496

(22) Filed: Feb. 2, 2023

(65) Prior Publication Data

US 2023/0340016 A1 Oct. 26, 2023

Related U.S. Application Data

(63) Continuation of application No. PCT/US2022/026213, filed on Apr. 25, 2022.

(60) Provisional application No. 63/178,719, filed on Apr. 23, 2021, provisional application No. 63/264,012, filed on Nov. 12, 2021, provisional application No. 63/264,013, filed on Nov. 12, 2021.

(51) Int. Cl.
| | | |
|---|---|---|
| *C07K 16/00* | (2006.01) | |
| *A61K 47/54* | (2017.01) | |
| *A61K 47/68* | (2017.01) | |
| *C07K 1/12* | (2006.01) | |
| *C12N 9/10* | (2006.01) | |
| *C12N 9/24* | (2006.01) | |

(52) U.S. Cl.
CPC ............ *C07K 1/12* (2013.01); *C07K 16/00* (2013.01); *C12N 9/2402* (2013.01); *C12Y 302/01096* (2013.01); *C07K 2317/41* (2013.01)

(58) Field of Classification Search
CPC ........ C12N 9/2402; C07K 1/12; A61K 47/68; A61K 47/54; A61P 35/00; C12Y 302/01096
See application file for complete search history.

(56) References Cited

U.S. PATENT DOCUMENTS

| | | |
|---|---|---|
| 5,635,603 A | 6/1997 | Hansen et al. |
| 2008/0138855 A1 | 6/2008 | Wang |
| 2019/0002542 A1 | 1/2019 | Wang et al. |
| 2020/0022942 A1 | 1/2020 | Hu et al. |
| 2020/0062861 A1 | 2/2020 | Yu et al. |
| 2022/0008549 A1* | 1/2022 | Tsuda ...................... A61P 43/00 |
| 2023/0218766 A1 | 7/2023 | Goto et al. |

FOREIGN PATENT DOCUMENTS

WO 2022174834 A1 8/2022

OTHER PUBLICATIONS

Freise, Amanda C., et al., "In vivo imaging with antibodies and engineered fragments," Molecular immunology, Oct. 2015, pp. 142-152, 67.2.
Zhou, Qun, "Site-specific antibody conjugation for ADC and beyond," Biomedicines, Nov. 2017, 64, 5.4.
Walsh, Stephen J., et al., "Site-selective modification strategies in antibody-drug conjugates," Chemical Society Reviews, Jan. 2021, pp. 1305-1353, 50.2.
Do Pazo, Carolina, et al., "The oncology market for antibody-drug conjugates," Nat Rev Drug Discov, Aug. 2021, pp. 583-584, 20.8.
Anami, Yasuaki, et al. "Glutamic acid-valine-citrulline linkers ensure stability and efficacy of antibody-drug conjugates in mice," Nature communications, Jun. 2018, p. 2512, 9.1.
Anami, Yasuaki, et al., "Enzymatic conjugation using branched linkers for constructing homogeneous antibody-drug conjugates with high potency," Organic & biomolecular chemistry, Jul. 2017, pp. 5635-5642, 15.26.
Gray, Melissa A., et al., "Targeted glycan degradation potentiates the anticancer immune response in vivo," Nature chemical biology, Dec. 2020, pp. 1376-1384, 16.12.
Xiao, Han, et al., "Precision glycocalyx editing as a strategy for cancer immunotherapy," Proceedings of the National Academy of Sciences, Sep. 2016, pp. 10304-10309, 113.37.
Wang, Xianwu, et al., "Equipping natural killer cells with cetuximab through metabolic glycoengineering and bioorthogonal reaction for targeted treatment of KRAS mutant colorectal cancer," ACS Chemical Biology, Apr. 2021, pp. 724-730, 16.4.
Li, Jie, et al., "A single-step chemoenzymatic reaction for the construction of antibody-cell conjugates," ACS Central Science, Dec. 2018, pp. 1633-1641, 4.12.
Lehar, Sophie M., et al., "Novel antibody-antibiotic conjugate eliminates intracellular *S. aureus*," Nature, Nov. 2015, pp. 323-328, 527.7578.

(Continued)

*Primary Examiner* — Maryam Monshipouri
(74) *Attorney, Agent, or Firm* — Carter, DeLuca & Farrell LLP; George Likourezos

(57) ABSTRACT

The present disclosure provides a one-pot chemoenzymatic method for site-specific modification and conjugation of antibodies at their Fc glycan site to produce structurally well-defined antibody conjugates carrying defined drugs and other entities. The method is enabled by the discovery that certain endoglycosidases have the ability to both deglycosylate an antibody and to recognize selectively modified small disaccharide oxazolines for transglycosylation on antibodies without hydrolysis of the resulting products.

10 Claims, 52 Drawing Sheets

Specification includes a Sequence Listing.

(56) References Cited

OTHER PUBLICATIONS

Ahn, Green, et al., "LYTACs that engage the asialoglycoprotein receptor for targeted protein degradation," Nature chemical biology, Sep. 2021, pp. 937-946, 17.9.

Zhou, Yaxian, et al., "Development of triantennary N-acetylgalactosamine conjugates as degraders for extracellular proteins," ACS Central Science, Mar. 2021, pp. 499-506, 7.3.

Powell, Matthew, et al., "Targeted protein degradation: the new frontier of antimicrobial discovery?," ACS Infectious Diseases, Jul. 2021, pp. 2050-2067, 7.8.

Zhang, Xiao, et al., "Chemoenzymatic glycan-selective remodeling of a therapeutic lysosomal enzyme with high-affinity M6P-glycan ligands. Enzyme substrate specificity is the name of the game," Chemical Science, Oct. 2021, pp. 12451-12462, 12.37.

Tong, Xin, et al., "One-pot enzymatic glycan remodeling of a therapeutic monoclonal antibody by endoglycosidase S (Endo-S) from *Streptococcus pyogenes*," Bioorganic & medicinal chemistry, Apr. 2018, pp. 1347-1355, 26.7.

Yamaguchi, Takahiro, et al., "Chemoenzymatic synthesis and receptor binding of mannose-6-phosphate (M6P)-containing glycoprotein ligands reveal unusual structural requirements for M6P receptor recognition," Journal of the American Chemical Society, Sep. 2016, pp. 12472-12485, 138.38.

Qian, Jun, et al., "Structural characterization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion," Analytical biochemistry, May 2007, pp. 8-18, 364.1.

Boeggeman et al. "Site specific conjugation of fluoroprobes to the remodeled Fc N-glycans of monoclonal antibodies using mutant glycosyltransferases: Application for cell surface antigen detection" Bioconjug Chem 2009, 20(6), 1228-1236.

Zeng, Ying, et al., "Glycopeptide synthesis through endo-glycosidase-catalyzed oligosaccharide transfer of sugar oxazolines: probing substrate structural requirement," Chemistry—A European Journal, Apr. 2006, pp. 3355-3364, 12.12.

Ochiai, Hirofumi, et al., "Expeditious chemoenzymatic synthesis of homogeneous N-glycoproteins carrying defined oligosaccharide ligands," Journal of the American Chemical Society, Oct. 2008, pp. 13790-13803, 130.41.

Niemietz, Mathaus, et al., "Selective oxidative debenzylation of mono-and oligosaccharides in the presence of azides," Chemical Communications, Jul. 2011, pp. 10485-10487, 47.37.

Noguchi, Masato, et al., "Efficient synthesis of sugar oxazolines from unprotected N-acetyl-2-amino sugars by using chloroformamidinium reagent in water," The Journal of organic chemistry, Mar. 2009, pp. 2210-2212, 74.5.

Adinolfi, Matteo, et al., "Facile cleavage of carbohydrate benzyl ethers and benzylidene acetals using the NaBrO3Na2S2O4 reagent under two-phase conditions," Tetrahedron letters, Nov. 1999, pp. 8439-8441, 40.48.

Nyffeler, Paul T., et al., "The chemistry of amine-azide interconversion: Catalytic diazotransfer and regioselective azide reduction," Journal of the American Chemical Society, Sep. 2002, pp. 10773-10778, 124.36.

Lyon, Robert P., et al., "Reducing hydrophobicity of homogeneous antibody-drug conjugates improves pharmacokinetics and therapeutic index," Nature biotechnology, Jul. 2015, pp. 733-735, 33.7.

Bardia, Aditya, et al., "Sacituzumab govitecan-hziy in refractory metastatic triple-negative breast cancer," New England Journal of Medicine, Feb. 2019, pp. 741-751, 380.8.

Viricel, Warren, et al. "Monodisperse polysarcosine-based highly-loaded antibody-drug conjugates," Chemical Science, Mar. 2019, 4048-4053, 10.14.

Linclau, Bruno, et al., "Stereoarrays with an All-Carbon Quaternary Center: Diastereoselective Desymmetrization of Prochiral Malonaldehydes," Angewandte Chemie, Jan. 2012, pp. 1232-1235, 51.5.

Tanaka, Kentaro, et al. "A close-packed, highly insulating organic thin monolayer on Si (111)," Chemistry letters, Apr. 2008, pp. 440-441, 37.4.

Huang, Wei, et al., "Chemoenzymatic glycoengineering of intact IgG antibodies for gain of functions," Journal of the American Chemical Society, Jul. 2012, pp. 12308-12318, 134.29.

Collin, Mattias, et al., "EndoS, a novel secreted protein from *Streptococcus pyogenes* with endoglycosidase activity on human IgG," The EMBO journal, Jun. 2001, pp. 3046-3055, 20.12.

Sjogren, Jonathan, et al., "EndoS2 is a unique and conserved enzyme of serotype M49 group A *Streptococcus* that hydrolyses N-linked glycans on IgG and a1-acid glycoprotein," Biochemical journal, Oct. 2013, pp. 107-118, 455.1.

Giddens, John P., et al., "Site-selective chemoenzymatic glycoengineering of Fab and Fc glycans of a therapeutic antibody," Proceedings of the National Academy of Sciences, Nov. 2018, pp. 12023-12027, 115.47.

Li, Tiezheng, et al. "Site-specific immobilization of endoglycosidases for streamlined chemoenzymatic glycan remodeling of antibodies," Carbohydrate research, Mar. 2018, pp. 77-84, 458.

Wakankar, Aditya A., et al., "Physicochemical stability of the antibody-drug conjugate trastuzumab-DM1: changes due to modification and conjugation processes," Bioconjugate chemistry, Sep. 2010, pp. 1588-1595, 21.9.

Doronina, Svetlana O., et al., "Development of potent monoclonal antibody auristatin conjugates for cancer therapy," Nat Biotechnol, Jun. 2003, pp. 778-784, 21.

Sianturi, Julinton, et al., "Development of a-Gal-Antibody Conjugates to Increase Immune Response by Recruiting Natural Antibodies," Angewandte Chemie, Mar. 2019, pp. 4526-4530, 58.

Hopkins, Andrew L., et al., "The druggable genome," Nature reviews Drug discovery, Sep. 2002, pp. 727-730, 1.9.

Crews, Craig M., "Targeting the undruggable proteome: the small molecules of my dreams," Chemistry & biology, Jun. 2010, pp. 551-555, 17.6.

Bond, Michael J., et al., "Proteolysis targeting chimeras (PROTACs) come of age: entering the third decade of targeted protein degradation," RSC chemical biology, Mar. 2021, pp. 725-742, 2.3.

Spradlin, Jessica N., et al., "Reimagining druggability using chemoproteomic platforms," Accounts of Chemical Research, Mar. 2021, pp. 1801-1813, 54.7.

Lu, Jing, et al., "Hijacking the E3 ubiquitin ligase cereblon to efficiently target BRD4," Chemistry & biology, Jun. 2015, pp. 755-763, 22.6.

Schapira, Matthieu, et al., "Targeted protein degradation: expanding the toolbox," Nature reviews Drug discovery, Dec. 2019, pp. 949-963, 18.12.

Zou, Yutian, et al., "The PROTAC technology in drug development," Cell biochemistry and function, Jan. 2019, pp. 21-30, 37.1.

Cotton, Adam D., et al., "Development of antibody-based PROTACs for the degradation of the cell-surface immune checkpoint protein PD-L1," Journal of the American Chemical Society, Jan. 2021, pp. 593-598, 143.2.

Montrose, Kristopher, et al., "Design of a PROTAC that antagonizes and destroys the cancer-forming X-protein of the hepatitis B virus," Biochemical and Biophysical Research Communications, Oct. 2014, pp. 735-740, 453.4.

Kolb, Ryan, et al., "Proteolysis-targeting chimera against BCL-XL destroys tumor-infiltrating regulatory T cells," Nature communications, Feb. 2021, 9 pages, 12.1.

Tomoshige, Shusuke, et al., "PROTACs and other chemical protein degradation technologies for the treatment of neurodegenerative disorders," Angewandte Chemie International Edition, Feb. 2021, pp. 3346-3354, 60.7.

Cromm, Phillipp M., et al., "Targeted protein degradation: from chemical biology to drug discovery," Cell chemical biology, Sep. 2017, pp. 1181-1190, 24.9.

Lamb, Christopher A., et al., "Endocytosis and autophagy: Shared machinery for degradation," Bioessays, Jan. 2013, pp. 34-45, 35.1.

Banik, Steven M., et al., "Lysosome-targeting chimaeras for degradation of extracellular proteins," Nature, Aug. 2020, pp. 291-297, 584.7820.

(56) References Cited

OTHER PUBLICATIONS

Li, Tiezheng, et al. "Glycosynthase mutants of endoglycosidase S2 show potent transglycosylation activity and remarkably relaxed substrate specificity for antibody glycosylation remodeling," Journal of Biological Chemistry, Aug. 2016, pp. 16508-16518, 291.32.

Giddens, John P., et al., "Endo-F3 glycosynthase mutants enable chemoenzymatic synthesis of core-fucosylated triantennary complex type glycopeptides and glycoproteins," Journal of Biological Chemistry, Apr. 2016, pp. 9356-9370, 291.17.

Chung, Christine H., et al., "Cetuximab-induced anaphylaxis and IgE specific for galactose-a-1, 3-galactose," New England journal of medicine, Mar. 2008, pp. 1109-1117, 358.11.

Chevreux, Guillaume, et al., "Fast analysis of recombinant monoclonal antibodies using IdeS proteolytic digestion and electrospray mass spectrometry," Analytical biochemistry, Aug. 2011, pp. 212-214, 415.2.

Zhang, Xiao, et al., "General and Robust Chemoenzymatic Method for Glycan-Mediated Site-Specific Labeling and Conjugation of Antibodies: Facile Synthesis of Homogeneous Antibody-Drug Conjugates," ACS chemical biology, Sep. 2021, pp. 2502-2514, 16.11.

Wang, Zhen, et al., "A general strategy for the chemoenzymatic synthesis of asymmetrically branched N-glycans," Science, Jul. 2013, pp. 379-383, 341.6144.

Lossouarn, Alexis, et al., "Maleimide-based metal-free ligation with dienes: a comparative study," Organic & Biomolecular Chemistry, May 2020, pp. 3874-3887, 18.20.

Ou, Chong, et al., "One-Pot Conversion of Free Sialoglycans to Functionalized Glycan Oxazolines and Efficient Synthesis of Homogeneous Antibody-Drug Conjugates through Site-Specific Chemoenzymatic Glycan Remodeling," Bioconjugate chemistry, Aug. 2021, pp. 1888-1897, 32.8.

Orgueira, Hernán A., et al., "Modular synthesis of heparin oligosaccharides," Chemistry—A European Journal, Jan. 2003, pp. 140-169, 9.1.

Goto, Kohtaro, et al., "Site-specific protein PEGylation catalyzed by endo-ß-N-acetylglucosaminidase," Tetrahedron Letters, Feb. 2020, p. 151475, 61.6.

Strop, Pavel, et al., "Site-specific conjugation improves therapeutic index of antibody drug conjugates with high drug loading," Nature biotechnology, Jul. 2015, pp. 694-696, 33.7.

Goodfellow, Jonathan J., et al., "An endoglycosidase with alternative glycan specificity allows broadened glycoprotein remodelling," Journal of the American Chemical Society, May 2012, pp. 8030-8033, 134.19.

Tarentino, A. L., et al., "Overexpression and purification of non-glycosylated recombinant endo-ß-N-acetylglucosaminidase F3," Glycobiology, Sep. 1995, pp. 599-601, 5.6.

Huang, Wei, et al., "Unusual transglycosylation activity of Flavobacterium meningosepticum endoglycosidases enables convergent chemoenzymatic synthesis of core fucosylated complex N-glycopeptides," ChemBioChem, Apr. 2011, pp. 932-941, 12.6.

Takegawa, Kaoru, et al., "Cloning, Sequencing, and Expression of Arthrobacter protophormiae Endo-ß-N-acetylglucosaminidase in *Escherichia coli*," Archives of biochemistry and biophysics, Feb. 1997, pp. 22-28, 338.1.

Fan, Shu-Quan, et al., "Remarkable transglycosylation activity of glycosynthase mutants of endo-ß-N-acetylglucosaminidase from *Streptococcus pneumoniae*," Journal of Biological Chemistry, Mar. 2012, pp. 11272-11281, 287.14.

Eshima, Yasunari, et al., "Transglycosylation activity of glycosynthase mutants of endo-ß-N-acetylglucosaminidase from Coprinopsis cinerea," PLoS One, Jul. 2015, e0132859, 10.7.

International Search Report and Written Opinion for related case PCT/US22/26213, Oct. 4, 2022, 20 pages.

Notification Concerning Transmittal of International Preliminary Report on Patentability for International Application No. PCT/US22/26213, Nov. 2, 2023, 1 page.

International Preliminary Report on Patentability for International Application No. PCT/US22/26213, Oct. 24, 2023, 14 pages.

\* cited by examiner

FIG. 4
Group I, Manβ1,4GlcNAc based oxazolines
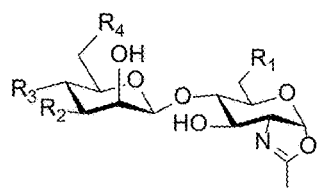
R1, R2, R3, R4 = OH, $N_3$, PEG-linked $N_3$, a fluorescent probe, a biotin moiety, a ligand, or a drug
Man: mannose; GlcNAc, N-acetylglucosamine
PEG linker: a polyethylene glycol (PEG) linker
Examples:
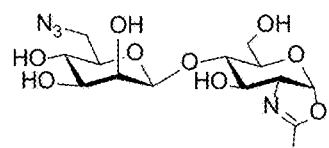 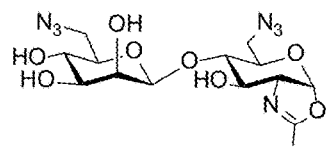 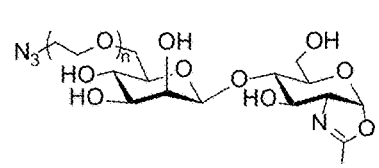
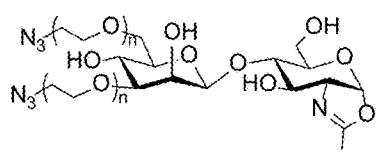 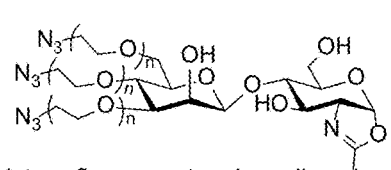 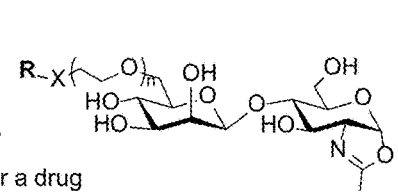
n = 0 - 20; X = linker; R = biotin moiety, a fluorescent probe, a ligand, or a drug

FIG. 5
Group II, Glcβ1,4GlcNAc based oxazolines
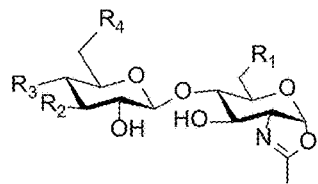
R1, R2, R3, R4 = OH, $N_3$, PEG-linked $N_3$, a fluorescent probe, a biotin moiety, a ligand, or a drug
Glc: Glucose; GlcNAc, N-acetylglucosamine
PEG linker: a polyethylene glycol (PEG) linker
Examples:
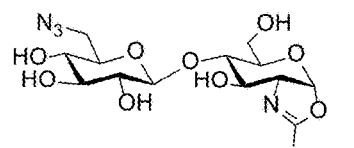
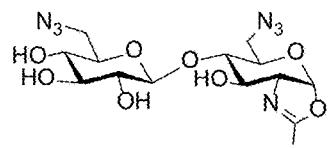
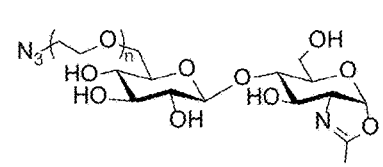
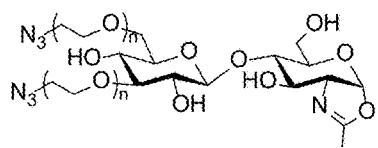
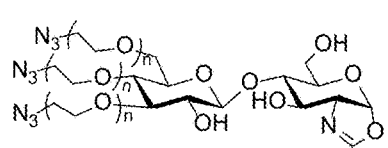
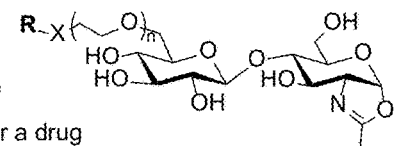
n = 0 - 20; X = linker; R = biotin moiety, a fluorescent probe, a ligand, or a drug

FIG. 6
Group III, Galβ1,4GlcNAc based oxazolines
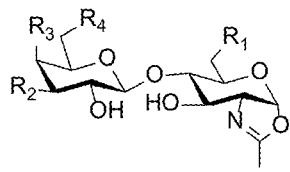
R1, R2, R3, R4 = OH, N$_3$, PEG-linked N$_3$, a fluorescent probe, a biotin moiety, a ligand, or a drug
Gal, galactose; GlcNAc, N-acetylglucosamine
PEG linker: a polyethylene glycol (PEG) linker
Examples:
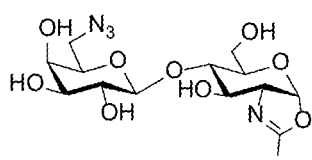 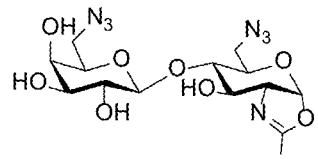 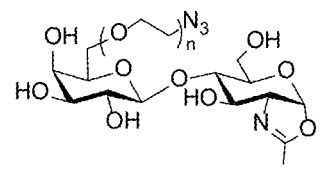
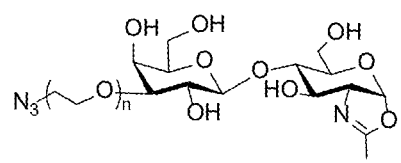 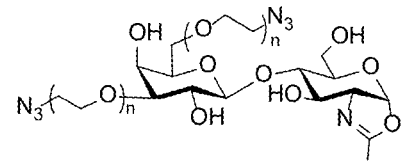
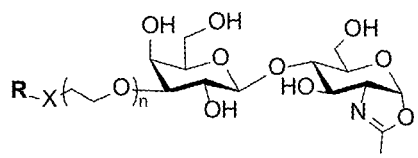 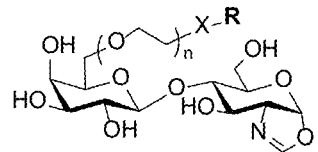
n = 0 - 20; X = linker; R = biotin moiety, a fluorescent probe, a ligand, or a drug

FIG. 25
Synthesis of Man-GlcNAc-oxazoline:
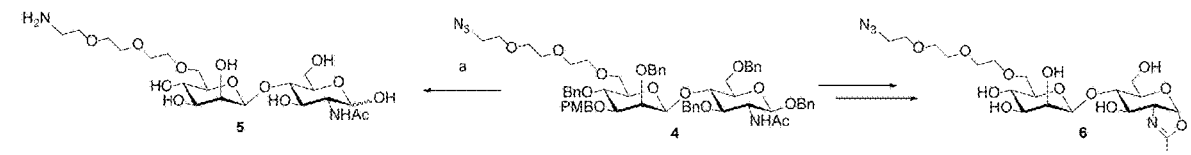
Synthesis of Glc-GlcNAc-oxazoline:
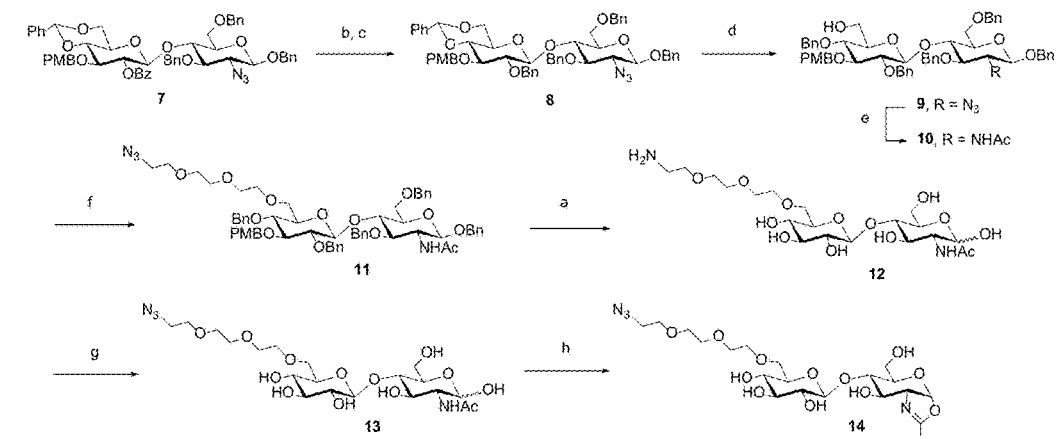
Synthesis of Gal-GlcNAc-oxazoline:
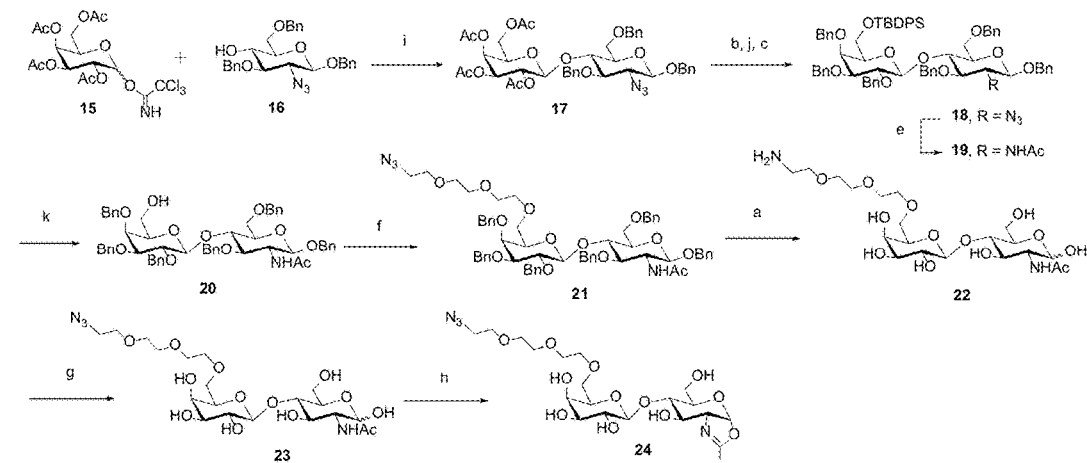

Screening of the transglycosylation conditions.

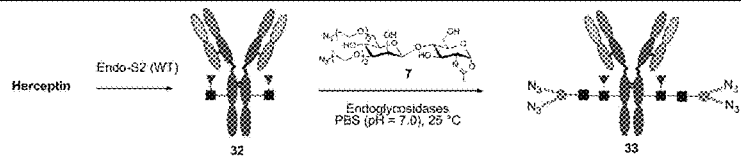

| ENGases | Transglycosylation | | | | Product hydrolysis |
|---|---|---|---|---|---|
| | oxazoline (eq)[a] | enzyme (w/w) | time | conversion yield | |
| Endo-S2 | 20 | 0.1% | 1 h | 98% | < 1%[c] |
| Endo-S2 D184M | 20 | 1% | 2 h | 70% | no |
| Endo-S | 20 + 20 | 1% | 2 h | 65% | no |
| Endo-S D233Q | 20 | 10% | 3 h | 15% | no |
| Endo-F3 | 20 | 10% | 3 h | < 5% | --[d] |
| Endo-F3 D165A | 20 | 10% | 3 h | < 5% | --[d] |
| Endo-A | 20 | 10% | 3 h | 0 (< 5%[b]) | --[d] |
| Endo-D | 20 | 10% | 3 h | 0 (10%[b]) | no |
| Endo-CC | 20 | 10% | 3 h | 0 (< 5%[b]) | --[d] |

[a] Based on each glycosylation site; [b] Non-fucosylated antibody (GlcNAc-Herceptin) was used as the acceptor as these three enzymes do not recognize Fucα1,6GlcNAc-antibody as the acceptor; [c] After 6 hours at room temperature; [d] Not determined.

FIG. 39A-D

| ADCs | 43 | 44 | 45 | 46 | 47 | 48 |
|---|---|---|---|---|---|---|
| DAR | 2 | 4 | 6 | 8 | 12 | 4 |
| $EC_{50}{}^{b}$ (ng/mL) | 25.58±6.54 | 16.05±4.64 | 12.68±5.51 | 8.79±0.42 | 7.13±0.79 | 15.69±3.26 |
| $EC_{50}{}^{b}$ (nM) | 0.170±0.044 | 0.104±0.030 | 0.080±0.035 | 0.054±0.003 | 0.042±0.005 | 0.102±0.021 |

FIG. 42
a) Bertozzi et al, 2020
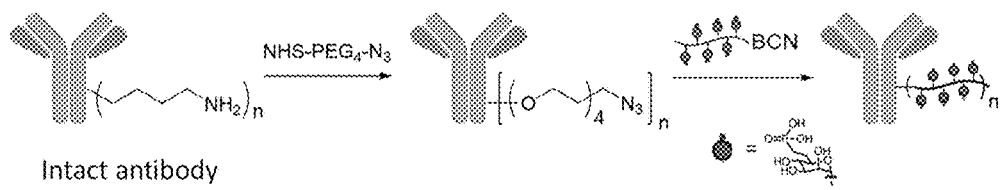
b) This work
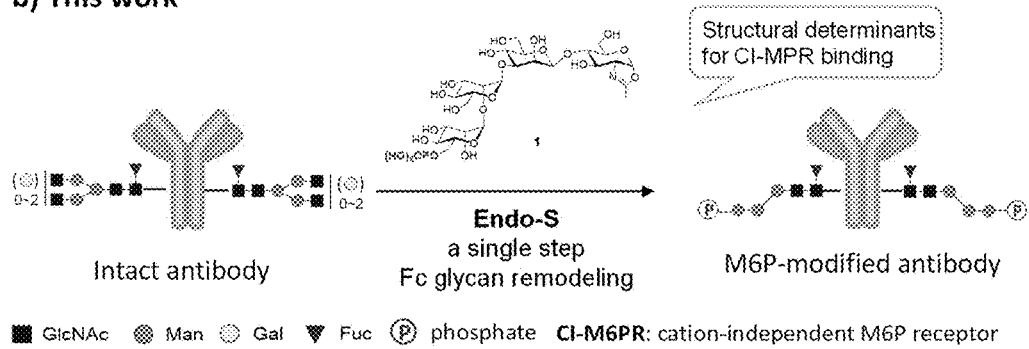
Bertozzi et al.= Banik et al. Lysosome-targeting chimaeras for degradation of extracellular proteins. July 29, 2020, Nature 584:291.

FIG. 43

Screening of the transglycosylation conditions.

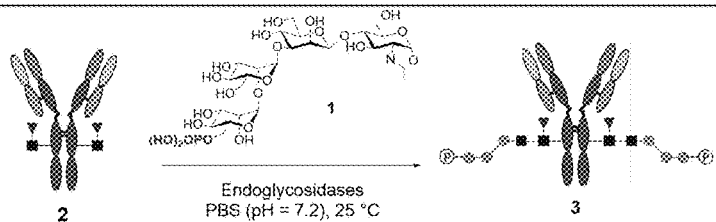

| ENGases | Transglycosylation | | | | Product hydrolysis |
|---|---|---|---|---|---|
| | oxazoline (eq)[a] | enzyme (w/w) | time | conversion yield | |
| Endo-S | 20 + 10 | 0.2% | 2 h | 98% | < 1%[d] |
| Endo-S D233Q | 20 + 20 | 2% | 2 h | 75% | no |
| Endo-S2 | 20 + 10 | 0.1% | 2 h | 70%[b] | 15%[d] |
| Endo-S2 D184M | 10 | 0.1%~0.2% | 1 h | 98% | < 1%[d] |
| Endo-F3 | 20 + 20 | 10% | 2 h | 55% | no |
| Endo-F3 D165A | 20 | 10% | 3 h | 10% | no |
| Endo-A | 20 | 10% | 3 h | < 5%[c] | --[e] |
| Endo-D | 20 | 10% | 3 h | < 5%[c] | --[e] |
| Endo-CC | 20 | 10% | 3 h | < 5%[c] | --[e] | a. based on the reaction sites; b. due to simultaneous hydrolysis of the transglycosylation product by the wild-type enzyme; c. non-fucosylated trastuzumab was used; d. after 3 hours at room temperature; e. not determined.

Scheme 1

Fig. 50
Synthesized and tested structures:
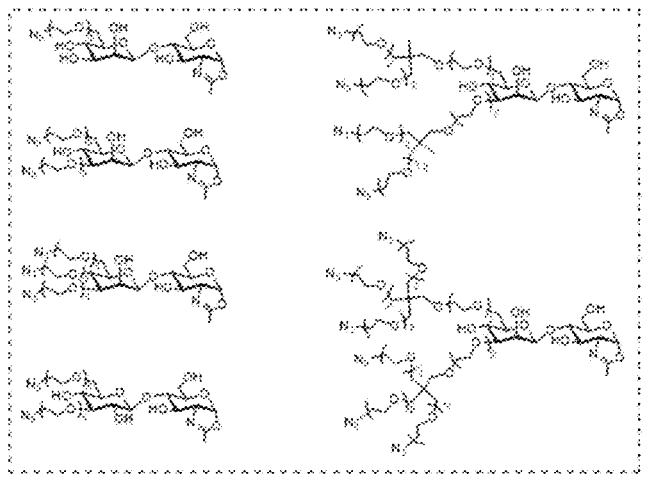
Different spacers at different positions:
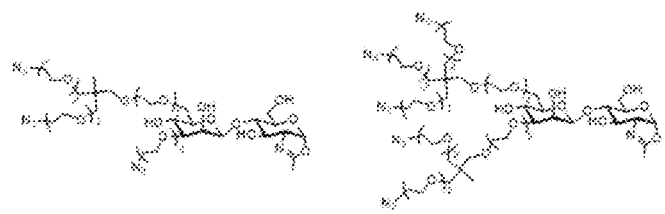
Different branched scaffolds:
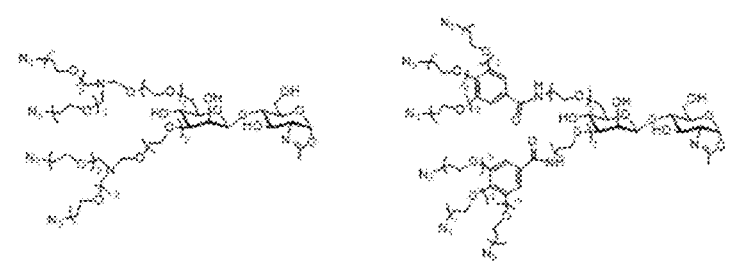
Replace core mannose with glucose:
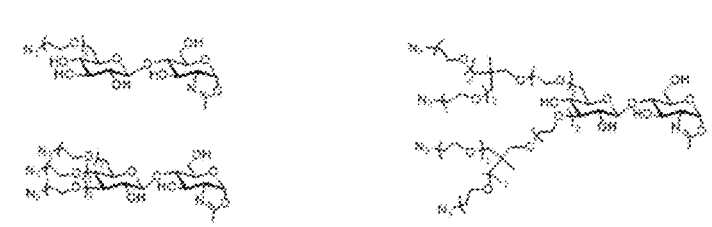
Tri- or tetrasaccharide oxazolines to introduce the functional groups:
Different numbers and positions of spacers:
Different lengths of spacers:
Different functional groups:

| ENGases | Transglycosylation | | | | Product hydrolysis |
|---|---|---|---|---|---|
| | oxazoline (eq)[a] | enzyme (w/w) | time | conversion yield | |
| Endo S | 20 + 20 | 1% | 2 h | 65% | no |
| Endo S-D233Q | 20 | 10% | 3 h | 15% | no |
| Endo S2 | 20 | 0.1%~0.2% | 1 h | 98% | marginal |
| Endo S2-D184M | 20 | 1% | 2 h | 70% | no |
| Endo F3 | 20 | 10% | 3 h | < 5% | --[c] |
| Endo A | 20 | 10% | 3 h | 0 (< 5%[b]) | --[c] |
| Endo D | 20 | 10% | 3 h | 0 (10%[b]) | no |
| Endo CC | 20 | 10% | 3 h | 0 (< 5%[b]) | --[c] | a. based on the reaction sites; b. non-fucosylated Herceptin (GN-Her) was used; c. not determined.

| ENGases | Transglycosylation | | | | Product hydrolysis |
|---|---|---|---|---|---|
| | oxazoline (eq)[a] | enzyme (w/w) | time | conversion yield | |
| Endo S | 20 + 10 | 0.2% | 2 h | 98% | marginal |
| Endo S-D233Q | 20 + 20 | 2% | 2 h | 75% | no |
| Endo S2 | 20 + 10 | 0.1% | 2 h | 70% | slow |
| Endo S2-D184M | 10 | 0.1%~0.2% | 1 h | 98% | marginal |
| Endo F3 | 20 + 20 | 10% | 2 h | 55% | no |
| Endo F3-D165A | 20 | 10% | 3 h | 10% | no |
| Endo A | 20 | 10% | 3 h | < 5%[b] | --[c] |
| Endo D | 20 | 10% | 3 h | < 5%[b] | --[c] |
| Endo CC | 20 | 10% | 3 h | < 5%[b] | --[c] | a. based on the reaction sites; b. non-fucosylated Herceptin (GN-Her) was used; c. not determined.

SEQUENCE LISTING

```
Sequence total quantity: 16
SEQ ID NO: 1              moltype = AA  length = 815
FEATURE                   Location/Qualifiers
source                    1..815
                          mol_type = protein
                          organism = Streptococcus pyogenes
SEQUENCE: 1
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
KDSYVHKLHQ QGTALVQTIG VNELNGRTGL SKDYPDTPEG NKALAAAIVK AFVTDRGVDG   180
LDIDIEHEFT NKRTPEEDAR ALNVFKEIAQ LIGKNGSDKS KLLIMDTTLS VENNPIFKGI   240
AEDLDYLLRQ YYGSQGGEAE VDTINSDWNQ YQNYIDASQF MIGFSFFEES ASKGNLWFDV   300
NEYDPNNPEK GKDIEGTRAK KYAEWQPSTG GLKAGIFSYA IDRDGVAHVP STYKNRTSTN   360
LQRHEVDNIS HTDYTVSRKL KTLMTEDKRY DVIDQKDIPD PALREQIIQQ VGQYKGDLER   420
YNKTLVLTGD KIQNLKGLEK LSKLQKLELR QLLPESMKKD AELVMVGMTG              480
LEKLNLSGLN RQTLDGIDVN SITHLTSFDI SHNSLDLSEK SEDRKLLMTL MEQVSNHQKI   540
TVKNTAFENQ KPKGYYPQTY DTKEGHYDVD NAEHDILTDF VFGTVTKRNT FIGDEEAFAI   600
YKEGAVDGRQ YVSKDYTYEA FRKDYKGYKV HLTASNLGET VTSKVTATTD ETYLVDVSDG   660
EKVVHHMKLN IGSGAIMMEN LAKGAKVIGT SGDFEQAKKI FDGEKSDRFF TWGQTNWIAF   720
DLGEINLAKE WRLFNAETNT EIKTDSSLNV AKGRLQILKD TTIDLEKMDI KNRKEYLSND   780
ENWTDVAQMD DKAIFNSKL SNVLSRYWRF CVDGG                              815

SEQ ID NO: 2              moltype = AA  length = 995
FEATURE                   Location/Qualifiers
REGION                    1..995
                          note = Description of Artificial Sequence: Synthetic
                          polypeptide
source                    1..995
                          mol_type = protein
                          organism = synthetic construct
SEQUENCE: 2
```

```
MDKHLLVKRT LGCVCAATLM GAALATHHDS LNTVKAEEKT VQVQKGLPSI DSLHYLSENS    60
KKEFKEELSK AGQESQKVKE ILAKQQADK  QAQELAKMKI PEKIPMKPLH GPLYGGYFRT   120
WHDKTSDPTE KDKVNSMGEL PKEVDLAFIF HDWTKDYSLF WKELATKHVP KLNKQGTRVI   180
RTIPWRFLAG GDNSGIAEDT SKYPNTPEGN KALAKAIVDE YVYKYNLDGL DVQVEHDSIP   240
KVDKKEDTAG VERSIQVFEE IGKLIGPKGV DKSRLFIMDS TYMADKNPLI ERGAPYINLL   300
LVQVYGSQGE KGGWEPVSNR PEKTMEERWQ GYSKYIRPEQ YMIGFSFYEE NAQEGNLWYD   360
INSRKDEDKA NGINTDITGT RAERYARWQP KTGGVKGGIF SYAIDRDGVA HQPKKYAKQK   420
EFKDATDNIF HSDYSVSKAL KTVMLKDKSY DLIDEKDFPD KALREAVMAQ VGTRKGDLER   480
FNGTLRLDNP AIQSLEGLNK FKKLAQLDLI GLSRITKLDR SVLPANMKPG KDTLETVLET   540
YKKDNKEEPA TIPPVSLKVS GLTGLKELDL SGFDRETLAG LDAATLTSLE KVDISGNKLD   600
LAPGTENRQI FDTMLSTISN HVGSNEQTVK FDKQKPTGHY PDTYGKTSLR LPVANEKVDL   660
QSQLLFGTVT NQGTLINSEA DYKAYQNHKI AGRSFVDSNY HYNNFKVSYE NYTVKVTDST   720
LGTTTDKTLA TDKEETYKVD FFSPADKTKA VHTAKVIVGD EKTMMVNLAE GATVIGGSAD   780
PVNARKVFDG QLGSETDNIS LGWDSKQSII FKLKEDGLIK HWRFFNDSAR NPETTNKPIQ   840
EASLQIFNIK DYNLDNLLEN PNKFDDEKYW ITVDTYSAQG ERATAFSNTL NNITSKYWRV   900
VFDTKGDRYS SPVVPELQIL GYPLPNADTI MKTVTTAKEL SQQKDKFSQK MLDELKIKEM   960
ALETSLNSKI FDVTAINANA GVLKDCIEKR QLLKK                              995

SEQ ID NO: 3              moltype = AA  length = 995
FEATURE                   Location/Qualifiers
REGION                    1..995
                          note = Description of Artificial Sequence: Synthetic
                           polypeptide
source                    1..995
                          mol_type = protein
                          organism = synthetic construct
SEQUENCE: 3
MDKHLLVKRT LGCVCAATLM GAALATHHDS LNTVKAEEKT VQVQKGLPSI DSLHYLSENS    60
KKEFKEELSK AGQESQKVKE ILAKQQADK  QAQELAKMKI PEKIPMKPLH GPLYGGYFRT   120
WHDKTSDPTE KDKVNSMGEL PKEVDLAFIF HDWTKDYSLF WKELATKHVP KLNKQGTRVI   180
RTIPWRFLAG GDNSGIAEDT SKYPNTPEGN KALAKAIVDE YVYKYNLDGL DVAVEHDSIP   240
KVDKKEDTAG VERSIQVFEE IGKLIGPKGV DKSRLFIMDS TYMADKNPLI ERGAPYINLL   300
LVQVYGSQGE KGGWEPVSNR PEKTMEERWQ GYSKYIRPEQ YMIGFSFYEE NAQEGNLWYD   360
INSRKDEDKA NGINTDITGT RAERYARWQP KTGGVKGGIF SYAIDRDGVA HQPKKYAKQK   420
EFKDATDNIF HSDYSVSKAL KTVMLKDKSY DLIDEKDFPD KALREAVMAQ VGTRKGDLER   480
FNGTLRLDNP AIQSLEGLNK FKKLAQLDLI GLSRITKLDR SVLPANMKPG KDTLETVLET   540
YKKDNKEEPA TIPPVSLKVS GLTGLKELDL SGFDRETLAG LDAATLTSLE KVDISGNKLD   600
LAPGTENRQI FDTMLSTISN HVGSNEQTVK FDKQKPTGHY PDTYGKTSLR LPVANEKVDL   660
QSQLLFGTVT NQGTLINSEA DYKAYQNHKI AGRSFVDSNY HYNNFKVSYE NYTVKVTDST   720
LGTTTDKTLA TDKEETYKVD FFSPADKTKA VHTAKVIVGD EKTMMVNLAE GATVIGGSAD   780
PVNARKVFDG QLGSETDNIS LGWDSKQSII FKLKEDGLIK HWRFFNDSAR NPETTNKPIQ   840
EASLQIFNIK DYNLDNLLEN PNKFDDEKYW ITVDTYSAQG ERATAFSNTL NNITSKYWRV   900
VFDTKGDRYS SPVVPELQIL GYPLPNADTI MKTVTTAKEL SQQKDKFSQK MLDELKIKEM   960
ALETSLNSKI FDVTAINANA GVLKDCIEKR QLLKK                              995

SEQ ID NO: 4              moltype = AA  length = 995
FEATURE                   Location/Qualifiers
source                    1..995
                          mol_type = protein
                          organism = Streptococcus pyogenes
SEQUENCE: 4
MDKHLLVKRT LGCVCAATLM GAALATHHDS LNTVKAEEKT VQVQKGLPSI DSLHYLSENS    60
KKEFKEELSK AGQESQKVKE ILAKQQADK  QAQELAKMKI PEKIPMKPLH GPLYGGYFRT   120
WHDKTSDPTE KDKVNSMGEL PKEVDLAFIF HDWTKDYSLF WKELATKHVP KLNKQGTRVI   180
RTIPWRFLAG GDNSGIAEDT SKYPNTPEGN KALAKAIVDE YVYKYNLDGL DVDVEHDSIP   240
KVDKKEDTAG VERSIQVFEE IGKLIGPKGV DKSRLFIMDS TYMADKNPLI ERGAPYINLL   300
LVQVYGSQGE KGGWEPVSNR PEKTMEERWQ GYSKYIRPEQ YMIGFSFYEE NAQEGNLWYD   360
INSRKDEDKA NGINTDITGT RAERYARWQP KTGGVKGGIF SYAIDRDGVA HQPKKYAKQK   420
EFKDATDNIF HSDYSVSKAL KTVMLKDKSY DLIDEKDFPD KALREAVMAQ VGTRKGDLER   480
FNGTLRLDNP AIQSLEGLNK FKKLAQLDLI GLSRITKLDR SVLPANMKPG KDTLETVLET   540
YKKDNKEEPA TIPPVSLKVS GLTGLKELDL SGFDRETLAG LDAATLTSLE KVDISGNKLD   600
LAPGTENRQI FDTMLSTISN HVGSNEQTVK FDKQKPTGHY PDTYGKTSLR LPVANEKVDL   660
QSQLLFGTVT NQGTLINSEA DYKAYQNHKI AGRSFVDSNY HYNNFKVSYE NYTVKVTDST   720
LGTTTDKTLA TDKEETYKVD FFSPADKTKA VHTAKVIVGD EKTMMVNLAE GATVIGGSAD   780
PVNARKVFDG QLGSETDNIS LGWDSKQSII FKLKEDGLIK HWRFFNDSAR NPETTNKPIQ   840
EASLQIFNIK DYNLDNLLEN PNKFDDEKYW ITVDTYSAQG ERATAFSNTL NNITSKYWRV   900
VFDTKGDRYS SPVVPELQIL GYPLPNADTI MKTVTTAKEL SQQKDKFSQK MLDELKIKEM   960
ALETSLNSKI FDVTAINANA GVLKDCIEKR QLLKK                              995

SEQ ID NO: 5              moltype = AA  length = 329
FEATURE                   Location/Qualifiers
source                    1..329
                          mol_type = protein
                          organism = Elizabethkingia meningoseptica
SEQUENCE: 5
MKKIFFAQCS ILLLMLGSCS KMTEDMTPES VNKEASVKSA TALAGSNGVC IAYYITDGRN    60
PTFKLKDIPD KVDMVILFGL KYWSLQDTTK LPGGTGMMGS FKSYKDLDTQ IRSLQSRGIK   120
VLQNIDDDVS WQSSKPGGFA SAAAYGDAIK SIVIDKWKLD GISLDIEHSG AKPNPIPTFP   180
GYAATGYNGW YSGSMAATPA FLNVISELTK YFGTTAPNNK QLQIASGIDV YAWNKIMENF   240
```

```
RNNFNYIQLQ SYGANVSRTQ LMMNYATGTN KIPASKMVFG AYAEGGTNQA NDVEVAKWTP    300
TQGAKGGMMI YTYNSNVSYA NAVRDAVKN                                    329

SEQ ID NO: 6              moltype = AA  length = 819
FEATURE                   Location/Qualifiers
REGION                    1..819
                          note = Description of Artificial Sequence: Synthetic
                           polypeptide
source                    1..819
                          mol_type = protein
                          organism = synthetic construct
SEQUENCE: 6
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
KDSYVHKLHQ QGTALVQTIG VNELNGRTGL SKDYPDTPEG NKALAAAIVK AFVTDRGVDG   180
LDIAIEHEFT NKRTPEEDAR ALNVFKEIAQ LIGKNGSDKS KLLIMDTTLS VENNPIFKGI   240
AEDLDYLLRQ YYGSQGGEAE VDTINSDWNQ YQNYIDASQF MIGFSFFEES ASKGNLWFDV   300
NEYDPNNPEK GKDIEGTRAK KYAEWQPSTG GLKAGIFSYA IDRDGVAHVP STYKNRTSTN   360
LQRHEVDNIS HTDYTVSRKL KTLMTEDKRY DVIDQKDIPD PALREQIIQQ VGQYKGDLER   420
YNKTLVLTGD KIQNLKGLEK LSKLQKLELR QLSNVKEITP ELLPESMKKD AELVMVGMTG   480
LEKLNLSGLN RQTLDGIDVN SITHLTSFDI SHNSLDLSEK SEDRKLLMTL MEQVSNHQKI   540
TVKNTAFENQ KPKGYYPQTY DTKEGHYDVD NAEHDILTDF VFGTVTKRNT FIGDEEAFAI   600
YKEGAVDGRQ YVSKDYTYEA FRKDYKGYKV HLTASNLGET VTSKVTATTD ETYLVDVSDG   660
EKVVHHMKLN IGSGAIMMEN LAKGAKVIGT SGDFEQAKKI FDGEKSDRFF TWGQTNWIAF   720
DLGEINLAKE WRLFNAETNT EIKTDSSLNV AKGRLQILKD TTIDLEKMDI KNRKEYLSND   780
ENWTDVAQMD DAKAIFNSKL SNVLSRYWRF CVDGGASSY                         819

SEQ ID NO: 7              moltype = AA  length = 819
FEATURE                   Location/Qualifiers
REGION                    1..819
                          note = Description of Artificial Sequence: Synthetic
                           polypeptide
source                    1..819
                          mol_type = protein
                          organism = synthetic construct
SEQUENCE: 7
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
KDSYVHKLHQ QGTALVQTIG VNELNGRTGL SKDYPDTPEG NKALAAAIVK AFVTDRGVDG   180
LDICIEHEFT NKRTPEEDAR ALNVFKEIAQ LIGKNGSDKS KLLIMDTTLS VENNPIFKGI   240
AEDLDYLLRQ YYGSQGGEAE VDTINSDWNQ YQNYIDASQF MIGFSFFEES ASKGNLWFDV   300
NEYDPNNPEK GKDIEGTRAK KYAEWQPSTG GLKAGIFSYA IDRDGVAHVP STYKNRTSTN   360
LQRHEVDNIS HTDYTVSRKL KTLMTEDKRY DVIDQKDIPD PALREQIIQQ VGQYKGDLER   420
YNKTLVLTGD KIQNLKGLEK LSKLQKLELR QLSNVKEITP ELLPESMKKD AELVMVGMTG   480
LEKLNLSGLN RQTLDGIDVN SITHLTSFDI SHNSLDLSEK SEDRKLLMTL MEQVSNHQKI   540
TVKNTAFENQ KPKGYYPQTY DTKEGHYDVD NAEHDILTDF VFGTVTKRNT FIGDEEAFAI   600
YKEGAVDGRQ YVSKDYTYEA FRKDYKGYKV HLTASNLGET VTSKVTATTD ETYLVDVSDG   660
EKVVHHMKLN IGSGAIMMEN LAKGAKVIGT SGDFEQAKKI FDGEKSDRFF TWGQTNWIAF   720
DLGEINLAKE WRLFNAETNT EIKTDSSLNV AKGRLQILKD TTIDLEKMDI KNRKEYLSND   780
ENWTDVAQMD DAKAIFNSKL SNVLSRYWRF CVDGGASSY                         819

SEQ ID NO: 8              moltype = AA  length = 819
FEATURE                   Location/Qualifiers
REGION                    1..819
                          note = Description of Artificial Sequence: Synthetic
                           polypeptide
source                    1..819
                          mol_type = protein
                          organism = synthetic construct
SEQUENCE: 8
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
KDSYVHKLHQ QGTALVQTIG VNELNGRTGL SKDYPDTPEG NKALAAAIVK AFVTDRGVDG   180
LDIEIEHEFT NKRTPEEDAR ALNVFKEIAQ LIGKNGSDKS KLLIMDTTLS VENNPIFKGI   240
AEDLDYLLRQ YYGSQGGEAE VDTINSDWNQ YQNYIDASQF MIGFSFFEES ASKGNLWFDV   300
NEYDPNNPEK GKDIEGTRAK KYAEWQPSTG GLKAGIFSYA IDRDGVAHVP STYKNRTSTN   360
LQRHEVDNIS HTDYTVSRKL KTLMTEDKRY DVIDQKDIPD PALREQIIQQ VGQYKGDLER   420
YNKTLVLTGD KIQNLKGLEK LSKLQKLELR QLSNVKEITP ELLPESMKKD AELVMVGMTG   480
LEKLNLSGLN RQTLDGIDVN SITHLTSFDI SHNSLDLSEK SEDRKLLMTL MEQVSNHQKI   540
TVKNTAFENQ KPKGYYPQTY DTKEGHYDVD NAEHDILTDF VFGTVTKRNT FIGDEEAFAI   600
YKEGAVDGRQ YVSKDYTYEA FRKDYKGYKV HLTASNLGET VTSKVTATTD ETYLVDVSDG   660
EKVVHHMKLN IGSGAIMMEN LAKGAKVIGT SGDFEQAKKI FDGEKSDRFF TWGQTNWIAF   720
DLGEINLAKE WRLFNAETNT EIKTDSSLNV AKGRLQILKD TTIDLEKMDI KNRKEYLSND   780
ENWTDVAQMD DAKAIFNSKL SNVLSRYWRF CVDGGASSY                         819

SEQ ID NO: 9              moltype = AA  length = 819
FEATURE                   Location/Qualifiers
REGION                    1..819
                          note = Description of Artificial Sequence: Synthetic
```

```
                            polypeptide
source                      1..819
                            mol_type = protein
                            organism = synthetic construct
SEQUENCE: 9
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
KDSYVHKLHQ QGTALVQTIG VNELNGRTGL SKDYPDTPEG NKALAAAIVK AFVTDRGVDG   180
LDIGIEHEFT NKRTPEEDAR ALNVFKEIAQ LIGKNGSDKS KLLIMDTTLS VENNPIFKGI   240
AEDLDYLLRQ YYGSQGGEAE VDTINSDWNQ YQNYIDASQF MIGFSFFEES ASKGNLWFDV   300
NEYDPNNPEK GKDIEGTRAK KYAEWQPSTG GLKAGIFSYA IDRDGVAHVP STYKNRTSTN   360
LQRHEVDNIS HTDYTVSRKL KTLMTEDKRY DVIDQKDIPD PALREQIIQQ VGQYKGDLER   420
YNKTLVLTGD KIQNLKGLEK LSKLQKLELR QLSNVKEITP ELLPESMKKD AELVMVGMTG   480
LEKLNLSGLN RQTLDGIDVN SITHLTSFDI SHNSLDLSEK SEDRKLLMTL MEQVSNHQKI   540
TVKNTAFENQ KPKGYYPQTY DTKEGHYDVD NAEHDILTDF VFGTVTKRNT FIGDEEAFAI   600
YKEGAVDGRQ YVSKDYTYEA FRKDYKGYKV HLTASNLGET VTSKVTATTD ETYLVDVSDG   660
EKVVHHMKLN IGSGAIMMEN LAKGAKVIGT SGDFEQAKKI FDGEKSDRFF TWGQTNWIAF   720
DLGEINLAKE WRLFNAETNT EIKTDSSLNV AKGRLQILKD TTIDLEKMDI KNRKEYLSND   780
ENWTDVAQMD DAKAIFNSKL SNVLSRYWRF CVDGGASSY                         819

SEQ ID NO: 10               moltype = AA   length = 819
FEATURE                     Location/Qualifiers
REGION                      1..819
                            note = Description of Artificial Sequence: Synthetic
                             polypeptide
source                      1..819
                            mol_type = protein
                            organism = synthetic construct
SEQUENCE: 10
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
KDSYVHKLHQ QGTALVQTIG VNELNGRTGL SKDYPDTPEG NKALAAAIVK AFVTDRGVDG   180
LDIMIEHEFT NKRTPEEDAR ALNVFKEIAQ LIGKNGSDKS KLLIMDTTLS VENNPIFKGI   240
AEDLDYLLRQ YYGSQGGEAE VDTINSDWNQ YQNYIDASQF MIGFSFFEES ASKGNLWFDV   300
NEYDPNNPEK GKDIEGTRAK KYAEWQPSTG GLKAGIFSYA IDRDGVAHVP STYKNRTSTN   360
LQRHEVDNIS HTDYTVSRKL KTLMTEDKRY DVIDQKDIPD PALREQIIQQ VGQYKGDLER   420
YNKTLVLTGD KIQNLKGLEK LSKLQKLELR QLSNVKEITP ELLPESMKKD AELVMVGMTG   480
LEKLNLSGLN RQTLDGIDVN SITHLTSFDI SHNSLDLSEK SEDRKLLMTL MEQVSNHQKI   540
TVKNTAFENQ KPKGYYPQTY DTKEGHYDVD NAEHDILTDF VFGTVTKRNT FIGDEEAFAI   600
YKEGAVDGRQ YVSKDYTYEA FRKDYKGYKV HLTASNLGET VTSKVTATTD ETYLVDVSDG   660
EKVVHHMKLN IGSGAIMMEN LAKGAKVIGT SGDFEQAKKI FDGEKSDRFF TWGQTNWIAF   720
DLGEINLAKE WRLFNAETNT EIKTDSSLNV AKGRLQILKD TTIDLEKMDI KNRKEYLSND   780
ENWTDVAQMD DAKAIFNSKL SNVLSRYWRF CVDGGASSY                         819

SEQ ID NO: 11               moltype = AA   length = 819
FEATURE                     Location/Qualifiers
REGION                      1..819
                            note = Description of Artificial Sequence: Synthetic
                             polypeptide
source                      1..819
                            mol_type = protein
                            organism = synthetic construct
SEQUENCE: 11
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
KDSYVHKLHQ QGTALVQTIG VNELNGRTGL SKDYPDTPEG NKALAAAIVK AFVTDRGVDG   180
LDINIEHEFT NKRTPEEDAR ALNVFKEIAQ LIGKNGSDKS KLLIMDTTLS VENNPIFKGI   240
AEDLDYLLRQ YYGSQGGEAE VDTINSDWNQ YQNYIDASQF MIGFSFFEES ASKGNLWFDV   300
NEYDPNNPEK GKDIEGTRAK KYAEWQPSTG GLKAGIFSYA IDRDGVAHVP STYKNRTSTN   360
LQRHEVDNIS HTDYTVSRKL KTLMTEDKRY DVIDQKDIPD PALREQIIQQ VGQYKGDLER   420
YNKTLVLTGD KIQNLKGLEK LSKLQKLELR QLSNVKEITP ELLPESMKKD AELVMVGMTG   480
LEKLNLSGLN RQTLDGIDVN SITHLTSFDI SHNSLDLSEK SEDRKLLMTL MEQVSNHQKI   540
TVKNTAFENQ KPKGYYPQTY DTKEGHYDVD NAEHDILTDF VFGTVTKRNT FIGDEEAFAI   600
YKEGAVDGRQ YVSKDYTYEA FRKDYKGYKV HLTASNLGET VTSKVTATTD ETYLVDVSDG   660
EKVVHHMKLN IGSGAIMMEN LAKGAKVIGT SGDFEQAKKI FDGEKSDRFF TWGQTNWIAF   720
DLGEINLAKE WRLFNAETNT EIKTDSSLNV AKGRLQILKD TTIDLEKMDI KNRKEYLSND   780
ENWTDVAQMD DAKAIFNSKL SNVLSRYWRF CVDGGASSY                         819

SEQ ID NO: 12               moltype = AA   length = 819
FEATURE                     Location/Qualifiers
REGION                      1..819
                            note = Description of Artificial Sequence: Synthetic
                             polypeptide
source                      1..819
                            mol_type = protein
                            organism = synthetic construct
SEQUENCE: 12
MDKHLLVKRT LGCVCAATLM GAALATHHDS LNTVKAEEKT VQTGKTDQQV GAKLVQEIRE    60
GKRGPLYAGY FRTWHDRAST GIDGKQQHPE NTMAEVPKEV DILFVFHDHT ASDSPFWSEL   120
```

```
KDSYVHKLHQ QGTALVQTIG VNELNGRTGL SKDYPDTPEG NKALAAAIVK AFVTDRGVDG  180
LDIQIEHEFT NKRTPEEDAR ALNVFKEIAQ LIGKNGSDKS KLLIMDTTLS VENNPIFKGI  240
AEDLDYLLRQ YYGSQGGEAE VDTINSDWNQ YQNYIDASQF MIGFSFFEES ASKGNLWFDV  300
NEYDPNNPEK GKDIEGTRAK KYAEWQPSTG GLKAGIFSYA IDRDGVAHVP STYKNRTSTN  360
LQRHEVDNIS HTDYTVSRKL KTLMTEDKRY DVIDQKDIPD PALREQIIQQ VGQYKGDLER  420
YNKTLVLTGD KIQNLKGLEK LSKLQKLELR QLSNVKEITP ELLPESMKKD AELVMVGMTG  480
LEKLNLSGLN RQTLDGIDVN SITHLTSFDI SHNSLDLSEK SEDRKLLMTL MEQVSNHQKI  540
TVKNTAFENQ KPKGYYPQTY DTKEGHYDVD NAEHDILTDF VFGTVTKRNT FIGDEEAFAI  600
YKEGAVDGRQ YVSKDYTYEA FRKDYKGYKV HLTASNLGET VTSKVTATTD ETYLVDVSDG  660
EKVVHHMKLN IGSGAIMMEN LAKGAKVIGT SGDFEQAKKI FDGEKSDRFF TWGQTNWIAF  720
DLGEINLAKE WRLFNAETNT EIKTDSSLNV AKGRLQILKD TTIDLEKMDI KNRKEYLSND  780
ENWTDVAQMD DAKAIFNSKL SNVLSRYWRF CVDGGASSY                        819

SEQ ID NO: 13           moltype = AA   length = 819
FEATURE                 Location/Qualifiers
REGION                  1..819
                        note = Description of Artificial Sequence: Synthetic
                        polypeptide
source                  1..819
                        mol_type = protein
                        organism = synthetic construct
SEQUENCE: 13
MDKHLLVKRT LGCVCAATLM GAALATHHDS LNTVKAEEKT VQTGKTDQQV GAKLVQEIRE   60
GKRGPLYAGY FRTWHDRAST GIDGKQQHPE NTMAEVPKEV DILFVFHDHT ASDSPFWSEL  120
KDSYVHKLHQ QGTALVQTIG VNELNGRTGL SKDYPDTPEG NKALAAAIVK AFVTDRGVDG  180
LDISIEHEFT NKRTPEEDAR ALNVFKEIAQ LIGKNGSDKS KLLIMDTTLS VENNPIFKGI  240
AEDLDYLLRQ YYGSQGGEAE VDTINSDWNQ YQNYIDASQF MIGFSFFEES ASKGNLWFDV  300
NEYDPNNPEK GKDIEGTRAK KYAEWQPSTG GLKAGIFSYA IDRDGVAHVP STYKNRTSTN  360
LQRHEVDNIS HTDYTVSRKL KTLMTEDKRY DVIDQKDIPD PALREQIIQQ VGQYKGDLER  420
YNKTLVLTGD KIQNLKGLEK LSKLQKLELR QLSNVKEITP ELLPESMKKD AELVMVGMTG  480
LEKLNLSGLN RQTLDGIDVN SITHLTSFDI SHNSLDLSEK SEDRKLLMTL MEQVSNHQKI  540
TVKNTAFENQ KPKGYYPQTY DTKEGHYDVD NAEHDILTDF VFGTVTKRNT FIGDEEAFAI  600
YKEGAVDGRQ YVSKDYTYEA FRKDYKGYKV HLTASNLGET VTSKVTATTD ETYLVDVSDG  660
EKVVHHMKLN IGSGAIMMEN LAKGAKVIGT SGDFEQAKKI FDGEKSDRFF TWGQTNWIAF  720
DLGEINLAKE WRLFNAETNT EIKTDSSLNV AKGRLQILKD TTIDLEKMDI KNRKEYLSND  780
ENWTDVAQMD DAKAIFNSKL SNVLSRYWRF CVDGGASSY                        819

SEQ ID NO: 14           moltype = AA   length = 819
FEATURE                 Location/Qualifiers
REGION                  1..819
                        note = Description of Artificial Sequence: Synthetic
                        polypeptide
source                  1..819
                        mol_type = protein
                        organism = synthetic construct
SEQUENCE: 14
MDKHLLVKRT LGCVCAATLM GAALATHHDS LNTVKAEEKT VQTGKTDQQV GAKLVQEIRE   60
GKRGPLYAGY FRTWHDRAST GIDGKQQHPE NTMAEVPKEV DILFVFHDHT ASDSPFWSEL  120
KDSYVHKLHQ QGTALVQTIG VNELNGRTGL SKDYPDTPEG NKALAAAIVK AFVTDRGVDG  180
LDITIEHEFT NKRTPEEDAR ALNVFKEIAQ LIGKNGSDKS KLLIMDTTLS VENNPIFKGI  240
AEDLDYLLRQ YYGSQGGEAE VDTINSDWNQ YQNYIDASQF MIGFSFFEES ASKGNLWFDV  300
NEYDPNNPEK GKDIEGTRAK KYAEWQPSTG GLKAGIFSYA IDRDGVAHVP STYKNRTSTN  360
LQRHEVDNIS HTDYTVSRKL KTLMTEDKRY DVIDQKDIPD PALREQIIQQ VGQYKGDLER  420
YNKTLVLTGD KIQNLKGLEK LSKLQKLELR QLSNVKEITP ELLPESMKKD AELVMVGMTG  480
LEKLNLSGLN RQTLDGIDVN SITHLTSFDI SHNSLDLSEK SEDRKLLMTL MEQVSNHQKI  540
TVKNTAFENQ KPKGYYPQTY DTKEGHYDVD NAEHDILTDF VFGTVTKRNT FIGDEEAFAI  600
YKEGAVDGRQ YVSKDYTYEA FRKDYKGYKV HLTASNLGET VTSKVTATTD ETYLVDVSDG  660
EKVVHHMKLN IGSGAIMMEN LAKGAKVIGT SGDFEQAKKI FDGEKSDRFF TWGQTNWIAF  720
DLGEINLAKE WRLFNAETNT EIKTDSSLNV AKGRLQILKD TTIDLEKMDI KNRKEYLSND  780
ENWTDVAQMD DAKAIFNSKL SNVLSRYWRF CVDGGASSY                        819

SEQ ID NO: 15           moltype = AA   length = 995
FEATURE                 Location/Qualifiers
REGION                  1..995
                        note = Description of Artificial Sequence: Synthetic
                        polypeptide
source                  1..995
                        mol_type = protein
                        organism = synthetic construct
SEQUENCE: 15
MDKHLLVKRT LGCVCAATLM GAALATHHDS LNTVKAEEKT VQVQKGLPSI DSLHYLSENS   60
KKEFKEELSK AGQESQKVKE ILAKQQADK QAQELAKMKI PEKIPMKPLH GPLYGGYFRT  120
WHDKTSDPTE KDKVNSMGEL PKEVDLAFIF HDWTKDYSLF WKELATKHVP KLNKQGTRVI  180
RTIPWRFLAG GDNSGIAEDT SKYPNTPEGN KALAKAIVDE YVVYKYNLDGL DVMVEHDSIP  240
KVDKKEDTAG VERSIQVFEE IGKLIGPKGV DKSRLFIMDS TYMADKNPLI ERGAPYINLL  300
LVQVYGSQGE KGGWEPVSNR PEKTMEERWQ GYSKYIRPEQ YMIGFSFYEE NAQEGNLWYD  360
INSRKDEDKA NGINTDITGT RAERYARWQP KTGGVKGGIF SYAIDRDGVA HQPKKYAKQK  420
EFKDATDNIF HSDYSVSKAL KTVMLKDKSY DLIDEKDFPD KALREAVMAQ VGTRKGDLER  480
FNGTLRLDNP AIQSLEGLNK FKKLAQLDLI GLSRITKLDR SVLPANMKPG KDTLETVLET  540
```

```
YKKDNKEEPA TIPPVSLKVS GLTGLKELDL SGFDRETLAG LDAATLTSLE KVDISGNKLD 600
LAPGTENRQI FDTMLSTISN HVGSNEQTVK FDKQKPTGHY PDTYGKTSLR LPVANEKVDL 660
QSQLLFGTVT NQGTLINSEA DYKAYQNHKI AGRSFVDSNY HYNNFKVSYE NYTVKVTDST 720
LGTTTDKTLA TDKEETYKVD FFSPADKTKA VHTAKVIVGD EKTMMVNLAE GATVIGGSAD 780
PVNARKVFDG QLGSETDNIS LGWDSKQSII FKLKEDGLIK HWRFFNDSAR NPETTNKPIQ 840
EASLQIFNIK DYNLDNLLEN PNKFDDEKYW ITVDTYSAQG ERATAFSNTL NNITSKYWRV 900
VFDTKGDRYS SPVVPELQIL GYPLPNADTI MKTVTTAKEL SQQKDKFSQK MLDELKIKEM 960
ALETSLNSKI FDVTAINANA GVLKDCIEKR QLLKK                             995

SEQ ID NO: 16          moltype = AA  length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 16
MKKIFFAQCS ILLLMLGSCS KMTEDMTPES VNKEASVKSA TALAGSNGVC IAYYITDGRN  60
PTFKLKDIPD KVDMVILFGL KYWSLQDTTK LPGGTGMMGS FKSYKDLDTQ IRSLQSRGIK 120
VLQNIDDDVS WQSSKPGGFA SAAAYGDAIK SIVIDKWKLD GISLAIEHSG AKPNPIPTFP 180
GYAATGYNGW YSGSMAATPA FLNVISELTK YFGTTAPNNK QLQIASGIDV YAWNKIMENF 240
RNNFNYIQLQ SYGANVSRTQ LMMNYATGTN KIPASKMVFG AYAEGGTNQA NDVEVAKWTP 300
TQGAKGGMMI YTYNSNVSYA NAVRDAVKN                                  329
```

Fc GLYCAN REMODELING PLATFORM METHOD FOR SITE-SPECIFIC ANTIBODY CONJUGATION AND APPLICATIONS THEREOF

CROSS-REFERENCE TO RELATED APPLICATION

This application claims benefit and priority to PCT Application No. PCT/US22/26213 filed on Apr. 25, 2022, U.S. Provisional Application No. 63/178,719, filed Apr. 23, 2021; U.S. Provisional Application No. 63/264,012, filed Nov. 12, 2021; and U.S. Provisional Application No. 63/264,013, filed Nov. 12, 2021, which are incorporated herein by reference in their entireties.

This invention was made with government support under Grant Number GM096973 and AI155716 awarded by the National Institutes of Health. The government has certain rights in the invention.

SEQUENCE LISTING

The application contains a Sequence Listing which has been submitted electronically in .XML format and is hereby incorporated by reference in its entirety. Said .XML copy, created on Jan. 30, 2023, is named "1475-79 PCT US TK-1.xml" and is 32,901 bytes in size. The sequence listing contained in this .XML file is part of the specification and is hereby incorporated by reference herein in its entirety.

TECHNICAL FIELD

The present disclosure provides a one-pot chemoenzymatic method for site-specific modification and conjugation of antibodies at their Fc glycan site to produce structurally well-defined antibody conjugates carrying defined drugs and other entities. The method is enabled by the discovery that certain endoglycosidases have the ability to both deglycosylate an antibody and to recognize selectively modified small disaccharide oxazolines for transglycosylation on antibodies without hydrolysis of the resulting products. The remarkable difference in hydrolytic activity of the disclosed endoglycosidases toward the parent antibody and the resulting transglycosylation product enables a simple, "one-pot" procedure that combines the antibody deglycosylation and transglycosylation with tagged sugar oxazolines without the need to separate the deglycosylation intermediate and the enzyme before transglycosylation. The azide-tagged antibodies can be used for producing structurally well-defined antibody-drug conjugates with well-defined antibody-drug ratios and can be also applied to producing antibody conjugates with other entities including fluorescent labels and various ligands.

BACKGROUND

Therapeutic antibodies are an important class of biologics that have been used for the treatment of many challenging diseases, such as cancer, autoimmune disorders, and inflammatory diseases. Featured by their high specificity and affinity, the monoclonal antibodies (mAbs) have fewer off-target side effects as compared to small-molecule pharmaceuticals, thus in addition to being used as therapeutic agents, mAbs also provide a promising platform for targeted delivery of small molecules. Antibody with drug conjugates (ADCs) that combine the specificity of antibodies and the high potency of drugs, hold great promise for targeted cell killing. Accordingly, methods are desired for easily and efficiently generating said antibody with drug conjugates.

SUMMARY

The present disclosure provides for the synthesis of IgG antibodies and Fc fragments thereof, wherein a desired sugar chain is added to a core fucosylated or nonfucosylated GlcNAc-acceptor, including a fucosylated or nonfucosylated GlcNAc-IgG acceptor. As such, the present disclosure allows for the synthesis and remodeling of therapeutic antibodies and Fc fragments thereof to provide for certain biological activities, such as, prolonged half-life time in vivo, less immunogenicity, enhanced in vivo activity, increased targeting ability, and/or ability to deliver a therapeutic agent.

In one aspect a one pot chemoenzymatic remodeling method is provided for both deglycosylation and transglycosylation reactions in a one-pot manner to provide an azido tagged antibody. The provided method comprises the steps of:

(a) providing a single reactor, container, column, or pot;
(b) introducing a single endoglycosidase having both deglycosylation and transglycosylation activity, or mutants thereof;
(c) introducing an antibody for deglycosylation by the single endoglycosidase thereby providing a deglycosylated intermediate that contains at least one N-acetylglucosamine (GlcNAc) or core-fucosylated N-acetylglucosamine (Fucα1,6GlcNAc) acceptor;
(d) providing an azido-modified glycan oxazoline comprising a disaccharide core; and
(e) transglycosylating the azido-modified glycan oxazoline to the N-acetylglucosamine (GlcNAc) or core-fucosylated N-acetylglucosamine (Fucα1,6GlcNAc) acceptor by the single endoglycosidase to provide the azido-tagged antibody.

In another embodiment, a one pot chemoenzymatic remodeling method is provided for both deglycosylation and transglycosylation reactions in a one-pot manner to provide an azido tagged antibody. The provided method comprises the steps of:

(a) providing a single reactor, container, column, or pot;
(b) introducing a first endoglycosidase having deglycosylation activity, or mutants thereof;
(c) introducing an antibody for deglycosylation by the endoglycosidase thereby providing a deglycosylated intermediate that contains at least one N-acetylglucosamine (GlcNAc) or core-fucosylated N-acetylglucosamine (Fucα1,6GlcNAc) acceptor;
(d) providing a second endoglycosidase having transglycosylation activity and an azido-modified glycan oxazoline comprising a disaccharide core; and
(e) transglycosylating the azido-modified glycan oxazoline to the N-acetylglucosamine (GlcNAc) or core-fucosylated N-acetylglucosamine (Fucα1,6GlcNAc) acceptor by the second endoglycosidase to provide the azido-tagged antibody and wherein the azido-tagged antibody is resistant to hydrolysis by the first endoglycosidase.

In another embodiment, a one pot chemoenzymatic remodeling method is provided wherein the conjugate is a M6P glycan wherein said resulting M6P-tagged antibody targets lysosomal mediated target degradation. Said method comprises the steps for both deglycosylation and transglycosylation reactions in the one pot to provide an M6P tagged antibody, the method comprising:

(a) providing a single reactor, container, column, or pot;
(b) introducing a single endoglycosidase wherein the endoglycosidase has both deglycosylation and transglycosylation ability;
(c) introducing an antibody for deglycosylation by the single endoglycosidase thereby providing a deglycosylated intermediate that contains at least one N-acetylglucosamine (GlcNAc) or core-fucosylated N-acetylglucosamine (Fucα1,6GlcNAc) acceptor;
(d) providing an M6P-Glycan oxazoline; and
(e) transglycosylating the M6P-Glycan oxazoline to the N-acetylglucosamine (GlcNAc) or core-fucosylated N-acetylglucosamine (Fucα1,6GlcNAc) acceptor by the single endoglycosidase to provide the M6P-tagged antibody.

In another embodiment, a one pot chemoenzymatic remodeling method is provided wherein the conjugate is a M6P glycan and wherein said resulting M6P-tagged antibody targets lysosomal mediated target degradation. Said method comprises the steps for both deglycosylation and transglycosylation reactions in the one pot to provide an M6P tagged antibody, the method comprising:
(a) providing a single reactor, container, column, or pot;
(b) introducing a first endoglycosidase wherein the endoglycosidase has deglycosylation ability;
(c) introducing an antibody for deglycosylation by the single endoglycosidase thereby providing a deglycosylated intermediate that contains at least one N-acetylglucosamine (GlcNAc) or core-fucosylated N-acetylglucosamine (Fucα1,6GlcNAc) acceptor;
(d) providing a second endoglycosidase and a M6P-Glycan oxazoline; and
(e) transglycosylating the M6P-Glycan oxazoline to the N-acetylglucosamine (GlcNAc) or core-fucosylated N-acetylglucosamine (Fucα1,6GlcNAc) acceptor by the second endoglycosidase to provide the M6P-tagged antibody.

In an embodiment, the antibody molecules for deglycosylation can be any antibody characterized by the presence of one or more glycans that can act as substrates for deglycosylation activity through a endoglycosidases mediated reaction. Such antibodies, include for example, those antibodies having high specificity and affinity to antigens expressed on a target cell of interest. In a non-limiting embodiment, the antigens are expressed on target cancer cells. In another embodiment, the antibodies bind to antigens, such as extracellular and membrane-associated proteins for use in targeted lysosomal degradation. Antibodies may also bind to targeted pathogen antigens. Such antigens include, for example, those associated with viral, bacterial, fungal and parasitic infections of a subject.

In an embodiment, the resulting azido-tagged antibodies are further modified with conjugation to other ligands to provide an antibody-conjugate. In an embodiment, the antibody-conjugate comprises a ligand selected from drugs, toxins, labels, proteins, small molecules, thio, biotin, and fluorescent label. In an embodiment, the azido-tagged antibody may be modified with conjugation to other ligands by a click chemistry reaction.

In the practice of the provided remodeling methods, a number of disaccharide oxazolines may be used as substrates in the transglycosylation step. Such disaccharide ozazolines include, for example, those of Group I Manβ1,4GlcNAc disaccharides depicted in FIG. 4 and having the following general structure:

Group I, Manβ1,4GlcNAc based oxazolines

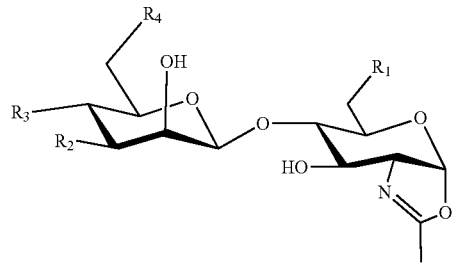

R1, R2, R3, R4=OH, N$_3$, PEG-linked N$_3$, a fluorescent probe, a biotin moiety, a ligand, or a drug
Man: mannose; GlcNAc, N-acetylglucosamine PEG linker: a polyethylene glycol (PEG) linker In another embodiment, the disaccharide oxazolines include, for example, those of Group II Glcβ1,4GlcNAc disaccharides depicted in FIG. 5 having the following general structure:

Group II, Glcβ1,4GlcNAc Based Oxazolines

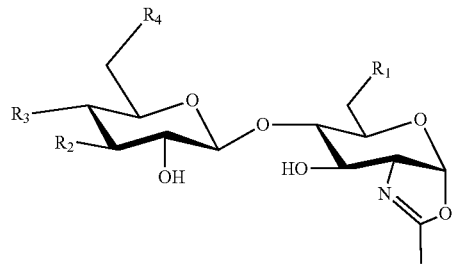

R1, R2, R3, R4=OH, N$_3$, PEG-linked N$_3$, a fluorescent probe, a biotin moiety, a ligand, or a drug
Glc: Glucose; GlcNAc, N-acetylglucosamine PEG linker: a polyethylene glycol (PEG) linker In another embodiment, the disaccharide oxazolines include, for example, those of Group III Galβ1,4GlcNAc depicted in FIG. 6 and having the following general structure:

Group III, Galβ1,4GlcNAc Based Oxazolines

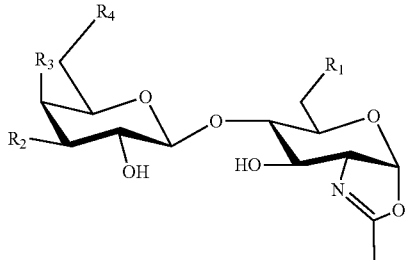

R1, R2, R3, R4=OH, N$_3$, PEG-linked N$_3$, a fluorescent probe, a moiety, a ligand, or a drug
Gal, galactose; GlcNAc, N-acetylglucosamine PEG linker: a polyethylene glycol (PEG) linker Still further, M6P glycan oxazolines for use in the disclosed remodeling methods include, for example, those depicted in FIG. 8.

In an embodiment, the azido-modified glycan oxazoline may comprise a disaccharide core derived from synthetic or natural disaccharides, including Manβ1,4GlcNAc, Glcβ1, 4GlcNAc, and Galβ1,4GlcNAc (LacNAc). Multiple polyethylene linkers, or other molecular linkers may be attached to the disaccharide core to forming a dendrimer. In one aspect, the azido-modified glycan oxazoline further comprises spacers. Such spacers include for example, oligoethylene spacers including polyethylene (PEG) linkers.

In yet another aspect, provided is an activated oligosaccharide moiety, such as a disaccharide oxazoline, as well as its selectively modified derivatives such as those with specific tags are provided in the practice of the provided remodeling methods.

It is envisioned that the oligosaccharide oxazoline or sialoglycan oxazoline having a predetermined oligosaccharide component with a defined number and type of sugar residues may comprise an additional moiety or tag thereby by passing the need for conducting a click chemical reaction for conjugation of the moiety or tag to the antibody. Moieties and tags include, for example, a therapeutic agent or drug such as for treating cancer, viral infections, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof. In an embodiment, such tags may also be added to the azido modified antibody using click chemistry reactions which are well known to those skilled in the art.

As such, the present disclosure further provides a delivery device for delivering a drug or therapeutic agent having biological activity to treat a condition, the delivery device comprising: a remodeled IgG or IgG-Fc fragment having a predetermined sugar chain and a therapeutic agent or drug attached to the terminal sugar residue. Antibodies related to cancer or other diseases may be remodeled for individual fit to certain receptors thereby increasing biological activity.

In another embodiment, the provided delivery device is designed to deliver a detectable label or marker to a targeted antigen for diagnostic and prognostic uses. Said a delivery device comprises a remodeled IgG or IgG-Fc fragment having a predetermined sugar chain and the detectable label or marker attached to the remodeled antibody. A "detectable label" or a "marker" refers to a composition that is detectable by spectroscopic, photochemical, biochemical, immunochemical, radioactive or chemical means. For example, a useful label includes $^{32}P$, $^{35}S$, fluorescent dyes, electron-dense reagents, enzymes (e.g., enzymes that are generally used in ELISA), biotin-streptavidin, digoxigenin, hapten, proteins or nucleic acid molecules with a sequence complementary to a target. The detectable label often generates a measurable signal, e.g., a radioactive signal, a color signal or a fluorescent signal, which is usable to quantify an amount of the detectable moiety that binds to the target antigen. Quantification of the signal may be accomplished by, for example, scintillation counting, density gauge, flow cell analysis, ELISA, or direct analysis by mass spectroscopy. Those skilled in the art are familiar with techniques and detection means for a label compound of interest. These techniques and methods are conventional and well known in the art.

In yet another aspect, embodiments of the present disclosure provide a substantially homogeneous preparation of core fucosylate or nonfucosylated antibody(ies) or Fc fragment thereof having a predetermined oligosaccharide moiety, wherein the substantially homogeneous preparation is produced by any of the aforementioned methods. Also provided are compositions comprising such homogeneous preparations.

The present disclosure provides efficient methods for producing homogeneous and site-specific antibody-drug conjugates with well-defined antibody-drug ratios (DARs). The disclosed one pot modeling method provides an efficient method for producing antibody-drug conjugates (ADCs) using any given antibody, linker, and payload.

In an embodiment, a method is provided of treating a subject wherein said treatment typically comprises administering to the subject, of an effective amount of an a remodeled antibody generated using the one pot chemoenzymatic remodeling methods disclosed herein.

In further embodiments, pharmaceutical compositions comprising a remodeled antibody generated using the one pot chemoenzymatic remodeling methods disclosed herein and a pharmaceutical acceptable carrier are provided. The antibodies exhibit properties for use as therapeutic agents, e.g. in the treatment of cancer for example.

In yet another embodiment, kits comprising a remodeled antibody are provided. Such kits contain, in addition to the remodeled antibody, materials useful for the treatment of diseases, or for diagnosis of a disease as described herein. The kits may comprise one or more of the following components: a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle).

Other aspects, features and embodiments of the present disclosure will be more fully apparent from the ensuing disclosure and appended claims.

BRIEF DESCRIPTION OF THE DRAWINGS

Various embodiments of the present disclosure are described herein with reference to the drawings.

FIG. 4. General structures of Manβ1,4GlcNAc based disaccharide oxazolines used for the enzymatic glycan remodeling.

FIG. 5. General structures of Glcβ1,4GlcNAc based disaccharide oxazolines used for the enzymatic glycan remodeling.

FIG. 6. General structures of Galβ1,4GlcNAc based disaccharide oxazolines used for the enzymatic glycan remodeling.

FIG. 25. Scheme 1. Chemical synthesis of azido-tagged disaccharide oxazolines. Reagents and conditions: a) Pd/C, $H_2$, HCl (aq) THF/$H_2O$, RT, 5, 97%, 12, 93%, 22, 97%; b) $CH_3ONa$, $CH_3OH$, 50° C.; c) BnBr, NaH, DMF, 0° C.~RT, 8, 87% for 2 steps, 18, 68% for 3 steps; d) $BH_3$·THF, $Bu_2BOTf$, $CH_2Cl_2$, 0° C., 91%; e) AcSH, pyridine/$CHCl_3$, 50° C., 10, 89%, 19, 79%; f) $N_3(CH_2CH_2O)_3Ts$, NaH, DMF, 0° C.~RT, 11, 85%, 21, 85%; g) $TfN_3$, $K_2CO_3$, $CuSO_4CH_2Cl_2$/MeOH/$H_2O$, RT, 13, 81%, 23, 85%; h) DMC, $Et_3N$, $H_2O$, 0° C., 14, 94%, 24, 96%; i) TMSOTf, 4 Å MS, $CH_2Cl_2$, −40° C., 86%; j) TBDPSCl, imidazole, DMF, RT; k) TBAF, THF, 40° C., 82%.

FIG. 28A deconvoluted mass of intact ADC 33; FIG. 28B deconvoluted mass of the Fc domain of 33; FIG. 28C deconvoluted mass of intact ADC 34; FIG. 28D deconvoluted mass of the Fc domain of 34; FIG. 28E deconvoluted mass of intact ADC 35; FIG. 28F deconvoluted mass of the Fc domain of 35.

FIG. 35. Screening of the Transglycosylation Conditions. [a]Based on each glycosylation site. [b]Nonfucosylated antibody (GlcNAc-Herceptin) was used as the acceptor, as these three enzymes do not recognize the Fucα1,6GlcNAc-antibody as the acceptor. [c]After 6 h at room temperature. [d]Not determined.

(FIG. 39A) Whole antibody analysis of compound 36; (FIG. 39B) whole antibody analysis of compound 46; (FIG. 39C) Fc domain of compound 36; and (FIG. 39D) Fc domain of compound 46. Asterisked peaks indicate the ion fragments derived from the intact antibody (FIG. 39B) or the Fc domain (FIG. 33D). Shift of molecular weight for the whole antibody: 161,880−148,262=13,618≈1702×8 (equaling to attachment of eight payloads) and for the Fc fragment: 32,143−25,332=6811≈1702×4 (equaling to attachment of four payloads).

FIG. 42. The lysosome-targeting chimera (LYTAC) strategy employing CI-MPR-mediated trafficking of extracellular proteins to lysosomes. a) the conjugation method reported by Bertozzi et al;[14] b) the site-specific chemoenzymatic method described in the present study.

FIG. 43. Screening of Transglycosylation conditions.

FIG. 46A Fab glycans from commercial cetuximab; FIG. 46B Fc glycans from commercial cetuximab; FIG. 46C Fab glycans from glycoengineered cetuximab 9; FIG. 46D Fc glycans from glycoengineered cetuximab 9 (without permethylation).

FIG. 49A Representative FACS analysis of surface HER2 levels; FIG. 49B Surface HER2 levels after treatment with trastuzumab or 3; FIG. 49C Representative FACS analysis of surface EGFR levels; FIG. 49D Surface EGFR levels after treatment with cetuximab or 9. All assays were performed in triplicate.

FIG. 50 Tested Oxazoline Compounds.

DETAILED DESCRIPTION

Figure 1:
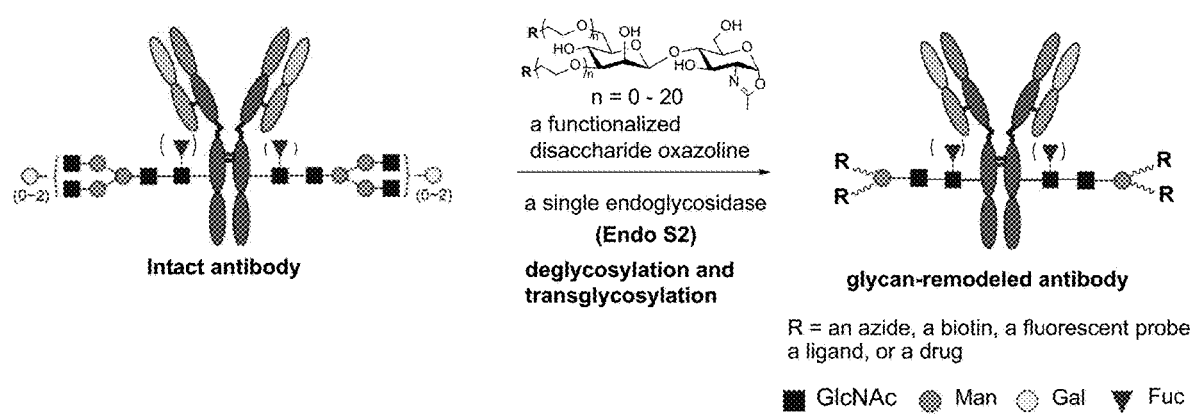
FIG. 1. Representative preparation of azido-tagged or other entity-conjugated antibodies using the single-enzyme one-pot method. The one-pot simultaneous deglycosylation and transglycosylation by a single endoglycosidase such as wild type Endo-S2 is based on the observation that Endo-S2 can recognize the modified disaccharide oxazoline for transglycosylation with low or no hydrolytic activity on the transglycosylation product, while Endo-S2 is known to efficiently hydrolyze the natural or recombinant antibody.

Disclosed herein are modified antibodies prepared via glycan engineering. The disclosure relates to the Fc region of an antibody molecule, wherein the Fc region is specifically glycosylated with oligosaccharides that increase the efficacy and stability of the Fc region, and the antibody or antibody fragment comprising the Fc region. In some embodiments the specifically glycosylated Fc fragment comprises a monoclonal antibody, preferably a human or humanized monoclonal antibody. Methods for generating such Fc glycosylated antibodies or antibody fragments by glycan engineering are disclosed herein Unless defined otherwise, all technical and scientific terms used herein have the same meanings as commonly understood by those skill in the art to which the present disclosure belongs. Any methods and materials similar or equivalent to those described herein can be used in the practice or testing of the disclosed methods and compositions. All publications and patents specifically mentioned herein are incorporated by reference for all purposes including describing and disclosing the chemicals, cell lines, vectors, animals, instruments, statistical analysis and methodologies which are reported in the publications which might be used in connection with the subject matter of the present disclosure.

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan.

The term "antibody" (Ab) as used herein includes monoclonal antibodies, polyclonal antibodies, multi-specific antibodies (e.g., bispecific antibodies), and antibody fragments, so long as they exhibit the desired biological activity. The term "immunoglobulin" (Ig) is used interchangeably with "antibody" herein. A "human antibody" as used herein refers to an antibody naturally existing in humans, a functional fragment thereof, or a humanized antibody, i.e., a genetically engineered antibody a portion of which (e.g., a frame region or the Fc region) derives from a naturally-occurring human antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts.

A "mammal" for purposes of treatment, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" if, after receiving a therapeutic amount of an antibody according to the methods of the present disclosure, relief to some extent from one or more of the symptoms associated with the specific pathologic condition or disorder; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating." "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature. Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The term "cytotoxic agent" as used herein refers to a substance that inhibits or prevents the function of cells and/or causes destruction of cells. The term is intended to include radioactive isotopes, chemotherapeutic agents e.g., methotrexate, adriamycin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Such inhibitory agents include, for example, the vinca alkaloids (vincristine, vinorelbine and vinblastine), taxanes, and topoisomerase II inhibitors such as doxorubicin, epirubicin, daunorubicin, etoposide, bleomycin, tamoxifen, prednisone, dacarbazine, mechlorethamine, cisplatin, methotrexate, 5-fluorouracil, and ara-C.

The present disclosure provides for the synthesis of IgG antibodies, or Fc fragments thereof, wherein a desired sugar chain is added to a core fucosylated or nonfucosylated GlcNAc-acceptor, including fucosylated or nonfucosylated GlcNAc-IgG acceptor. As such, the present disclosure allows for the synthesis and remodeling of therapeutic antibodies, or Fc fragments thereof, to provide for certain biological activities, such as, prolonged half-life time in vivo, less immunogenicity, enhanced in vivo activity, increased targeting ability, and/or ability to deliver a therapeutic agent.

In one aspect a one pot chemoenzymatic remodeling method is provided for both deglycosylation and transglycosylation reactions in a one-pot manner to provide an azido tagged antibody (FIG. 1). The provided method comprises the steps of:

(a) providing a single reactor, container, column, or pot;
(b) introducing a single endoglycosidase having both deglycosylation and transglycosylation activity, or mutants thereof;
(c) introducing an antibody for deglycosylation by the single endoglycosidase thereby providing a deglycosylated intermediate that contains at least one N-acetylglucosamine (GlcNAc) or core-fucosylated N-acetylglucosamine (Fucα1,6GlcNAc) acceptor; and
(d) providing an azido-modified glycan oxazoline comprising a disaccharide core; and transglycosylating the azido-modified glycan oxazoline to the N-acetylglucosamine (GlcNAc) or core-fucosylated N-acetylglucosamine (Fucα1,6GlcNAc) acceptor by the single endoglycosidase to provide the azido-tagged antibody.

Figure 2:
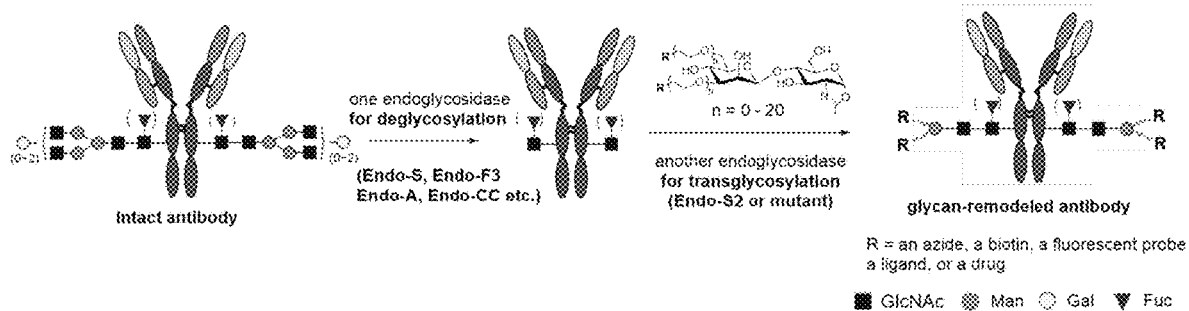
FIG. 2. Representative preparation of azido-tagged or other entity-conjugated antibodies using the two-enzyme one-pot method. The deglycosylation is performed by one endoglycosidase and the transglycosylation is carried out by another endoglycosidase without the need to separate the intermediate and the first endoglycosidase for the transglycosylation. The one-pot glycan remodeling is based on the observation that antibody product carrying the modified glycan are resistant to hydrolyze by the two enzymes used.

In another embodiment, a one pot two enzyme remodeling method is provided for both deglycosylation and transglycosylation reactions in a one-pot manner to provide an azido tagged antibody (FIG. 2). The provided method comprises the steps of:
(a) providing a single reactor, container, column, or pot;
(b) introducing a first endoglycosidase having deglycosylation activity, or mutants thereof;
(c) introducing an antibody for deglycosylation by the endoglycosidase thereby providing a deglycosylated intermediate that contains at least one N-acetylglucosamine (GlcNAc) or core-fucosylated N-acetylglucosamine (Fucα1,6GlcNAc) acceptor; and
(d) providing a second endoglycosidase having transglycosylation activity and an azido-modified glycan oxazoline comprising a disaccharide core; and transglycosylating the azido-modified glycan oxazoline to the N-acetylglucosamine (GlcNAc) or core-fucosylated N-acetylglucosamine (Fucα1,6GlcNAc) acceptor by the second endoglycosidase to provide the azido-tagged antibody and wherein the azido-tagged antibody is resistant to hydrolysis by the first endoglycosidase.

Figure 3:
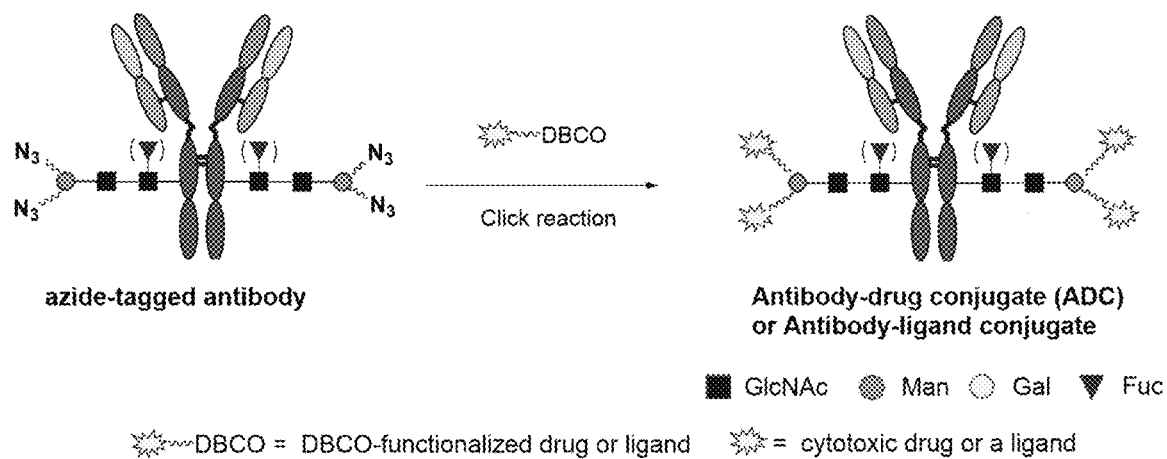
FIG. 3. Click conjugation of drug or other entities (various ligands) to the azide-tagged antibodies to provide antibody-drug conjugates or other antibody-ligand conjugates.
Figure 7:
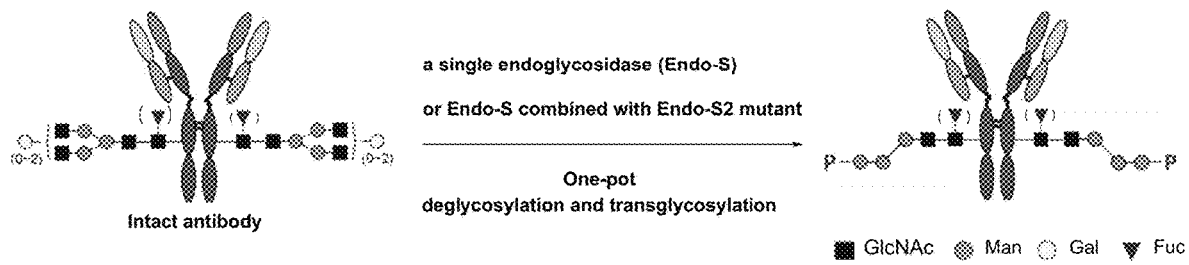
FIG. 7. A one-pot chemoenzymatic glycan remodeling method to introduce high-affinity M6P ligand to antibody. For the single-enzyme one-pot method, the deglycosylation and transglycosylation can be carried out by a single endoglycosidase (Endo-S) as Endo-S is able to recognize the truncated M6P glycan oxaozoline for transglycosylation without hydrolysis of the product. For the two-enzyme one-pot method, Endo-S may be used for deglycosylation, and an Endo-S2 mutant (such as EndoS2 D184M) may be used for transglycosylation, which is found to be more efficient than the Endo-S for transglycosylation.

In another embodiment, the above two methods may further comprise a click chemistry step for conjugation of a ring-strained cyclooctyne moiety-containing drug or ligand to the azide-tagged antibody via ring-strained cycloaddition reaction to provide homogeneous antibody-drug conjugates or antibody-ligand conjugates. (FIG. 3).

In an aspect, the present disclosure provides for use in the provided one pot method of an activated oligosaccharide moiety, such as an azide-tagged disaccharide oxazoline, as well as its selectively modified derivatives. Such disaccharide oxazolines are utilized as donor substrates for an efficient chemoenzymatic synthesis of homogeneous core fucosylated or nonfucosylated IgG antibodies and IgG-Fc fragments.

In an embodiment, the azido-modified glycan oxazoline for use in the above methods is selected from the group consisting of the following oxazoline structures: Group I based on the Manβ1,4GlcNAc disaccharide structures as depicted in FIG. 4, Group II based on the Glcβ1,4GlcNAc disaccharide structures as depicted in FIG. 5, and Group III based on the Manβ1,4GlcNAc disaccharide structures of FIG. 6.

In the practice of the provided remodeling methods, a number of disaccharide oxazolines may be used as substrates in the transglycosylation step. Such disaccharide ozazolines include, for example, those of Group I Manβ1,4GlcNAc disaccharides depicted in FIG. 4 and having the following general structure:

Group I, Manβ1,4GlcNAc Based Oxazolines

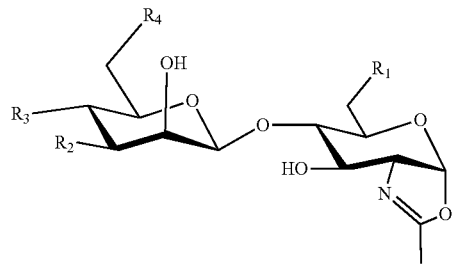

R1, R2, R3, R4=OH, N₃, PEG-linked N₃, a fluorescent probe, a biotin moiety, a ligand, or a drug
Man: mannose; GlcNAc, N-acetylglucosamine PEG linker: a polyethylene glycol (PEG) linker In another embodiment, the disaccharide oxazolines include, for example, those of Group II Glcβ1,4GlcNAc disaccharides depicted in FIG. 5 having the following general structure:

Group II, Glcβ1,4GlcNAc Based Oxazolines

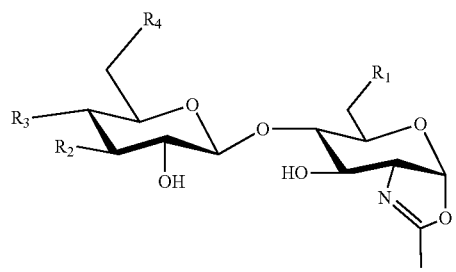

R1, R2, R3, R4=OH, N₃, PEG-linked N₃, a fluorescent probe, a biotin moiety, a ligand, or a drug
Glc: Glucose; GlcNAc, N-acetylglucosamine PEG linker: a polyethylene glycol (PEG) linker In another embodiment, the disaccharide oxazolines include, for example, those of Group III Galβ1,4GlcNAc depicted in FIG. 6 and having the following general structure:

Group III, Galβ1,4GlcNAc Based Oxazolines

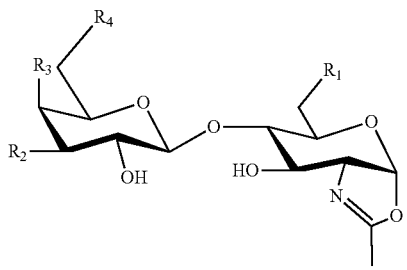

R1, R2, R3, R4=OH, N₃, PEG-linked N₃, a fluorescent probe, a biotin moiety, a ligand, or a drug
Gal, galactose; GlcNAc, N-acetylglucosamine PEG linker: a polyethylene glycol (PEG) linker The disaccharide is selectively modified with one or more azides or other entities at different sites of the disaccharide backbone.

Provided herein are antibody-conjugates wherein the conjugate is linked to an antibody azido-modified glycan oxazoline selected from the group consisting of the azido-modified glycan oxazolines of Groups I, II, and III as depicted in FIGS. 4, 5, and 6. Said antibody-conjugates may further comprise a ligand selected from drugs, toxins, labels, proteins, small molecules, thio, biotin and fluorescent label. Said antibody-drug conjugate includes, for example, a conjugate wherein the ligand is a drug and the drug to antibody ratio is 2 to 12.

It is envisioned that the disaccharide oxazolines utilized as donor substrates may further comprises an additional moiety or tag including, a therapeutic agent or drug such as for treating cancer, viral infections, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof.

In one aspect, the azido-modified oxazoline further comprises spacers. Such spacers include for example, oligoethylene spacers including polyethylene (PEG) linkers. In an embodiment, the azido-modified glycan oxazoline comprises a disaccharide core and multiple polyethylene linkers attached to the disaccharide core or other molecular linkers to forming a dendrimer.

In one aspect, for the disclosed one pot remodeling methods an endoglycosidase that has both deglycosylation and transglycosylation ability without hydrolytic activity toward the resulting transglycosylation product is utilized. In a non-limiting embodiment, the endoglycosidases may be selected from the group consisting of wild type Endo S, wild type Endo S2, wild type Endo F3 and mutants thereof. In some instances, the wild type enzyme can be coupled with another mutant enzyme of Endo-S, Endo-S2, and Endo-F3 for transglycosylation with azide-tagged glycan oxazoline, when the mutant enzyme is more efficient than the first endoglycosidase for transglycosylation.

Said endoglycosidases include endoglycosidases from *Streptococcus pyogenes*, including Endo-S2 and mutants thereof, wherein the endoglycosidases enable the transfer of an oligosaccharide (in the form of an activated sugar oxazoline) en bloc to a fucosylated or nonfucosylated GlcNAc-IgG (or an Fc fragment thereof) to form a new glycoform of IgG (or an Fc fragment thereof). (See, Sequence Listing below)

In another aspect, the present disclosure provides for Endo-S mutants that show enhanced transglycosylation efficiency and diminished or abrogated product hydrolytic activity. Mutants preferably include site-specific mutations including a mutation at Asp-233. The mutants include, but are not limited to Endo-S D233Q (SEQ ID NO: 2), D233M and D233A (SEQ ID NO: 3). Endo-S2 mutants include those with substitutions at D184 including for example D184M, D184E, D184C, D184G, D184A, D184N, D184Q, D184S and D184T. Endo F3 mutants include, for example, D165A.

In another aspect, the present invention disclosure provides for a composition comprising at least one *Streptococcus pyogenes* Endo-S Asp-233 mutant selected from the group consisting of D233Q (SEQ ID NO:2) and D233A (SEQ ID No: 3).

In an embodiment, the antibody for remodeling can be any antibody, or antibody fragment, characterized by the presence of one or more glycans that can act as substrates for deglycosylation activity through a endoglycosidases mediated reaction. Such antibodies, include for example, those antibodies having high specificity and affinity to antigens expressed on a target cell. In a non-limiting embodiment, the antigens are expressed on target cancer cells.

In an embodiment, the antibody or antibody fragment is one in which both Ig domains comprise Fc regions that are attached to a monosaccharide moiety (e.g., N-Acetylglucosamine, GlcNAc) or a trisaccharide moiety (e.g., Mannose-N-Acetylglucosamine-N-Acetylglucosamine, Man-GlcNAc-GlcNAc). The antibodies provided herein may be polyclonal or monoclonal antibodies. However, in preferred embodiments, they are monoclonal. In particular embodiments, antibodies of the present disclosure are human antibodies.

In an embodiment, the antibodies for use in the disclosed methods herein can be prepared from a commercially available therapeutic antibody (e.g., ReoPro™ (abciximab), RITUXAN™ (rituximab), ZENAPAX® (daclizumab), Simulect® (basiliximab), SYNAGIS™ (palivizumab), REMICADE® (infliximab), Herceptin® (trastuzumab), MYLOTARG® (gemtuzumab ozogamicin), Campath® (alemtuzumab), Zevalin® (ibritumomab tiuxetan), HUMIRA® (adalimumab), XOLAIR® (omalizumab), BEXXAR (tositumomab), RAPTIVA (efalizumab), ERBITUX® (cetuximab), Avastin® (bevacizumab), TYSABRI® (natalizumab), human or humanized antibodies produced via a conventional method, preferably those undergoing clinical trials.

Other monoclonal antibodies suitable for use in the methods provided herein include, but are not limited to cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, tositumomab, efalizumab, bevacizumab, panitumumab, pertuzumab, natalizumab, etanercept, IGN101®, volociximab, Anti-CD80 Mab, Anti-CD23 Mab, CAT-3888®, CDP-791®, eraptuzumab, MDX-010®, MDX-060®, MDX-07® matuzumab, CP-675.degree., 206®, CAL® SGN-30, zanolimumab, Adecatumumab®. adecatumumab, oregovomab, nimotuzumab, ABT-874® (briakinumab), denosumab, AM 108®, AMG 714®, fontolizumab, dcaclizumab, golimumab, CNTO 1275® (ustekinumab), ocrelizumab, HumaxCD20®. (ofatumumab), belimumab, epratuzumab, MLN1202®, visilizumab, tocilizumab, ocrerlizumab, certolizumab pegol, eculizumab, pexelizumab, abciximab, ranibizimumab, mepolizumab, TNX-355® and MYO-029® (stamulumab).

The present disclosure envisions modifying monoclonal antibodies associated with pathogenic infections such as, for example, bacterial, fungal, parasitic or viral infections. In a specific embodiment, the antibodies may be HIV antibodies including, but not limited to 17b, 48d, A32, C11, 2G12, F240, IgGlb12, 19e, X5, TNX-355 and F91, all of which are commercially available.

In an embodiment, the azido-tagged non-fucosylated or fucosylated antibody is modified with conjugation to other ligands to provide an antibody-conjugate. In an embodiment, the antibody-conjugate comprises a ligand selected from drugs, toxins, labels, proteins, small molecules, thio, biotin and fluorescent label. In an embodiment, the azido-tagged antibody may be modified with conjugation to other ligands by a click chemistry reaction. The clickable ligands may include one or more high-affinity M6P oligosaccharide ligands, the tri-GalNAc or other high-affinity ligands for asialoglycoprotein receptors, rhamnose or alpha-Gal moieties for binding to natural circulation antibodies, and high-affinity glycan ligands for binding to Siglecs or other glycan-binding proteins. Such click chemistry reactions are well known to those skilled in the art.

As such, the present disclosure provides a delivery device for delivering a drug or therapeutic agent having biological activity to treat a disease or disorder, the delivery device comprising: a remodeled IgG or IgG-Fc fragment having a predetermined sugar chain or sialoglycan and a therapeutic agent or drug attached to the terminal sugar residue or sialic acid. Further antibodies related to cancer or other diseases may also be remodeled for individual fit to certain receptors thereby increasing biological activity.

In an embodiment, the azido-tagged antibody further comprises alpha-Gal, rhamnose (Rh) or mannose-6-phosphate (M6P).

In yet another aspect, the present disclosure provides a substantially homogeneous preparation of core fucosylate or nonfucosylated and antibody or Fc fragment thereof having a predetermined oligosaccharide moiety, wherein the substantially homogeneous preparation is produced by any of the aforementioned methods. Also provided are compositions comprising such homogeneous preparations.

In an embodiment a method is provided for targeting degradation of extracellular and membrane associated proteins through conjugation of high affinity mannose-6-phosphate (M6P) glycan ligands to remodeled antibody molecules.

Accordingly, a one pot chemoenzymatic remodeling method is provided wherein the conjugate is a M6P glycan wherein said resulting M6P-tagged antibody targets lysosomal mediated target degradation. Said method comprises the steps for both deglycosylation and transglycosylation reactions in the one pot to provide an M6P tagged antibody, the method comprising:

(a) providing a single reactor, container, column, or pot;
(b) introducing a single endoglycosidase, such as Endo-S, wherein the endoglycosidase has both deglycosylation and transglycosylation ability;
(c) introducing an antibody for deglycosylation by the single endoglycosidase thereby providing a deglycosylated intermediate that contains at least one N-acetylglucosamine (GlcNAc) or core-fucosylated N-acetylglucosamine (Fucα1,6GlcNAc) acceptor;
(d) providing an M6P-Glycan oxazoline; and
(e) transglycosylating the M6P-Glycan oxazoline to the N-acetylglucosamine (GlcNAc) or core-fucosylated N-acetylglucosamine (Fucα1,6GlcNAc) acceptor by the single endoglycosidase to provide the M6P-tagged antibody.

In another embodiment, a one pot two enzyme chemoenzymatic remodeling method is provided wherein the conjugate is a M6P glycan and wherein said resulting M6P-tagged antibody targets lysosomal mediated target degradation. Said method comprises the steps for both deglycosylation and transglycosylation reactions in the one pot to provide an M6P tagged antibody, the method comprising:

(a) providing a single reactor, container, column, or pot;
(b) introducing a first endoglycosidase wherein the endoglycosidase has deglycosylation ability;
(c) introducing an antibody for deglycosylation by the single endoglycosidase thereby providing a deglycosylated intermediate that contains at least one N-acetylglucosamine (GlcNAc) or core-fucosylated N-acetylglucosamine (Fucα1,6GlcNAc) acceptor;
(d) providing a second endoglycosidase and a M6P-Glycan oxazoline; and
(e) transglycosylating the M6P-Glycan oxazoline to the N-acetylglucosamine (GlcNAc) or core-fucosylated N-acetylglucosamine (Fucα1,6GlcNAc) acceptor by the second endoglycosidase to provide the M6P-tagged antibody.

In an embodiment, the two enzyme method may utilize wild type Endo S for the deglycosylation step and the S2 mutant (D184M) for the transglycosylation method.

Figure 8:
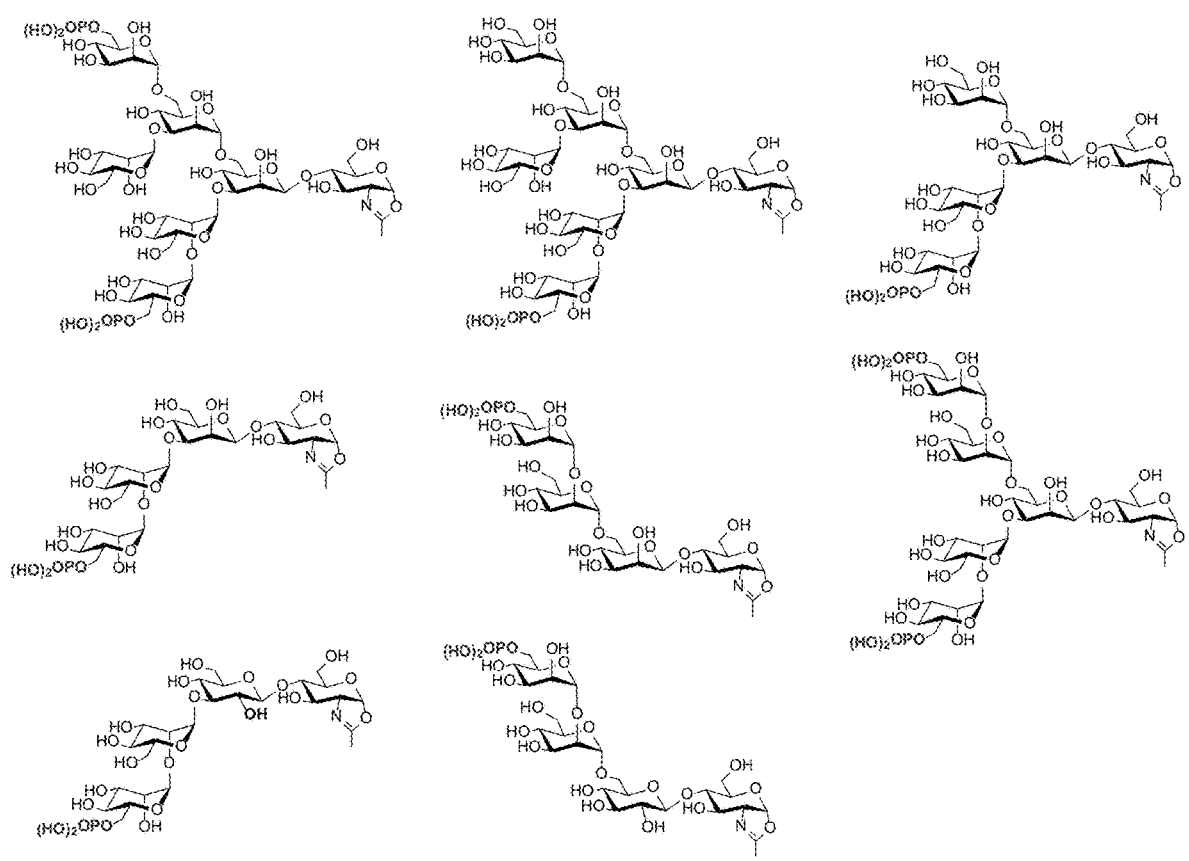
FIG. 8. Structures of selected M6P glycan oxazolines.

In an non-limiting embodiment, the M6P-Glycan oxazoline is selected from the group consisting of the phosphorylated glycan oxazolines as depicted in FIG. 8.

In an embodiment, said M6P-tagged antibodies target binding to an extracellular protein. In another embodiment, said M6P-tagged antibodies target binding to a membrane bound protein. Said membrane bound proteins include for example, is HER2 or EGFR.

In a still further aspect, the present invention provides for a method of treating a disease or disorder comprising administration of a remodeled antibody generated using the one pot chemoenzymatic remodeling methods disclosed herein and having a desired glycosylation state form in an amount sufficient to modulate biological activity in the treated subject.

In further embodiments, pharmaceutical compositions comprising a remodeled antibody generated using the one pot chemoenzymatic remodeling methods disclosed herein and a pharmaceutical acceptable carrier are provided. The antibodies exhibit properties for use as therapeutic agents, e.g. in the treatment of cancer in a subject for example. Such pharmaceutical compositions comprise a therapeutically effective amount of one or more of a remodeled antibody dissolved or dispersed in a pharmaceutically acceptable carrier. The preparation of a pharmaceutical composition that contains at one or more a remodeled antibody and optionally an additional active ingredient will be known to those of skill in the art in light of the present disclosure, as exemplified by Remington's Pharmaceutical Sciences, 18th Ed. Mack Printing Company, 1990. For human administration, it will be understood that preparations should meet sterility, pyrogenicity, general safety and purity standards as required by FDA Office of Biological Standards or corresponding authorities in other countries. Preferred compositions are lyophilized formulations or aqueous solutions.

As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it needs to be sterile for such routes of administration as injection. A remodeled antibody (and any additional therapeutic agent) can be administered by any method or any combination of methods as would be known to one of skill in the art (see, for example, Remington's Pharmaceutical Sciences, 18th Ed. Mack Printing Company, 1990, incorporated herein by reference). Parenteral administration, in particular intravenous injection, is most commonly used for administering protein or polypeptide molecules such as a remodeled antibody.

Any of the remodeled antibodies derived using the one pot methods disclosed herein, may be used in therapeutic methods as described herein. For use in the therapeutic methods described herein the remodeled antibody is formulated, dosed, and administered in a fashion consistent with good medical practice. Factors for consideration in this context include the particular disorder being treated, the particular subject being treated, the clinical condition of the subject, the cause of the disease or condition, the site of delivery of the agent, the method of administration, the scheduling of administration, and other factors known to medical practitioners or those of skill in the art.

For the treatments, the appropriate dosage of the remodeled antibodies (when used alone or in combination with one or more other additional therapeutic agents) will depend on the type of disease to be treated, the route of administration, the body weight of the patient, the severity and course of the disease, whether the remodeled antibody is administered for preventive or therapeutic purposes, previous or concurrent therapeutic interventions, the patient's clinical history and response to the remodeled antibody, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

In another embodiment, the provided delivery device is designed to deliver a detectable label or marker to a targeted antigen for diagnostic and prognostic uses. Said a delivery device comprises a remodeled IgG or IgG-Fc fragment having a predetermined sugar chain and the detectable label or marker attached to the remodeled antibody. A "detectable label" or a "marker" refers to a composition that is detectable by spectroscopic, photochemical, biochemical, immunochemical, radioactive or chemical means. For example, a useful label includes $^{32}P$, $^{35}S$, fluorescent dyes, electron-dense reagents, enzymes (e.g., enzymes that are generally used in ELISA), biotin-streptavidin, digoxigenin, hapten, proteins or nucleic acid molecules with a sequence complementary to a target. The detectable label often generates a measurable signal, e.g., a radioactive signal, a color signal or a fluorescent signal, which is usable to quantify an amount of the detectable moiety that binds to the target antigen. Quantification of the signal may be accomplished by, for example, scintillation counting, density gauge, flow cell analysis, ELISA, or direct analysis by mass spectroscopy. Those skilled in the art are familiar with techniques and detection means for a label compound of interest. These techniques and methods are conventional and well known in the art. In another aspect of the embodiment, an article of manufacture (e.g., a kit) containing materials useful for the treatment or diagnosis of diseases or disorders as described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle).

The label or package insert indicates that the composition is used for treating the condition of choice. The article of manufacture may comprise a container with a composition contained therein, wherein the composition comprises a remodeled antibody Kits in certain embodiments may further comprise a package insert indicating that the compositions can be used to treat a particular condition. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are included to demonstrate preferred embodiments of the present disclosure. It should be appreciated by those of skill in the art that the techniques disclosed in the examples which follow represent techniques discovered by the inventor to function well in the practice of embodiments of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1

As described below a systematic investigation was done of the selectively modified di-, tri- and tetrasaccharide oxazolines and their donor substrate specificity of a series of endoglycosidase was examined and their mutants in glycan remodeling of therapeutic antibodies. The minimal azide-modified disaccharide structures that could serve as donor substrates of different endoglycosidases for transglycosylation on antibodies was discovered. Since the glycoengineered antibodies carrying the truncated and modified N-glycans become resistant to hydrolysis by the endoglycosidases and their mutants, the discovery led to a simple, "one-pot" glycan remodeling method that combines the antibody deglycosylation and transglycosylation reactions in one reactor without the need to separate the deglycosylation intermediate and the enzyme.

The data demonstrate that the azide-tagged antibodies are remarkably efficient for producing homogeneous and site-specific antibody-drug conjugates with well-defined antibody-drug ratios (DARs). This observation provides a general method for producing antibody-drug conjugates (ADCs) using any given antibody, linker, and payload. This method is also particularly useful for fluorescent labeling and introduction of any special ligands such as glycan ligands for targeting. This site-specific conjugation method is also demonstrated to be applicable for attaching high-affinity mannoe-6-phosphate (M6P) oligosaccharide ligands to antibody for targeted protein degradation. This site-specific conjugation method is applicable for attaching any specific glycan ligands for targeting lectins and other glycan-binding proteins, serum antibodies.

A general method to introduce azido-tags site-selectively at the Fc glycans of antibodies. For the single enzyme one-pot method, a wild type endoglycosidase such as Endo-S2 is used for both deglycosylation and transglycosylation to product the azide-tagged antibody (FIG. 1). This method is enabled by the discovery that such endoglycosidase can use the modified disaccharide oxazoline for transglycosylation but has low or no hydrolytic activity on the transglycosylation product. For a two enzyme one-pot strategy, the commercial antibody was firstly treated with a wild type endoglycosidase, such as Endo-S, then the transglycosylation is carried out by another endoglycosidase such as Endo-S2 or its mutants that have higher transglycosylation activity than the first endoglycosidase (FIG. 2). In the above one-pot methods, the oxazolines may be pre-modified with an entity other than an azide moiety, including a drug or a ligand for direct transfer. FIG. 3 demonstrates click conjugation of drug or other entities to the azide-tagged antibodies.

General structures of the modified glycan oxazolines. A systematic investigation of the selectively modified glycan oxazolines was performed and the azide-modified disaccharides as the minimal structures that could serve as donor substrates for modification of antibodies with different endoglycosidases was determined. Such glycan oxazolines are, for example, those selected from the structures of FIGS. 4-6. Here the core mannose can be modified with oligoethylene spacers to introduce varied number of azido-tags; the oligoethylene spacers can be located at different positions of the mannose residue; the length of the oligoethylene spacers can be selected with different degrees of polymerization; besides the linear spacers, the branched scaffolds extended with oligoethylene spacers can be also used; other functional groups such as terminal alkyne, dibenzoazacyclooctyne (DBCO), bicyclo[6.1.0]nonyne (BCN), tetrazine, trans-cyclooctene (TCO), cyclopropene can be also introduced to the glycan oxazolines; up to three different spacers can be introduced at different positions; the core β-mannose can be replaced with β-glucose to develop "hydrolysis-resistant" oxazolines, and all the modifications mentioned above are applicable to the glucose-derived structures; the glycans are not limited to disaccharides, selectively modified tri- and tetrasaccharide oxazolines can be also included for the transglycosylation.

Chemical synthesis of the azido-tagged disaccharides. Azide-tagged disaccharide oxazolines or their derivatives can be synthesized by different synthetic routes. The following description just show some typical examples, which does not mean the only method for preparation.

Figure 9:
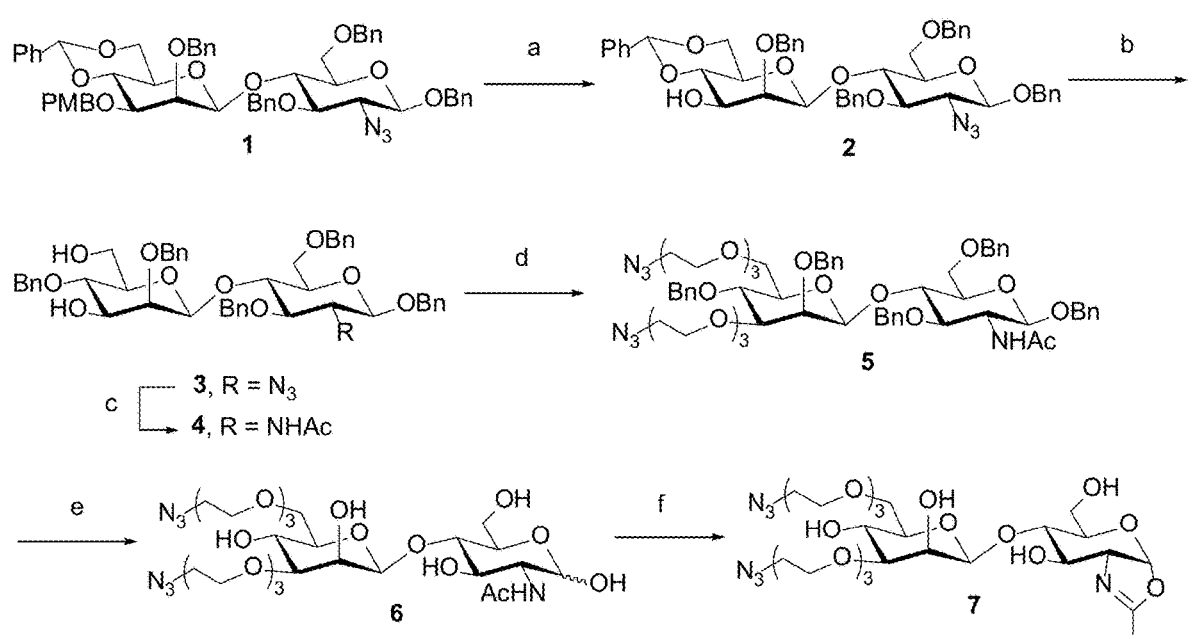
FIG. 9. Synthesis of $2N_3$-tagged disaccharide oxazoline 7. Reagents and conditions: (a) DDQ, $CH_2Cl_2/H_2O$, 0° C.~RT, 90%; (b) $BH_3$·THF, $Bu_2BOTf$, $CH_2Cl_2$, 0° C., 94%; (c) AcSH, pyridine/$CHCl_3$, RT, 82%; (d) $N_3(CH_2CH_2O)_3Ts$, NaH, DMF, 0° C.~RT, 78%; (e) $NaBrO_3$, $Na_2S_2O_4$, EtOAc/$H_2O$, RT, 65%; (f). DMC, $Et_3N$, $H_2O$, 0° C., 90%.

While it has been shown that smaller synthetic disaccharide oxazolines could serve as substrates of Endo-A and Endo-M for transglycosylation, (Y Zeng et al. Chem Eur J 2006 12:3355-3364) it is not clear whether those antibody-specific endoglycoylases and their mutants can recognize the smaller substrates for transglycosylation using antibodies as acceptors. To test this, an attempt was made to synthesize a series of azide-tagged disaccharide oxazolines. In 2020, it was reported the synthesis of a PEG-modified core disaccharide oxazoline and its transglycosylation with a model protein as the acceptor. (Goto et al, 2020 Tetrahedr Lett 61: 151475) Considering the flexibility and solubility of PEGs, it was decided to introduce azido groups with PEG-derived scaffolds. Firstly, the disaccharide with two azido groups was designed, in which the PEG-linkers resembled the natural glycan branches so that it might be recognized by the endoglycosidases (FIG. 9). Starting from the known disaccharide 1 (H. Ochiai et al., 2008 J Am Chem Soc 130:13790-13803) selective removal of the PMB group with DDQ afforded compound 2 in 90% yield, which was transformed into compound 3 with two free OH upon regioselective ring-opening reaction. After the reduction of azido group to acetamido group with AcSH, the azido tags were introduced in 78% yield by the coupling of compound 4 and $N_3(CH_2CH_2O)_3Ts$ with NaH as the base. Next, in order to selectively remove the benzyl groups in the presence of azides, a biphasic oxidative condition ($NaBrO_3/Na_2S_2O_4$) was adopted, (M Niemietz et al., 2011 47:10485-10487) which furnished the desired free glycan 6 in 65% yield. Finally, oxazoline formation was achieved in a single step by treatment with an excess amount of 2-chloro-1,3-dimethyl-imidazolinium chloride (DMC) and TEA in water (MNouchi et al., 2009 J Org Chem 74:2210-2212), and compound 7 was obtained in 90% yield.

Figure 10:
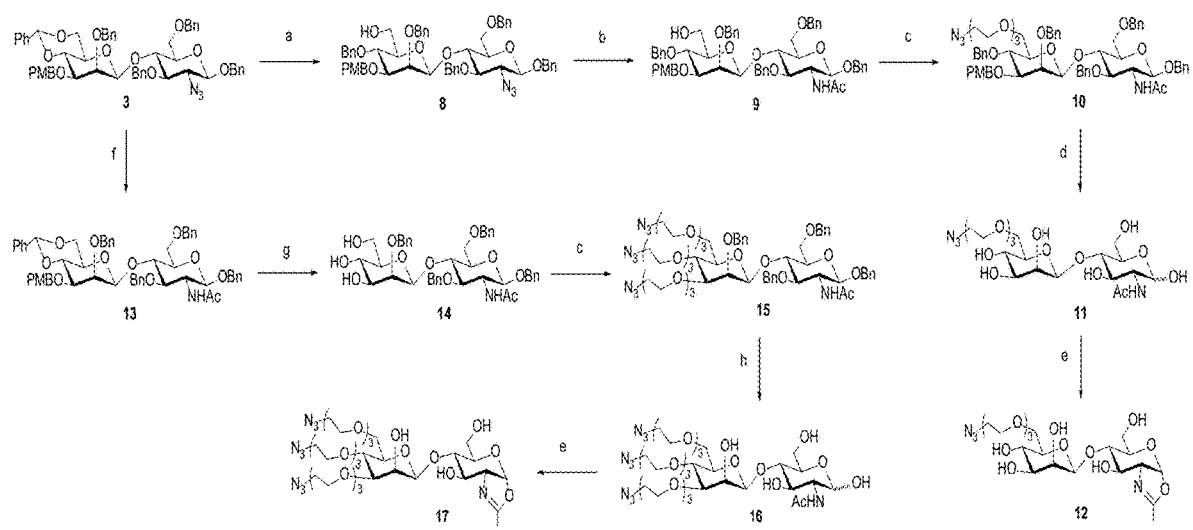
FIG. 10. Synthesis of $1N_3$— or $3N_3$-tagged disaccharide oxazolines 12 and 17. Reagents and conditions: (a) $BH_3$·THF, $Bu_2BOTf$, $CH_2Cl_2$, 0° C., 91%; (b) AcSH, pyridine/$CHCl_3$, RT, 84%; (c) $N_3(CH_2CH_2O)_3Ts$, NaH, DMF, 0° C.~RT, 10, 89%, 15, 73%; (d) $NaBrO_3$, $Na_2S_2O_4$, EtOAc/$H_2O$, RT, 90%; (e) DMC, $Et_3N$, $H_2O$, 0° C., 12, 90%, 17, 85%; (f) AcSH, pyridine/$CHCl_3$, 60° C., 85%; (g) TFA, $CH_2Cl_2$, −20° C.-0° C., 82%; (h)Pd/C, $H_2$, HCl (aq), THF/$H_2O$, then $TfN_3$, $K_2CO_3$, $CuSO_4$, $CH_2Cl_2$/MeOH/$H_2O$, RT, 66%.

Next, the disaccharides were synthesized with one or three azido groups (FIG. 10). The 6-position of the mannose residue was selected for the introduction of a single azido-ended PEG linker. Regioselective ring-opening of 3 smoothly exposed the hydroxyl to obtain disaccharide 8. After the reduction of azido group to acetamido group, the PEG linker was introduced in high yield to afford 10. Selective debenzylation under the oxidative condition proved to be efficient, giving the free disaccharide 11 in 90% yield, which was converted to oxazoline 12 after treatment with DMC. In parallel, the synthesis of three azido-tagged disaccharide also started from 3. Upon the reduction of azido group to acetamido group, the benzylidene and PMB groups were simultaneously removed under acidic condition (H. Ochiai et al., 2008 J Am Chem Soc 130:13790-13803), which afforded 14 with three free OH. Next, the PEG linkers were introduced at 3-, 4- and 6-positions of the mannose residue to yield 15. Following the same debenzylation condition, it was found that the reaction proceeded very fast, but the desired product was isolated in low yield along with some decomposed structure as monitored by ESI-MS. It was possible that the increase of PEG component resulted in higher water solubility, thus the partially deprotected intermediate migrated to the aqueous phase and directly interacted with the free radical (M Adinilfi et al. 1999, Tetrahedr Lett 40:8439-8441) which led to rapid reaction and undesired products. Instead, a two-step deprotection was applied. (H. Ochiai et al., 2008 J Am Chem Soc 130:13790-13803_First, the benzyl groups in 15 were removed by catalytic hydrogenation. Under this condition, the azido groups were simultaneously reduced to amino groups, which were then transformed back to azido functionality by the copper-catalyzed diazo transfer reaction, (PT Nyffeler et al., 2002 J Am Chem Soc 124:10773-10778) giving 16 in 66% yield in two steps. Finally, standard oxazoline formation provided 17 in excellent yield.

Figure 11:
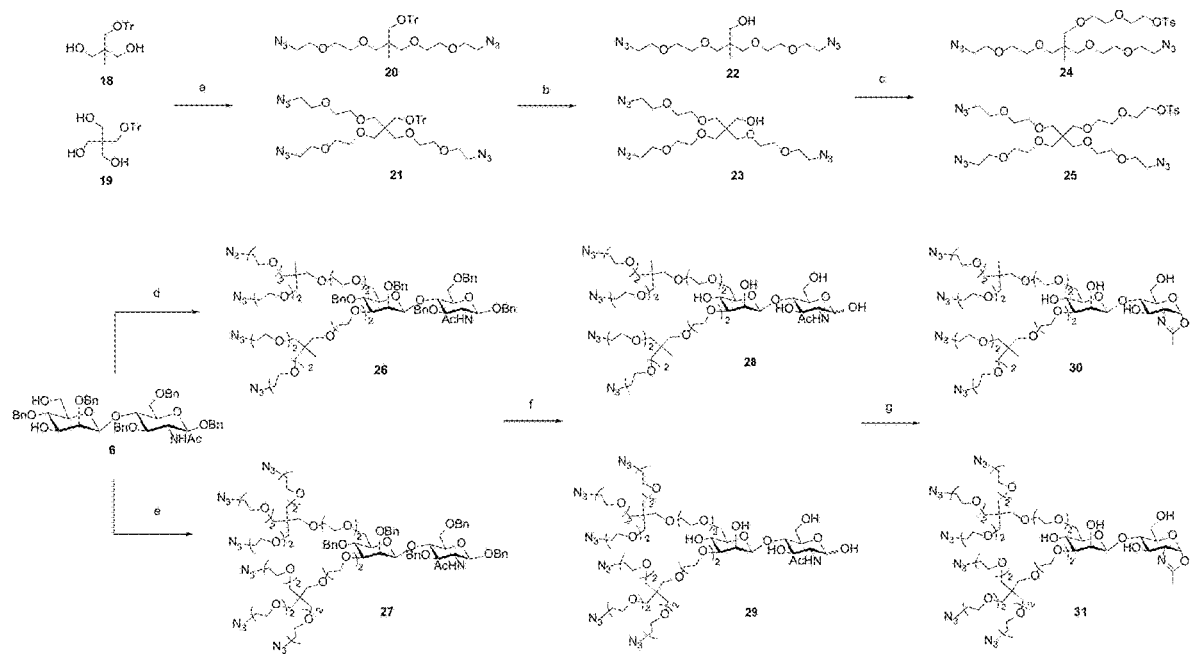
FIG. 11. Synthesis of $4N_3$— or $6N_3$-tagged disaccharide oxazolines 30 and 31. Reagents and conditions: a) $N_3(CH_2CH_2O)_2Ts$, NaH, DMF, 0° C.~RT; b) TsOH, MeOH, 60° C., 20, 72% for 2 steps, 21, 54% for 2 steps; c) $TsO(CH_2CH_2O)_2Ts$, NaH, DMF, 0° C.~RT, 22, 85%, 23, 72%; d) 22, NaH, DMF, 0° C.~RT, 78%; e) 23, NaH, DMF, 0° C.~RT, 74%; f) Pd/C, $H_2$, HCl (aq), THF/$H_2O$, then $TfN_3$, $K_2CO_3$, $CuSO_4$, $CH_2Cl_2$/MeOH/$H_2O$, RT, 28, 67%, 29, 59%; g) DMC, $Et_3N$, $H_2O$, 0° C., 30, 89%, 31, 84%.

Previous studies showed that ADCs with higher DARs tended to provide increased potency. (RP Lyon et al., 2015 Nat Biotechnol 33:733-735) In a handful of cases a DAR as high as 8 has safely been achieved through the use of hydrophilic linker-payloads, as exemplified with the clinically approved Enhertu® and Trodelvy®. (A Bardia et al, 2019 N Engl J Med 380:741-75; W Viricel et al., 2019 Chem Sci 10:4084-4053). To equip antibodies with more biorthogonal tags, the disaccharides were designed carrying four or six azido groups. The synthesis commenced with the branched scaffolds (FIG. 11). First, the diol 18 (B Linclau et al., 2012 Angew Chem Int Ed 51:1232-1235) and triol 19 (2008, Chem Lett 31:440-441) were extended by an azido-ended linker, which respectively furnished compound 22 and 23 after the removal of the trityl group. The exposed OH in 22 and 23 was further extended with a bis-tosyl linker to give compound 24 and 25, respectively, which were ready for conjugation. Next, starting from the same precursor, compounds 26 and 27 were readily obtained by the coupling of 6 with scaffold 24 and 25, respectively, the overall yields were both satisfactory. Finally, after the two-step deprotection and oxazoline formation, compounds 30 and 31, which carry four and six azido groups, respectively, were obtained in moderate yields.

Figure 12:
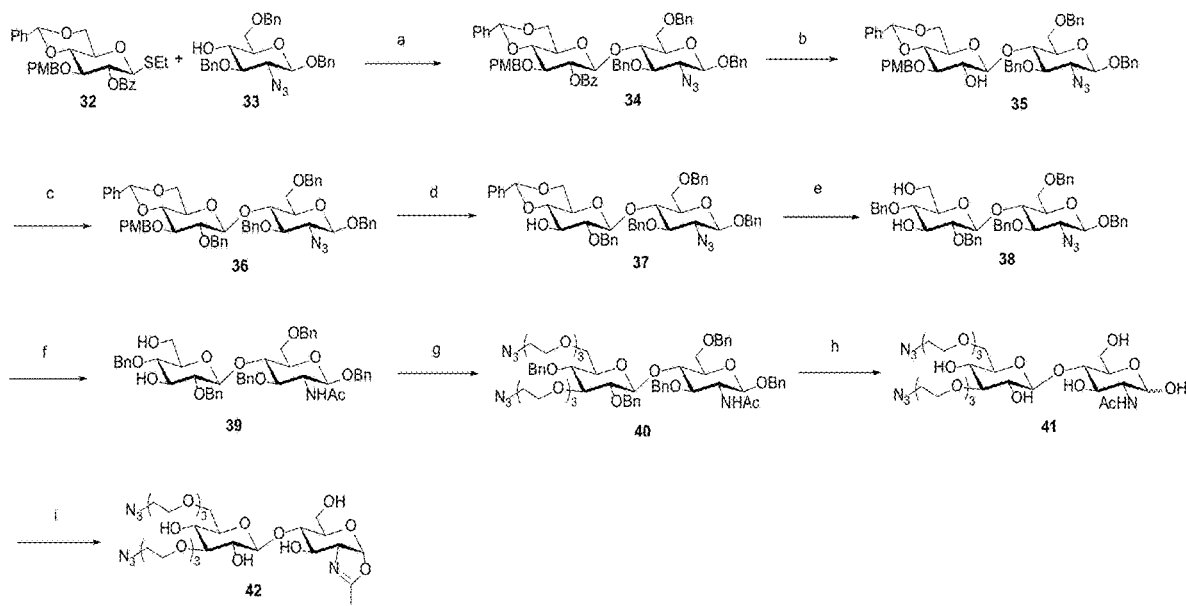
FIG. 12. Synthesis of $2N_3$-tagged Glc-GlcNAc disaccharide oxazoline 42. Reagents and conditions: a) NIS, AgOTf, $CH_2Cl_2$, 4 Å MS, −20° C., 73%; b) MeOH, MeONa, 50° C.; c) NaH, DMF, BnBr, 0° C.~RT; d) DDQ, $CH_2Cl_2/H_2O$, 0° C.~RT, 90%; e) $BH_3$·THF, $Bu_2BOTf$, $CH_2Cl_2$, 0° C., 74% for 3 steps; f) AcSH, pyridine/$CHCl_3$, RT, 85%; g) $N_3(CH_2CH_2O)_3Ts$, NaH, DMF, 0° C.~RT, 82%; h) $NaBrO_3$, $Na_2S_2O_4$, EtOAc/$H_2O$, RT, 67%; i) DMC, $Et_3N$, $H_2O$, 0° C., 95%.

Previous studies showed that modifications of the oxazoline donors may not affect the transglycosylation activities of endoglycosidases. To avoid the construction of the challenging β1,4-mannosidic bond, the β-D-Man moiety was replaced with β-D-Glc to synthesize a Glcβ1,4GlcNAc disaccharide (FIG. 12). Thus starting from the known building block 32 and 33, traditional glycosylation condition (NIS/AgOTf) afforded the desired disaccharide 34 in 73% yield with exclusive β isomer. Notably, this step could be performed in gram scale without loss of stereoselectivity. Then standard debenzylation and benzylation, followed by removal of PMB gave compound 37 in 74% yield over three steps. Finally, the Glc-GlcNAc oxazoline 42 was obtained following the same procedures as described for the synthesis of 7.

Figure 51:
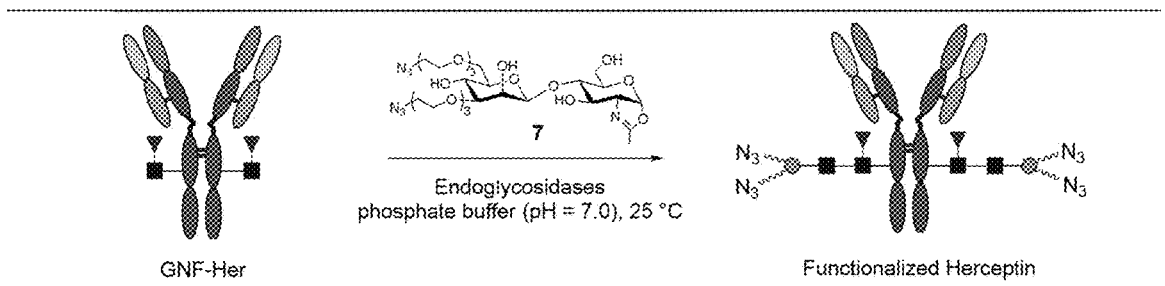
FIG. 51 Screening of the transglycosylation conditions.

Evaluation of substrate specificity of different endoglycosidases toward the synthetic azido-tagged sugar oxazolines. With the oxazolines in hand, the transglycosylation conditions were screened with different endoglycosidases. Compound 7 was selected as the glycosyl donor, and trastuzumab, an anti-Her2 antibody (Herceptin), was used as a model mAb to examine the potential of the synthetic disaccharides for glycan remodeling of antibodies (FIG. 51). The reaction was started from wild-type Endo S that has been found to be highly active and specific for Fc deglycosylation of intact IgG antibodies. (W Huang et al, 2012 J Am Chem Soc 134:12308-12318; M Collin et al., 2001 EMBO J 20:3046-3055) With a catalytic amount of enzyme (0.2% w/w), no transglycosylation was observed. Increasing the amount of enzyme (1%, w/w) turned out to accelerate this procedure, but the yield was only moderate even after pushing with additions of excess sugar oxazolines. Nevertheless, the product, once formed, was not hydrolyzed by wild type Endo S either, probably due to its unnatural structure. The mutant, Endo S-D233Q, which could efficiently transfer large bi-antennary glycan oxazoline to antibody (W Huang et al, 2012 J Am Chem Soc 134:12308-12318) was not efficient either, giving 15% yield even when a relatively large amount of enzyme (10%, w/w) was used. Surprisingly, another endoglycosidase from the *Streptococcus pyogenes* of serotype M49, namely Endo S2, (J Sjogren et al., 2013 Biochem J 455:107-118) exhibited excellent activity towards this azido-tagged disaccharide, with a catalytic amount of enzyme (0.1%~0.2% w/w), the reaction could reach completion within 1 hour. Marginal hydrolysis of product was observed under this condition, which allowed the accumulation of product. Considering the potent transglycosylation activity, together with its efficient hydrolysis of the complex-type N-glycans from the commercial antibody, Endo S2 provided a practical "one-pot" strategy for remodeling of heterogeneous glycoforms of antibody to produce a homogeneous structure. Endo S2 mutant (D184M) was also tested, a glycosynthase with broad substrate specificity and diminished hydrolytic activity (Y Zeng et al, 2006 Chem Eur J 12:3355-3364), and found it exhibited similar activity as compared with wild-type Endo S, relatively large amount of enzyme (3%~5%) was needed for efficient transglycosylation. In addition to the four enzymes, several other endoglycosidases were also tested. Endo F3, which prefers to recognize the core-fucosylated complex-type N-glycans and has been used for remodeling of both Fab and Fc glycans of therapeutic antibody, (JP Giddens et al., 2018 Proc Natl Acad Sci USA 115:12023-12027) didn't show any activity towards this azido-tagged disaccharide. As for Endo A, Endo D and Endo CC that prefer non-fucosylated substrates, the GNF-Herceptin was treated with a fucosidase (BfFucH) to produce an afucosylated Fc glycoform. The results showed that Endo D exhibited some transglycosylation activity, but only transitional product was observed. Endo A or Endo CC didn't afford any product even if a large amount of enzyme (10%, w/w) was used.

Figure 13:
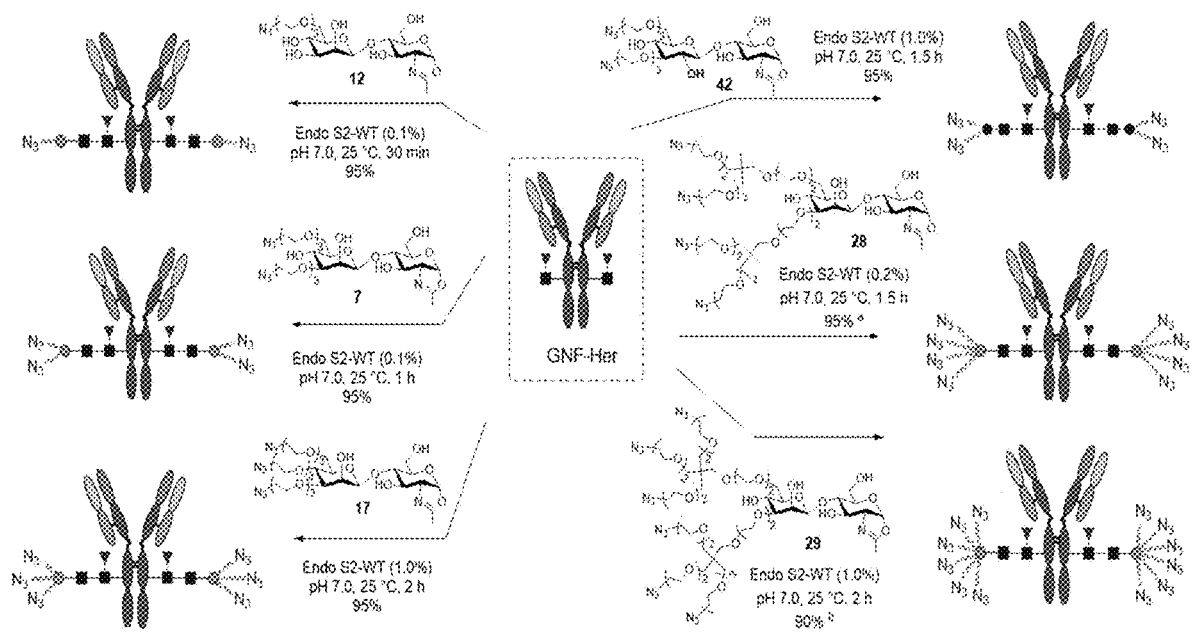
FIG. 13. Transglycosylation with different azido-tagged disaccharide oxazolines. Reagents and conditions: The reactions were conducted with 20 eq of oxazolines in PBS buffer at 25° C.; a. one additional potion of oxazoline (10 eq) was added after 1 hour; b. three more potions of oxazoline (10 eq) were added every 30 min.

With the optimized condition, the transglycosylation was tried using the other disaccharides (FIG. 13). The results showed that wild-type Endo S2 worked well with all the glycosyl donors. With a catalytic amount of enzyme (0.1%~1.0%), the reaction smoothly afforded the corresponding product. Notably, one potion of oxazoline was enough to achieve complete conversion for the disaccharides carrying one to three azido groups, because compounds 7 and 12 were such good substrates that the transglycosylation could be finished within 1 hour, whereas compounds 17 and 42 were resistant to hydrolysis and as a result, relatively larger amounts of enzyme but no additional oxazoline was needed. However, for the disaccharide carrying four (28) or six (29) azido groups, additional potion of oxazoline was necessary to drive the reaction to completion due to the hydrolytic activity of Endo S2 towards oxazoline donors, but the excess glycan oxazoline could be recovered during the protein A purification in the form of free oligosaccharide, which was readily converted into the glycan oxazoline in a single step with DMC/Et$_3$N, thus permitting the recycling of glycan oxazoline for transglycosylation.

Figure 14:
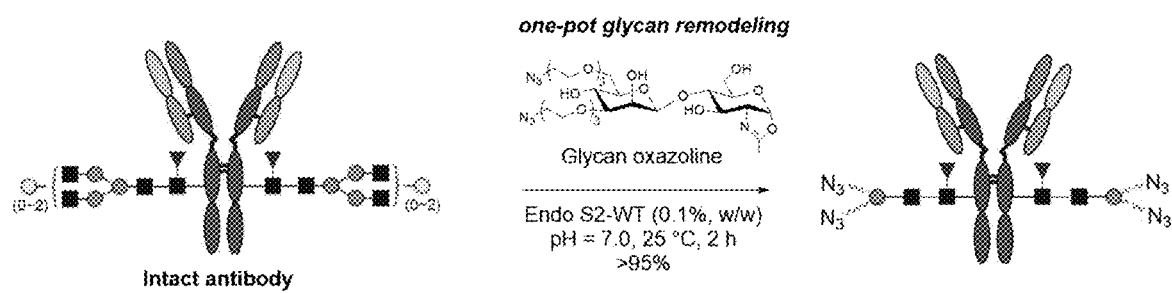
FIG. 14 One-pot transglycosylation of intact antibody with azido-tagged disaccharide oxazoline.

Next, the possibility was examined of remodeling antibody glycosylation in a one-pot fashion, thus a mixture of the commercial Herceptin, glycan oxazoline 7, and wild-type Endo S2 was incubated in PBS buffer at room temperature and the reaction was monitored by LC-MS analysis. As expected, the Endo S2-catalyzed deglycosylation of Herceptin took place rapidly and was completed within 5 min under the reaction condition. Then the transglycosylation product was steadily formed over the time without apparent hydrolysis, reaching more than 95% yield within 2 h (FIG. 14). Notably, the one-pot approach described here was able to transform the heterogeneous glycoforms into homogeneous and functionalized glycan without the need of separating the deglycosylated intermediate or changing the enzyme. Furthermore, it was confirmed that if immobilized wild-type Endo S2 (T Li et al., 2018 Carbohydr Res 458-459, 77-84) was used as the catalyst, upon the completion of the transglycosylation, the desired antibody could be readily obtained by filtration and buffer exchange, which would be practical for industrial manufacture.

Figure 15:
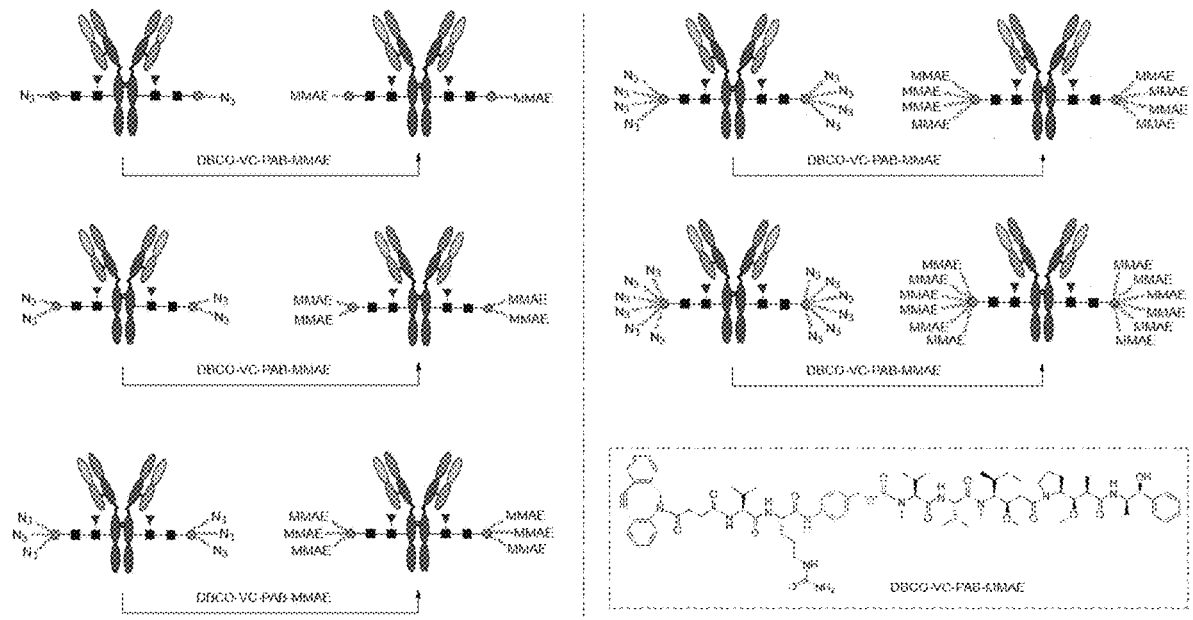
FIG. 15. Preparation of structurally defined ADCs by click chemistry. Reagents and conditions: The azido-tagged antibodies (final concentration 2 mg/mL) were incubated with DBCO-VC-PAB-MMAE (5.0 eq/per azido group) in DMSO/50 mM PB (3:7, v/v) at room temperature for 8~24 h.
Figure 16:
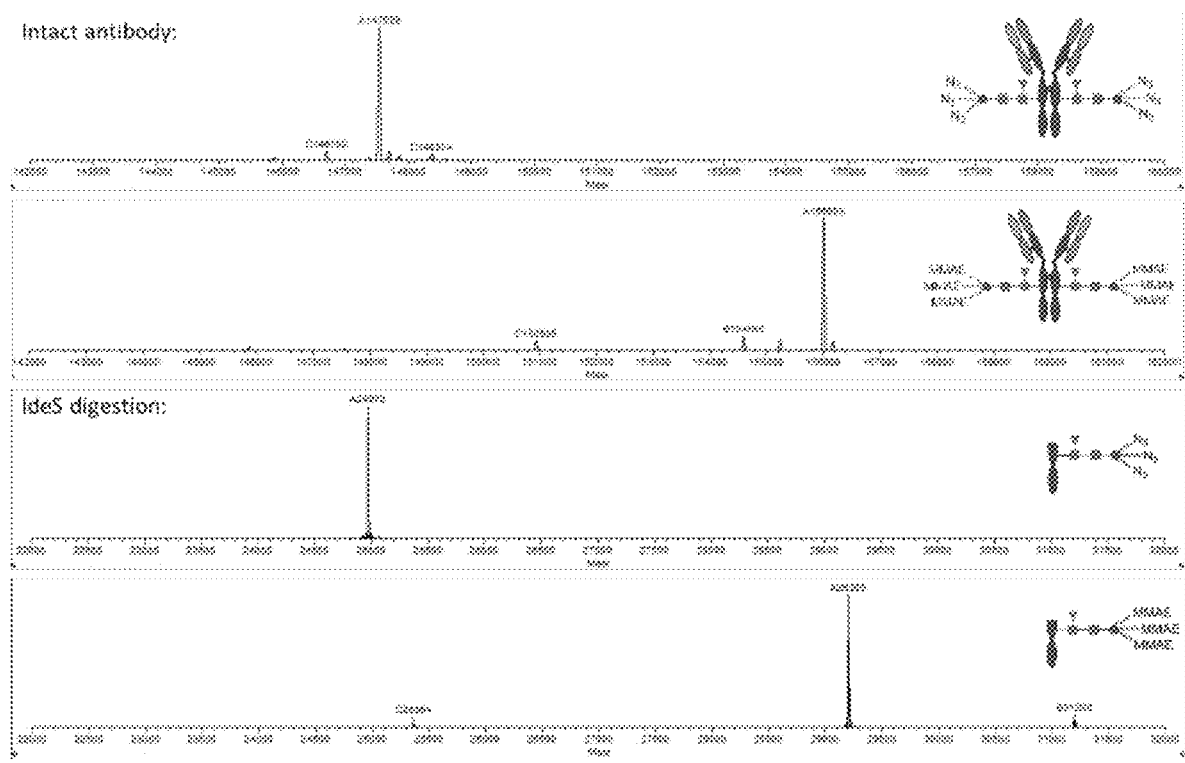
FIG. 16. Representative LC-MS analysis of ADC structures.

Site-specific conjugation with the azido-tagged antibodies. With these azido-tagged antibodies in hand, the click chemistry was used to make ADCs, using Monomethyl auristatin E (MMAE) as a model warhead, which has been used for making the FDA-approved ADCs (FIG. 15). The dibenzoazacyclooctyne (DBCO)-ended MMAE derivative with a cleavable dipeptide linker was incubated with the azido-tagged antibodies, and the reactions were monitored by LC-MS. It was found that the click chemistry gradually afforded the desired compounds. Taking the reaction between 6N$_3$-modified Herceptin and DBCO-VC-PAB- MMAE as an example. All the six sites were conjugated with drugs within 20 hours as indicated by LC-MS (FIG. 16). To further verify that the drugs were specifically conjugated to the Fc domain, the product was digested with the protease IdeS followed by LC-MS analysis. The results showed that the shift of molecular weight was consistent with the attached linkers (29205-24972=4233=1411*3), thus confirming the structure of the product.

Finally, the cancer cell killing potency of the ADCs was examined with different drug-antibody ratios (DARs). Two breast-cancer cell lines expressing high (BT474) and low (T47D) levels of HER2 were used. The results showed that the ADCs had dramatically increased cytotoxicity with the increase of DARs in HER2 overexpressed cell line (BT474). However, no significant trends of cell killing were observed in antigen negative cell line (T47D), indicating the high selectivity of the ADCs for the target cells.

Figure 17:
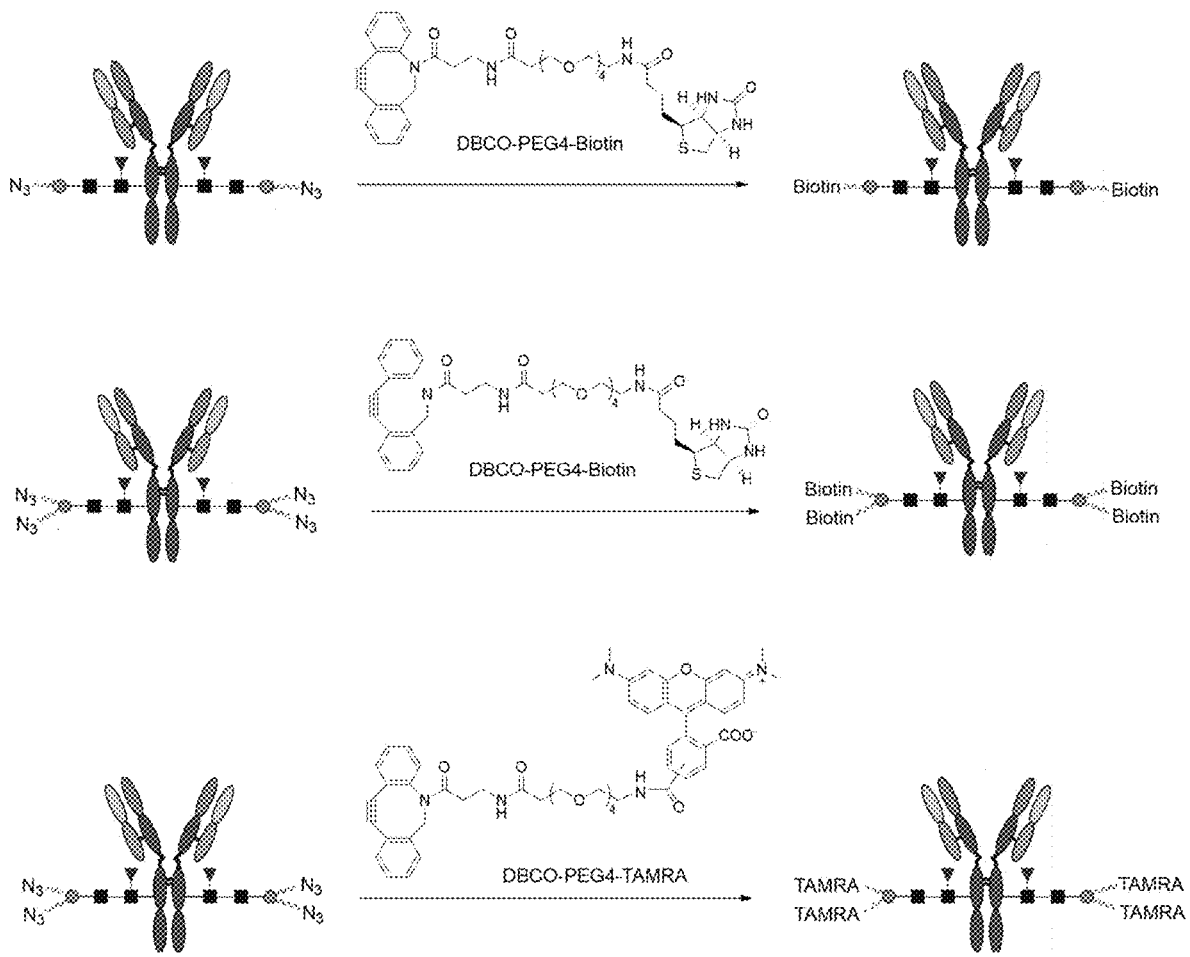
FIG. 17. Site-specific labeling of antibodies with biotin or fluorescent groups.

Site-specific labeling of antibodies with biotin or fluorescent groups. Functionalized antibodies have been used extensively for diagnostics, in vivo imaging, therapy and as a tool for molecular biology, inspiring the development of methods for precise engineering of intact antibodies. Conventional methods such as global lysine labeling with N-hydroxysuccinimide (NHS) esters (aa Wakankar et al., 2010 Bioconjug Chem 21:1588-1595) or by cysteine conjugation via reduction of disulfide bonds and reaction with maleimides (SO Doronina et al., 2003 Nat Biotechnol 21:778-784), lack control of attachment sites and stoichiometry thus produce nonhomogeneous conjugates. With the azido-tagged antibodies as a universal platform, site-specific labeling of intact antibodies turned out to be straightforward. A number of dibenzoazacyclooctyne (DBCO)-ended probes carrying different functional groups including biotin and rhodamine were incubated with the azido-tagged antibodies, and the reactions were monitored by LC-MS. It was found that the click chemistry gradually afforded the desired compounds (FIG. 17).

Figure 18:
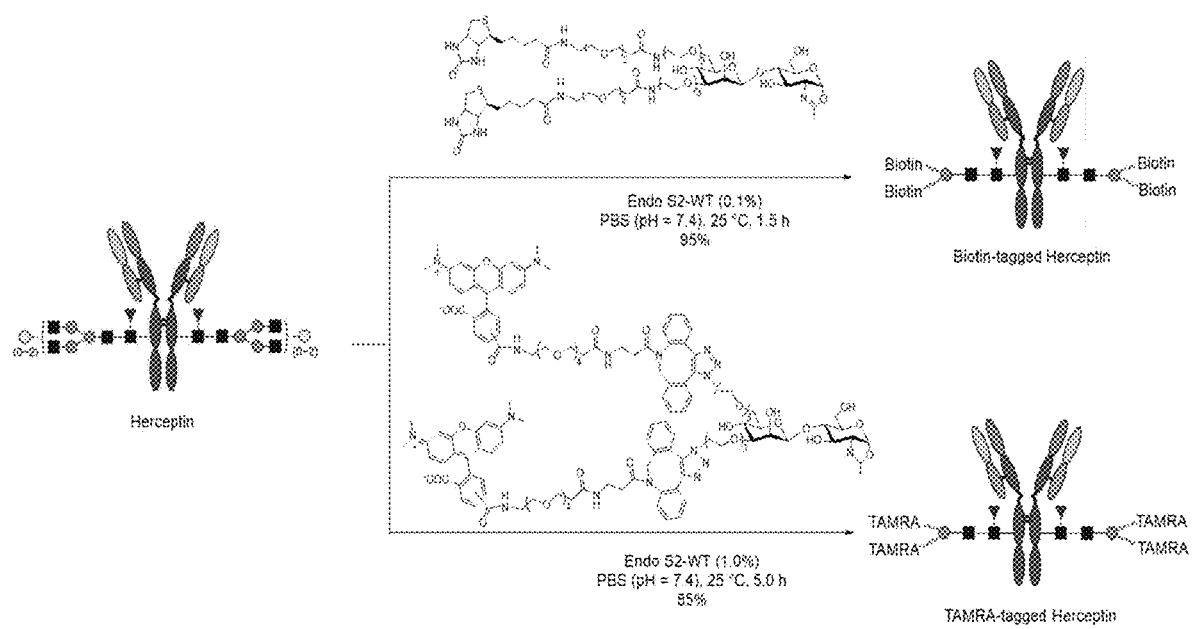
FIG. 18. One-step labeling of commercial antibodies with biotin or fluorescent groups.

Encouraged by the one-pot remodeling of intact antibody with azido-tagged disaccharide (FIG. 14) and the relaxed substrate specificity of wild-type Endo S2, it was then investigated whether one could directly transfer more complex structure, such as biotin- or fluorophore-tagged disaccharide oxazoline to intact antibody with Endo S2, in this way the commercial antibodies could be labeled in one step. To this end, biotin or TAMRA was introduced to the disaccharide, either via amine coupling reaction or click chemistry, and it was found that the modified disaccharides could still serve as good substrates of Endo S2. The biotinylated disaccharide was transferred to intact antibody in 95% yield within 1.5 h with a catalytic amount of enzyme (0.1%, w/w), and the TAMRA-tagged disaccharide could afford about 85% of product if additional potions of oxazoline were added (FIG. 18). Taken together, the chemoenzymatic remodeling method described here showed great potential for one-step labeling of intact antibody.

Figure 19:
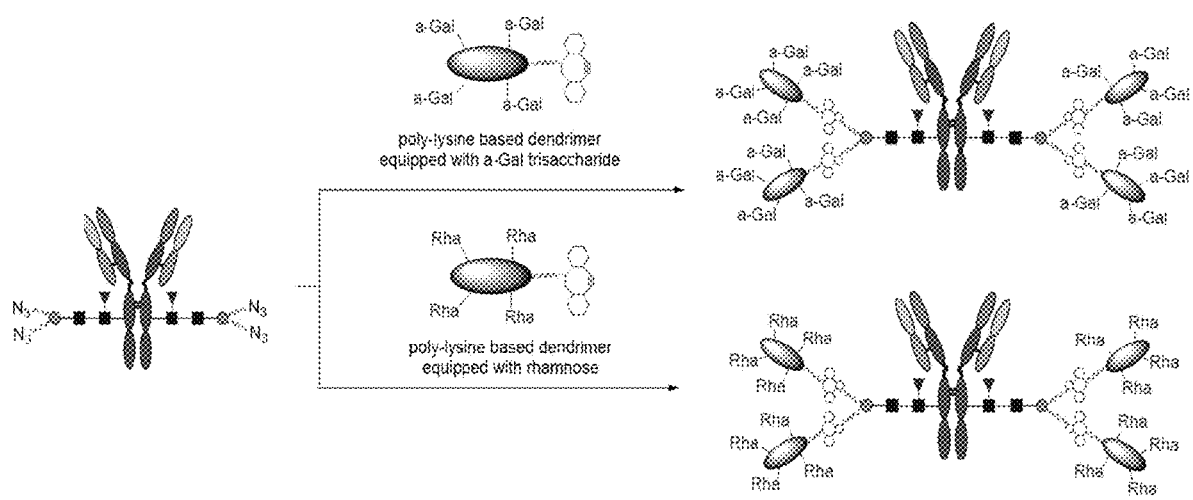
FIG. 19. Conjugation of α-Gal trisaccharide or rhamnose dendrimers for complement-dependent cytotoxicity (CDC).

Site-specific conjugation of α-Gal and rhamnose for complement-dependent cytotoxicity (CDC). Complement-dependent cytotoxicity (CDC) is one of the major mechanisms for antibody-mediated killing of target cells (s Andrighetto et al., 2019 Int J Mol Sci 20), Nevertheless, many therapeutic antibodies are limited by their low potency in stimulating a strong complement-dependent cytotoxicity. It was next tested as to whether one could apply the chemoenzymatic approach to make α-Gal or rhamnose (Rha) antigen-antibody conjugates so that natural anti α-Gal and anti-Rha IgG and IgM antibodies can be recruited to cause strong CDC responses to kill the target cells (cancer, bacteria, viruses). Previous studies showed that the presentation of multiple copies of the α-Gal epitopes (multivalency) was important for an efficient cancer cell killing (J Sianturi et al., 2019 Angew Chem Int Ed 58:4526-4530), so the poly-lysine based dendrimer with multiple copies of α-Gal trisaccharide or Rha were used for conjugation, affording the α-Gal/Rha-antibody conjugates with tailored numbers of glycan ligands (FIG. 19). Cell killing studies showed that the conjugates exhibited a complement-dependent cytotoxicity in antigen positive cell lines, and the potency increased with the increase of the valency.

Site-specific conjugation of specific glycan or peptide ligands to antibody for targeting. The method also covers the site-specific conjugation of any other glycan ligands or other peptide/protein ligands for targeting and enhanced therapeutics. These include, for example, conjugation of GalNAc multivalent ligands for targeting asialoglycoprotein receptors to livers; conjugation of high-mannose type glycan ligands for targeting macrophages and dendritic cells; and conjugation of sialyl glycans to Siglecs on T-cells and tumor cells.

Site-specific introduction of high-affinity mannose-6-phosphate (M6P) ligands into antibody for lysosomal targeted protein degradation. Traditional drug development efforts are mainly focused on small molecules that target druggable proteins such as enzymes and receptors (A L Hopkin et al., 2002 Nat Rev Drug Disc 1:727-730). However, the undruggable targets that cannot be modulated by small molecules such as transcription factors, protein complexes, RAS family proteins, regulatory/scaffolding proteins (CM Crews 2010 Chem Biol 17:551-555; MJ Bond 2021 doi:10.1039/D1031CB00011J) etc., account for more than 85% of human proteome (J N Spradlin et al., 2021 Acc Chem Res doi 10.1021/acs.accounts. 1021c00065), thus controllable degradation of targeted proteins represents a new strategy to tackle the undruggability. Proteolysis targeting chimeras (PROTACs) that degrade proteins of interest (POI) through the ubiquitin-proteasome system (J Lu et al., 2015 Chem Biol 22:755-763) have been successfully employed in the degradation of different types of target proteins related to various diseases, including cancer (M Schapira et al., 2019 Nat rev Drug Disc 18:949-963; Y Zou et al., 2019 Cell Bichem Funct 37:21-30; A D Cottonet al., 2022 J Am Chem Soc 143:593-598), viral infection (K Montrose et al., 2014 Biochem Biophys Res Commun 453:735-740), immune disorders (R Kolb et al., 2021 Nat Commun 12:1281) and neurodegenerative diseases (S TOMISHIGE ET AL., 2021 Ange Chem Int Edd 60:3346-3354). However, this strategy is limited to target engagement within the cells for ubiquitination (P M Cromm et al., 2017 Cell Chem Biol 24:1181-1190), leaving membrane and extracellular proteins untargetable, thus the development of complementary strategies that include proteins without cytosolic binding domains are greatly needed.

Figure 20:
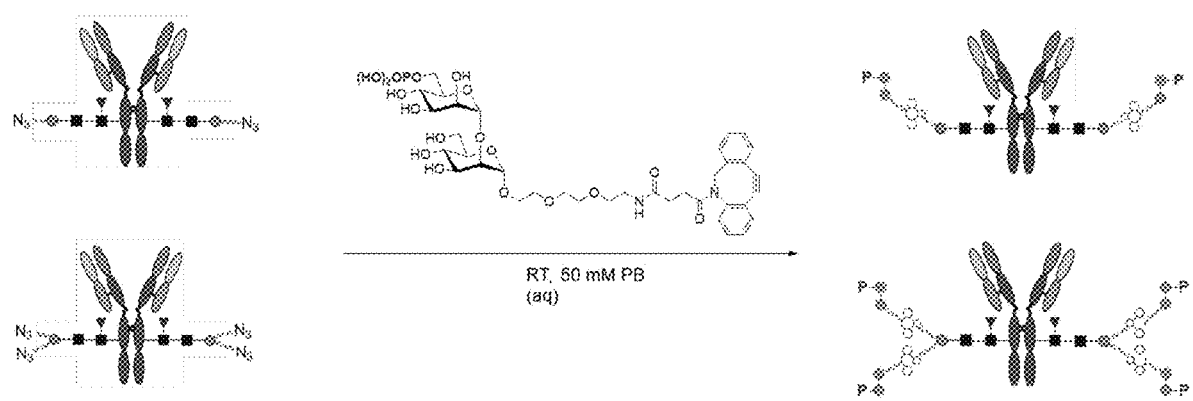
FIG. 20. Conjugation of high-affinity M6P disaccharide to make homogeneous LYTACs.

Lysosome is another major destination for protein degradation through autophagy and endocytosis (CA Lamb et al., 2013 Bioessays 35:34-45). Unlike the proteasomal pathway, the lysosomal pathway for protein degradation is not limited to proteins that have intracellular domains. In 2020, lysosome-targeting chimeras (LYTACs) consisting of an antibody for recruiting and ligands of lysosomal-targeting receptor (CI-MPR) for developed for delivery (SM Banik et al, 2020 Nature 584:291-297). Here the important glycan ligand mannose-6-phosphate (M6P), which can be recognized by CI-MPR and play a critical role in intracellular transport of lysosomal enzymes (S Kornfield 1987 FASEB 1:462-468; K Von Figura et al., 1986 Annu Rev Biochem 1986 55:167-193) will induce internalization of the chimera once introduced to the antibody. In this way they successfully achieved the depletion of secreted and membrane-associated proteins. Despite these promising results, however, the CI-MPR-driven LYTACs suffered from heterogeneity of M6Pn polymers (SM Banik et al, Nature 584:291-297), and the random conjugation may also result in potential instability and rapid clearance. Preliminary experiments showed that the Man6P α-1,2Man disaccharide moiety was the minimal structure for CI-MPR binding, allowing one to construct homogeneous LYTACs using the azido-tagged antibody platform in a site-specific manner (FIG. 20). SPR binding studies showed that the antibodies with two or four Man6P α-1,2Man disaccharide moieties exhibited strong binding affinities with the receptor, with $K_D$ values of 17.0 nM and 42.6 nM, respectively (FIG. 21), providing broad implications for biochemical research and for therapeutics.

Figure 52:
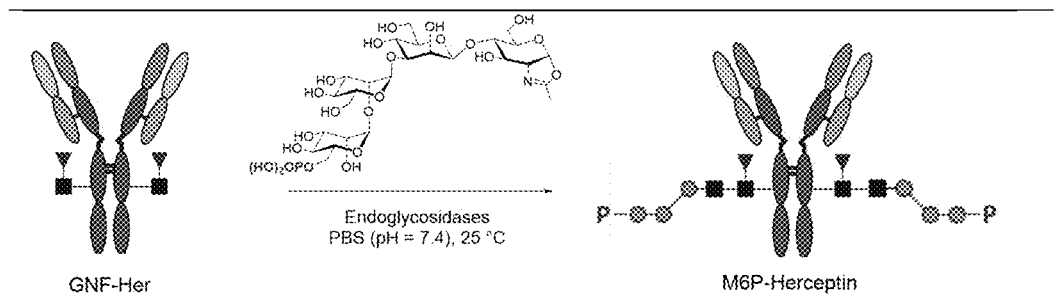
FIG. 52 Screening of the transglycosylation conditions.

Considering that the introduction of unnatural structures may be immunogenic in humans, it was investigated whether one could introduce the essential M6P disaccharide through natural linkages, thus the tetrasaccharide oxazoline containing the Man6Pα1,2Man disaccharide moiety was selected as the donor substrate to examine the transglycosylation activities of different endoglycosidases to make M6P-modified antibodies. To this end, trastuzumab, an anti-Her2 antibody (Herceptin), was used as a model mAb (FIG. 52). Experiments were started from wild-type Endo S that has been found to be highly active and specific for Fc deglycosylation of intact IgG antibodies (W Huang et al, 2012 J Am Chem Soc 134:12308-12318; M Collin et al., 2001 EMBO J. 20:3046-3055).

With a catalytic amount of enzyme (0.2% w/w), it was found that wild-type Endo S was quite efficient for transglycosylation, more than 70% of the starting material was transformed into the desired product within 1 hour, and the reaction could be driven to completion if another batch of oxazoline (10 equiv.) was added. Marginal hydrolysis of the attached glycans was observed under this condition, which allowed for the accumulation of product. Considering the potent transglycosylation activity, together with its efficient hydrolysis of the complex-type N-glycans from the commercial antibody, wild-type Endo S provided a practical "one-pot" strategy for remodeling of heterogeneous glycoforms of antibody to produce a homogeneous structure. Then, its mutant, Endo S-D233Q was tested, which could efficiently transfer large biantennary glycan oxazoline to antibodies (W Huang et al, 2012 J Am Chem Soc 134: 12308-12318) but was found to show much slower transglycosylation as compared with wild-type Endo S. Relatively large amount of enzyme and oxazoline, together with longer incubation time were needed to drive the reaction to completion. In comparison, it was found another endoglycosidase from the *Streptococcus pyogenes* of serotype M49, namely Endo S2 (J Sjogren et al., 2013 Biochem J 455:107-118) also exhibited good transglycosylation activity and slow hydrolysis of the product with a catalytic amount of enzyme (0.1%, w/w). However, this enzyme would rapidly hydrolyze the glycan oxazoline, thus large excess amount of oxazoline was needed to promote this reaction.

In order to reduce the hydrolysis of oxazoline substrate, the mutant Endo S2-D184M was tested, a glycosynthase with broad substrate specificity and diminished hydrolytic activity (T Li et al., 2016 J Biol Chem 291:16508-16518) and it was found to exhibit excellent transglycosylation activity. With catalytic amount of enzyme (0.1%~0.2% w/w) and reduced equivalents of oxazoline (10 equiv.), the reaction smoothly afforded the product within 1 hour. As expected, no additional oxazoline was needed and marginal hydrolysis of the product was observed, thus providing another practical method for production of M6P-containing antibodies. In addition to the four enzymes, several other endoglycosidases were tested. Endo F3, which prefers to hydrolyze the core-fucosylated complex-type N-glycans (JP Giddens et a 2016 J Biol Chem 291:9356-9370) showed slow transglycosylation if a large amount of enzyme (10%, w/w) was added. And Endo F3-D165A, a glycosynthase mutant that has been used for remodeling of both Fab and Fc glycans of therapeutic antibody (JP Giddens et al., 2018 PNAS USA 115:12023-12027) didn't show significant activity toward this azido-tagged disaccharide, only trace of transitional product was observed. As for Endo A, Endo D and Endo CC that prefer non-fucosylated substrates, the GNF-Herceptin was treated with a fucosidase (BfFucH) to produce an afucosylated Fc glycoform. The results showed that all these three enzymes didn't produce cancer any product even large amount of enzyme (10%, w/w) was used.

Figure 21:
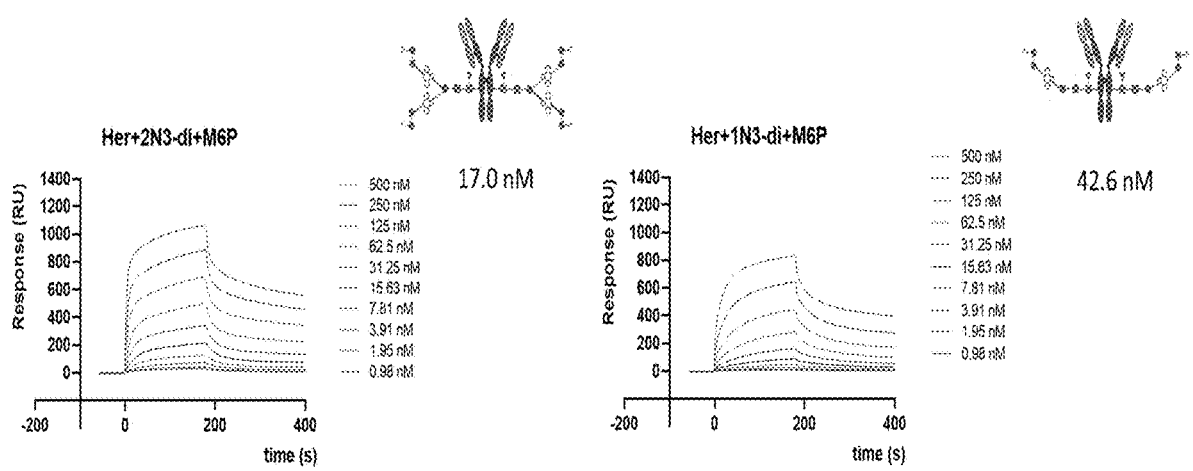
FIG. 21. SPR binding studies of the M6P-modified antibodies.

With the optimized condition in hand, the transglycosylation was tried in a preparative scale. The results showed that Endo S2-D184M worked well with GNF-Herceptin, the desired product carrying two phosphorylated glycans was isolated in 95% yield after protein A purification, and the excess glycan oxazoline could be recovered in the form of free oligosaccharide, which was readily converted into the glycan oxazoline in a single step with DMC/Et$_3$N (n Noguchi et al., 2009 J Org Chem 74:2210-2212) thus permitting the recycling of glycan oxazoline for transglycosylation. Besides Herceptin, another therapeutic antibody named Cetuximab that targets epidermal growth factor receptor (anti-EGFR) for the treatment of colorectal cancer and squamous-cell carcinoma (CH Chung et al., 2008 N Engl J Med 358:1109-1117) was also remodeled by this chemoenzymatic method. Cetuximab is glycosylated in both Fab and Fc domains with tremendous heterogeneity in the N-glycan structures (J Qian et al., 2007 364:8-18). Previous studies showed that wild-type Endo S2 is highly specific for hydrolyzing the Fc glycans (JP Giddens et al., 2018 Proc Natl Acad Sci USA 115:12023-12027), thus the commercial Cetuximab was firstly treated with Endo S2-WT to produce the deglycosylated Fc glycoform, then the resulting GNF-Ctx successfully afforded the phosphorylated product following the same chemoenzymatic method as monitored by LC-MS, which was isolated in 90% yield. Finally, to further verify that the glycans were specifically conjugated to the Fc domain, the products were digested with the protease IdeS followed by LC-MS analysis (G Chevreux et al., Anal Biochem 2011 415:212-214). The results showed that the shift of molecular weight was consistent with the attached glycans, thus confirmed the structure of the products (FIG. 21).

Figure 22:
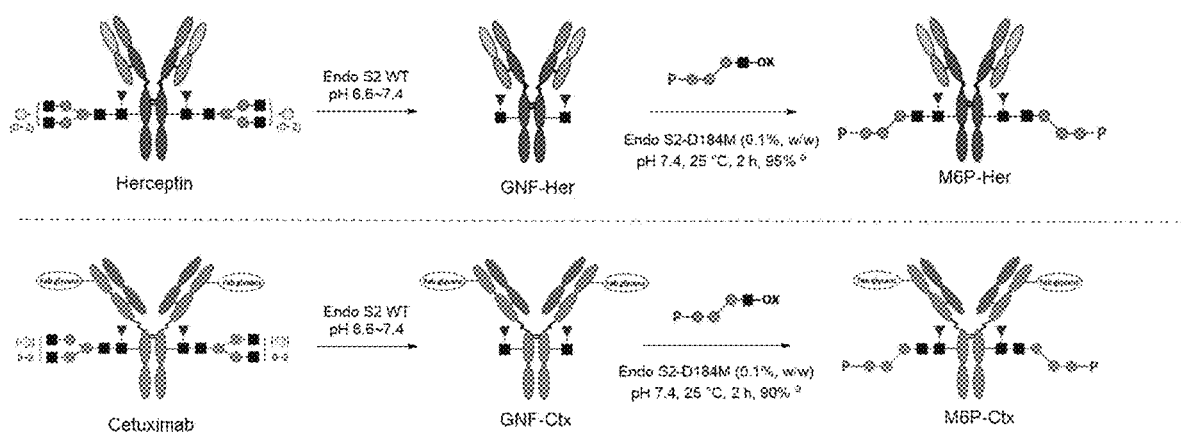
FIG. 22. Chemoenzymatic glycan remodeling of Herceptin and Cetuximab.
Figure 23:
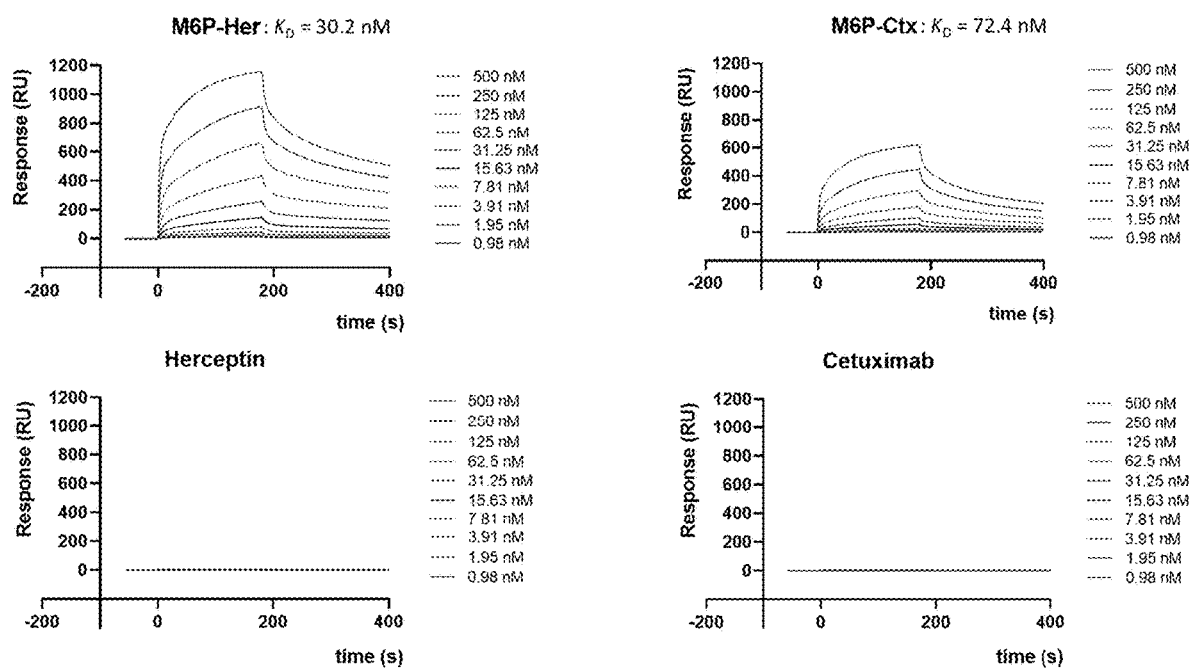
FIG. 23. SPR binding data of the CI-MPR with M6P-containing antibodies.
Figure 24:
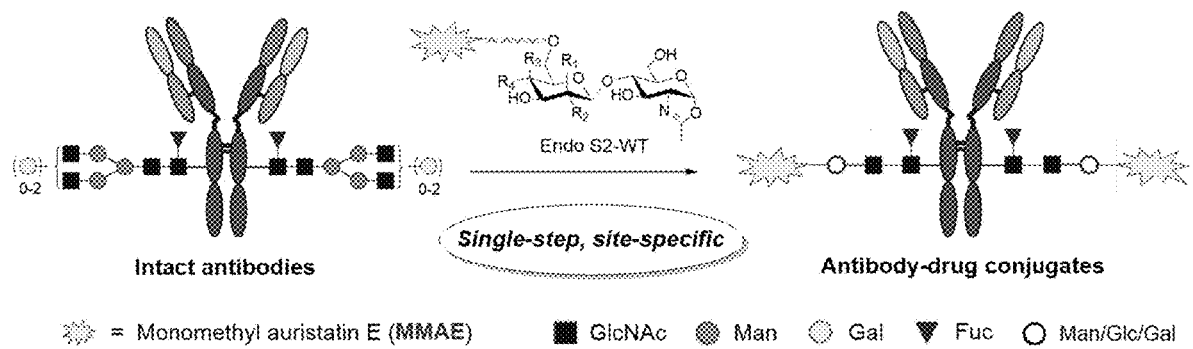
FIG. 24. Design of the single-step synthesis of ADCs from intact antibodies.

FIG. 22 demonstrates hemoenzymatic glycan remodeling of Herceptin and Cetuximab. The reactions were conducted with 10 eq of oxazoline in PBS buffer. a, isolated yield. In order to evaluate the binding affinities of the M6P-modified antibodies to lysosomal-targeting receptor, we performed SPR experiments with immobilized CI-MPR. The results showed that the M6P-containing antibodies acted as excellent ligands of CI-MPR, with $K_D$ values of 30.2 nM and 72.4 nM for M6P-Her and M6P-Ctx, respectively, while no significant binding was observed with native antibodies (FIG. 23). FIG. 23 demonstrates SPR binding data of the CI-MPR with M6P-containing antibodies. The analytes were flowed over an immobilized chip with 2-fold serial dilution of the highest concentration of 500 nM.

Example 2

Antibody-drug conjugates (ADCs) hold great promise for targeted cancer cell killing. Site-specific antibody-drug conjugation is highly desirable for synthesizing homogeneous ADCs with optimal safety profiles and high efficacy. The synthesis and evaluation of new disaccharide oxazolines as enzyme substrates for examining the scope of the site-specific conjugation is described herein. Specifically, azide-functionalized disaccharide oxazolines derived from Manβ1,4GlcNAc, Glcβ1,4GlcNAc, and Galβ1,4GlcNAc (LacNAc), respectively, were synthesized. Enzymatic evaluation revealed that wild-type Endo-S2 demonstrated highly relaxed substrate specificity and could accommodate all the three types of disaccharide derivatives for transglycosylation to provide site-specifically azide-tagged antibodies, which were readily clicked with a payload to generate homogeneous ADCs. Moreover, it was found that Endo-S2 was able to accommodate drug-preloaded minimal disaccharide oxazolines as donor substrate for glycan transfer, enabling an efficient, single-step and site-specific antibody-drug conjugation without the need of click reaction. The ability of Endo-S2 to accommodate simpler and more easily synthesized disaccharide oxazoline derivatives for Fc glycan remodeling further expanded the scope of this bioconjugation method for constructing homogeneous antibody-drug conjugates in a single step manner. Finally, cell-based assays indicated that the synthetic homogeneous ADCs demonstrated potent targeted cancer cell killing.

Described herein is the synthesis and evaluation of selectively modified new disaccharide oxazolines, including the Glc-β1,4-GlcNAc and Gal-β1,4-GlcNAc (LacNAc) disaccharides, as substrates for enzymatic Fc-glycan remodeling of antibodies. It was found that wild-type Endo-S2 had a remarkable flexibility to accommodate the "unnatural core disaccharides" for transglycosylation to provide azide-functionalized antibodies. Moreover, it was discovered that the wild-type Endo-S2 could perform a simultaneous deglycosylation and glycosylation of an antibody with the drug-loaded disaccharide oxazoline substrates to give homogeneous ADCs in a single step. The resulting ADCs showed high selectivity for the target cells as indicated in the cytotoxicity studies.

Recent studies have shown that wild-type Endo-S2 could accommodate selectively modified disaccharide oxazolines corresponding to the natural disaccharide (Manβ1,4GlcNAc) core for transglycosylation without product hydrolysis. However, whether this enzyme could recognize and transfer unnatural core disaccharide structures to antibodies remains to be tested. As described herein, simpler disaccharide derivatives, such as Glcβ1,4GlcNAc and Galβ1,4GlcNAc (LacNAc) oxazolines were tested which are much easier to synthesize than the Manβ1,4GlcNAc core. To explore the substrate specificity of Endo-S2 and to identify simple functionalized disaccharide oxazoline substrates for antibody glycan remodeling, three selectively modified disaccharide cores (Manβ1,4GlcNAc, Glcβ1,4GlcNAc, and Galβ1,4GlcNAc) were designed and synthesized with anamine or azide functional group at the 6' position for further derivatization (FIG. 25). First, global deprotection of the known compound (4) (Zhang et al., 2021 ACS Chem Biol DOI 10.1021 aschembio.1c00597) afforded the Man-GlcNAc disaccharide (5) in almost quantitative yield. Under this condition, the azido group was simultaneously reduced to an amino group, which could be used for the introduction of functional groups. For the synthesis of the glucose-based disaccharide (Glc-GlcNAc), a two-step manipulation was conducted to convert the benzoyl group in 7 (Yamauchi et al., 2016 138:12472-85) to a permanent benzyl group, giving 8 in 87% overall yield. Next, regioselective ring-opening reaction furnished 9 with a free OH at C6 position, and after the conversion of the 2-azido group into the 2-acetamido group with AcSH, (Wang et al., 2013 Science 341: 379-83) an azido-tagged polyethylene chain was introduced at this position by treatment of 10 with NaH and $N_3(CH_2CH_2O)_3Ts$ to give 11 in 85% yield. Catalytic hydrogenation removed all the protecting groups and afforded free glycan 12 in excellent yield. To test the substrate specificity of Endo-S2, the amine group in 12 was transformed back to the azido group by the copper-catalyzed diazo transfer reaction (Zhang et al., 2021 ACS Chem Biol 16:2502-2514) giving 13 in 81% yield, which was further transformed to oxazoline 14 by treatment of DMC and $Et_3N$ in water. Finally, the galactose-based disaccharide was constructed by coupling of 15 (Lossouarn et al., 2020 Org Biomol Chem 18:3874-3887) and 16 (Zhang et al., 2021 ACS Chem Biol 16:2502-2514) under standard glycosylation conditions. Selective protection of the C6-OH with TBDPS group at the Gal residue followed by per-benzylation after de-acetylation afforded 18 in 68% overall yield, which was transformed to 19 by the conversion of the 2-azido group into the 2-acetamido group. Upon the deprotection of TBDPS, the azido-tagged polyethylene chain was introduced to give 21, which, after global deprotection, provided 22 quantitatively. Subsequent diazo transfer reaction and oxazoline formation gave 24 in excellent yield (FIG. 25).

Figure 27:
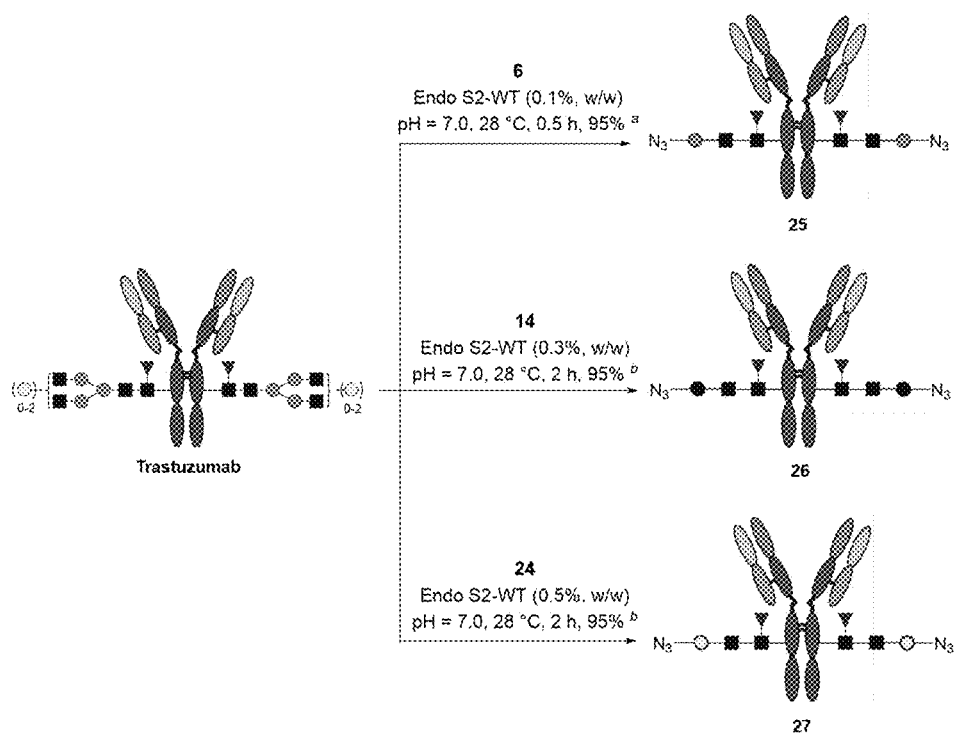
FIG. 27. Scheme 2. Transglycosylation of azido-tagged disaccharide oxazolines. The reactions were conducted in PBS buffer with antibody concentration of 20 mg/mL and the yields were based on the LC-MS peak intensities. For each reaction site: a. 20 eq of oxazoline was used; b. 15 eq of oxazoline was used.

To test if the Glc- or Gal-containing disaccharide oxazolines (14 and 24) could still be recognized by wild-type Endo-S2 for Fc glycan remodeling of antibodies, the one-pot transglycosylation was tested using trastuzumab (Herceptin) as a model antibody (FIG. 27; Scheme 2). It was found that disaccharide oxazolines 14 and 24 both could act as donor substrates for Endo-S2 catalyzed transglycosylation, but enzymatic reactions were slower than that of the Man-β1,4-GlcNAc oxazoline (6) corresponding the natural disaccharide core. This result suggests that replacing the "natural" β-D-Man moiety with β-D-Glc or β-D-Gal residue reduced their substrate activity toward Endo-S2 to some extent, but Endo-S2 could still recognize them as donor substrates. Nevertheless, it was also found that replacing the natural β-Man moiety with a β-Glc and β-Gal moiety could make the sugar oxazolines more resistant to Endo-S2 catalyzed hydrolysis. Thus, more enzyme and less equivalents of sugar oxazolines could be used to drive the transglycosylation to completion. The ability of Endo-S2 to accept the Glcβ1,4GlcNAc and LacNAc oxazolines for transglycosylation is significant, as synthesis of these disaccharide derivatives are more efficient and straightforward than the Manβ1,4GlcNAc derivative as previously reported. (Zhang et al., 2021 ACS Chem Biol 16:2502-2514). The transglycosylation products, 26 and 27, respectively, were purified by protein A affinity column, and their identity was confirmed by LC-ESI-MS analysis Encouraged by the excellent transglycosylation activities of the azido-tagged disaccharide oxazolines, it was attempted to pre-introduce the cytotoxic drug to the disaccharide oxazolines and to test the feasibility of a single-step glycan remodeling for constructing ADCs. To achieve this strategy, several factors needed to be considered. First, the drug should tolerate the $DMC/Et_3N$ treatment for sugar oxazoline formation. Second, it needs to be stable under alkaline conditions. Lastly, the drug-disaccharide oxazoline should have sufficient solubility in aqueous solution.

Figure 26:
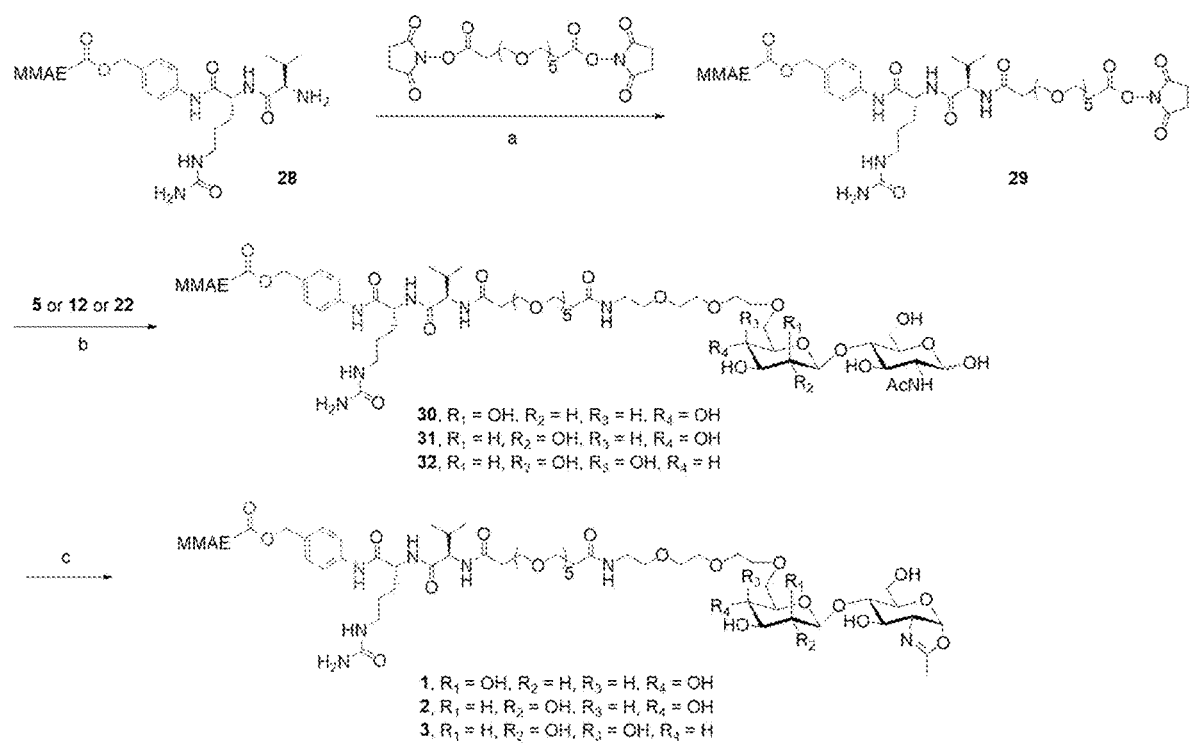
FIG. 26. Scheme 3. Synthesis of drug-oxazoline conjugates (1-3). Reagents and conditions: a) $Et_3N$, DMSO, RT, 82%; b) $Et_3N$, DMSO, RT; c) DMC, $Et_3N$, $H_2O$/DMSO, 0° C., 1, 73% for 2 steps, 2, 80% for 2 steps, 3, 70% for 2 steps.

Monomethyl auristatin E (MMAE) was chosen as the cytotoxic drug to test the strategy. Thus, compound 28 (Ou et al., 2021 Bioconjug Chem 32; 1888-1897) bearing a cleavable dipeptide linker (valine-citrulline) was reacted with bis-NHS-PEG5 to give the NHS-activated payload 29, which was further conjugated with the disaccharides via amine-coupling reaction, followed by oxazoline formation in one-pot, providing the drug-oxazoline conjugates 1-3 in good yields after RP-HPLC purification (FIG. 26; Scheme 3).

Figure 28:
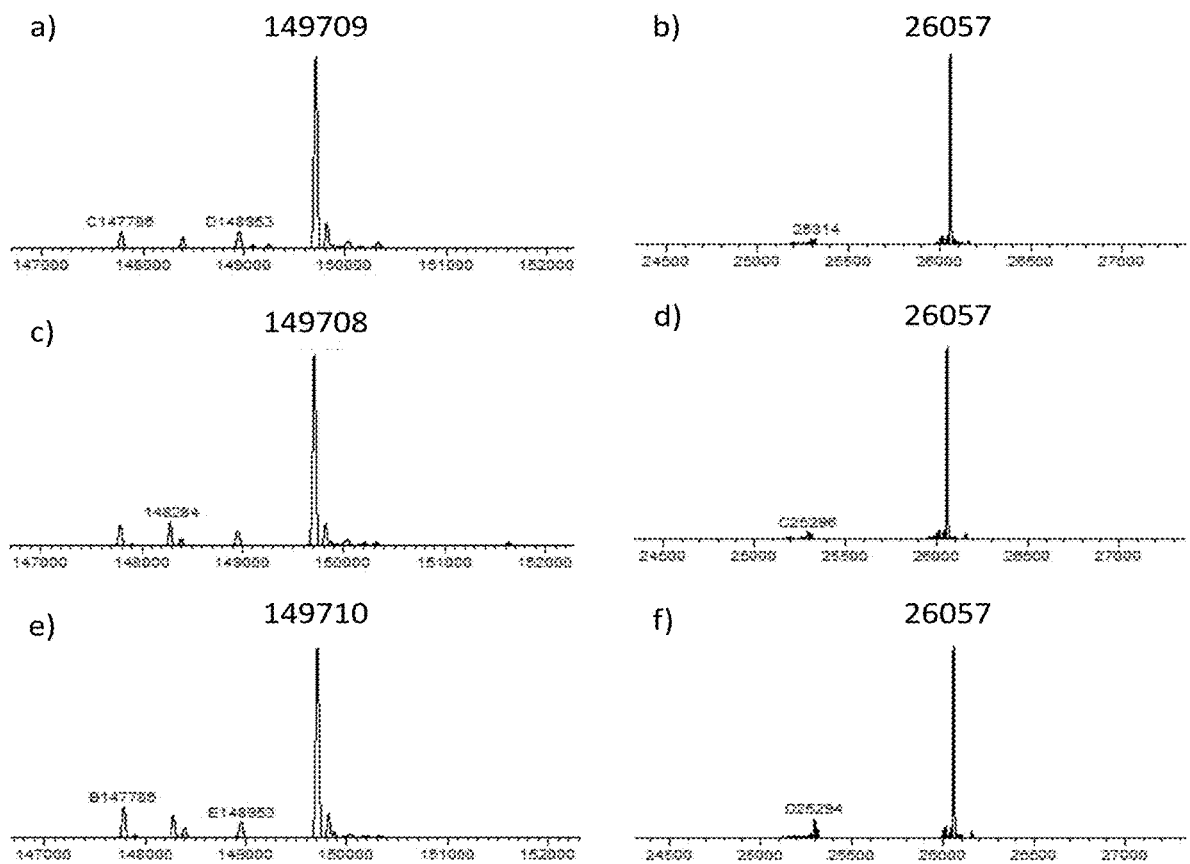
FIG. 28A-F. LC-ESI-MS analysis of the intact ADCs and the Fc domains released by IdeS treatment.
Figure 30:
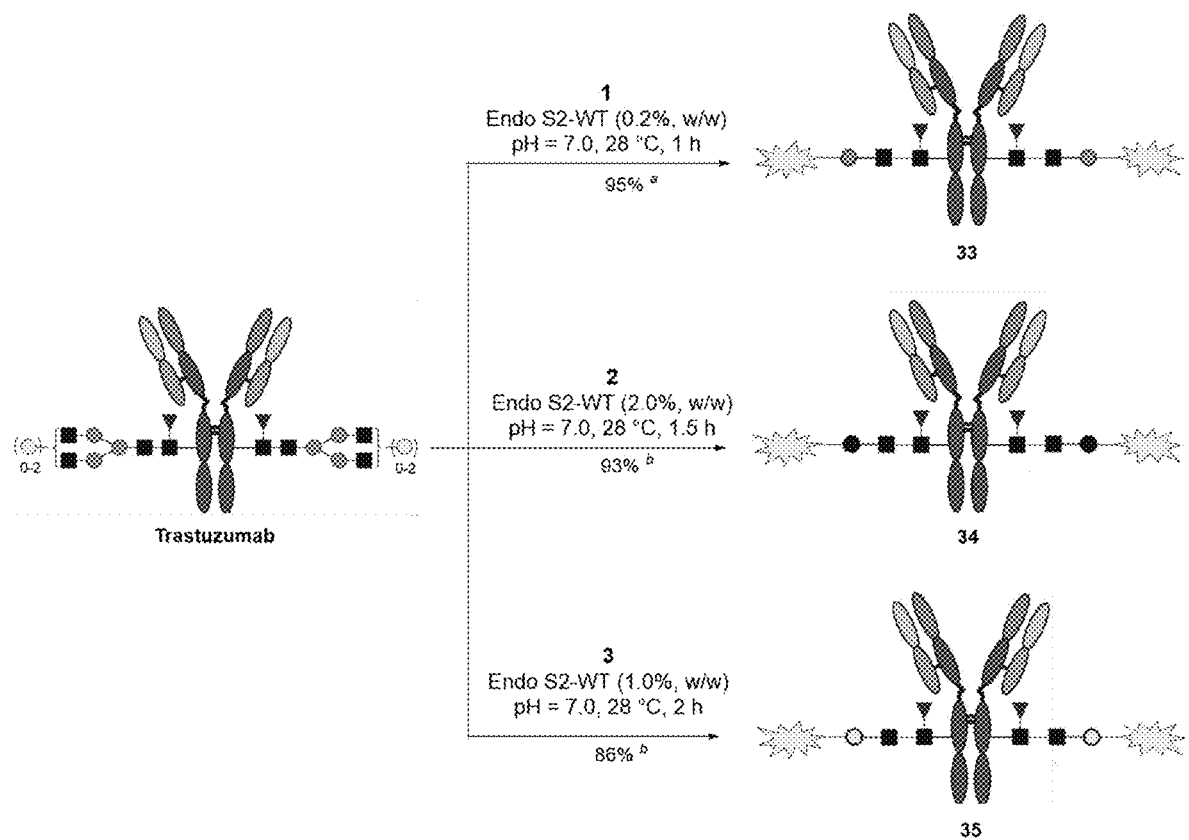
FIG. 30. Scheme 4. Single-step transglycosylation of drug-oxazoline conjugates to make ADCs (33~35). The reaction was conducted in PBS buffer with 5% DMSO and antibody concentration was 20 mg/mL, the yields were based on protein A purification. For each reaction site: a. 15 eq of oxazoline was used; b. 25 eq of oxazoline was used.

With the drug-sugar oxazoline conjugates in hand, it was investigated whether the one-step synthesis of ADCs via the Endo-S2-catalyzed transglycosylation (FIG. 30; Scheme 4). Notably, the oxazolines 1-3 could not be completely dissolved in aqueous buffer solution due to the hydrophobicity of MMAE and the cleavable linker, thus 5% DMSO was added to help dissolve the oxazolines in the buffer. It was found that the Man-derived drug-oxazoline conjugate (1) acted as an excellent substrate of wild-type Endo-S2, and the reaction reached completion within 1 h with a catalytic amount of enzyme (0.2%, enzyme to antibody, w/w) and 15 equiv. of the sugar oxazoline donor (1). Once formed, the product was largely resistant to hydrolysis under the reaction conditions, thus offering a practical one-step method for the preparation of homogeneous ADCs with a precise control of DAR. As for Glc- and Gal-derived drug-oxazolines (2 and 3, respectively), relatively larger amounts of enzyme and oxazoline donors were required to push the reaction to completion. In all the cases, the corresponding antibody-drug conjugates (33, 34, and 35, respectively) were obtained. To verify that the drugs were specifically conjugated to the Fc domain, the ADCs (33, 34, and 35) were digested with protease IdeS, which cleaves the antibody to yield the monomeric Fc domain, followed by LC-ESI-MS analysis. The results showed high homogeneity of the products and the shifts of molecular weight were consistent with the attached payloads (calculated for the drug-conjugated Fc domain, M=26056; observed, 26057, deconvoluted data), thus further confirmed the structure of the products (FIG. 28). The findings that Endo-S2 can perform simultaneous antibody deglycosylation and transfer of a payload-conjugated disaccharide oxazoline further expands the scope of the chemoenzymatic Fc glycan remodeling method for synthesizing homogeneous antibody-drug conjugates.

Finally, the cytotoxicity of the synthetic ADCs (33, 34, and 35) was tested in breast cancer cell lines, the SK-BR-3 and BT474 cell lines that have high levels of HER2 expression and the T47D that has low level expression of HER2 antigen. The trastuzumab-MMAE conjugate (36) (with a DAR of 2) that was synthesized previously using a two-step approach[18] was used as a reference for comparison. It was found that all these ADCs achieved significant cell killing of the high antigen-expressed cell lines (SK-BR-3 and BT474) with almost the same potency, as indicated by the half-maximal effective concentration ($EC_{50}$) values. On the other hand, no apparent killing was observed in the T47D cell line that expresses low levels of HER2 under the tested concentrations, indicating the high selectivity of the synthetic ADCs for the target cells.

As described herein, a highly efficient method for a single-step and site-specific chemoenzymatic synthesis of homogeneous antibody-drug conjugates is established. The findings that Endo-S2 can accept different disaccharide oxazolines, including the simpler and more easily synthesized cellobiose and N-acetyllactosamine derivatives for Fc glycan remodeling, further expands the scope of the chemoenzymatic method for antibody bioconjugation. In addition, the ability of Endo-S2 to perform deglycosylation of native antibodies and simultaneously transfer drug-preloaded disaccharide oxazolines enables a truly single-step protocol to construct homogeneous antibody-drug conjugates.

Materials and Methods

General procedure. All chemicals, reagents, and solvents were purchased from Sigma-Aldrich and TCI and unless specially noted applied in the reaction without further purification. TLC was performed using silica gel on glass plates (Sigma-Aldrich), and spots were detected under UV light (254 nm) then charring with 5% (v/v) sulfuric acid in EtOH or cerium molybdate stain (CAM) followed by heating at 150° C. Silica gel (200-425 mesh) for flash chromatography was purchased from Sigma-Aldrich. NMR spectra were recorded on a 400 MHz spectrometer (Bruker, Tokyo, Japan) with $CDCl_3$ or $D_2O$ as the solvent. The chemical shifts were assigned in ppm, and multiplicities are indicated by s (singlet), d (doublet), t (triplet), q (quartet), and m (multiplet). Coupling constants (J) are reported in Hertz. MALDI-TOF was performed on a Bruker Autoflex Speed Mass Spectrometer in positive reflectron mode with DHB (ACN/$H_2O$=1:1) as the matrix. HRMS was performed on an Exactive Plus Orbitrap Mass Spectrometer (Thermo Scientific) equipped with a C18 column. Preparative HPLC was performed with a Waters 600 HPLC instrument and Waters C18 columns (5.0 μm, 10×250 mm). The column was eluted with a suitable gradient of MeCN—$H_2O$ containing 0.1% TFA or FA at a flow rate of 4 mL/min. LC-MS analysis was performed on an Ultimate 3000 HPLC system coupled to an Exactive Plus Orbitrap mass spectrometer (Thermo Fisher Scientific) with C4 (whole antibody, gradient, 5-95% aq MeCN containing 0.1% FA for 6 min, 0.4 mL/min) or C8 (IdeS digestion, gradient, 25-35% aq MeCN containing 0.1% FA for 6 min, 0.4 mL/min) column. Deconvolution data was transformed by MagTran software.

6-O-2-[2-(2-aminoethoxy)ethoxy]ethyl-β-D-mannopyranosyl-(1→4)-2-acetamido-2-deoxy-β-D-glucopyranoside (5)

A mixture of 4 (Zhang et al., 2021 ACS Chem Biol 16:2502-2514) (15.0 mg, 0.014 mmol) and Pd/C (10 wt. % loading, 10 mg) in THF (1.5 mL) and $H_2O$ (0.5 mL) was added 3 M HCl (aq, 9 μL, 2 eq), then stirred under $H_2$ atmosphere overnight. After LC-MS analysis showed the complete conversion to free amine, the reaction mixture was filtered through a Celite pad, then concentrated and purified by Sephadex LH-20 ($H_2O$) to give 5 (7.2 mg, 97%) as hydrochloride salt. $^1H$ NMR (400 MHz, $D_2O$) δ 5.07 (0.77H, m), 4.61-4.59 (1.31H, m), 3.96-3.95 (1.00H, m), 3.85-3.80 (0.81H, m), 3.78-3.76 (1.90H, m), 3.75-3.73 (1.04H, m), 3.69-3.67 (0.99H, m), 3.66-3.63 (3.34H, m), 3.63-3.56 (11.1H, m), 3.54-3.49 (1.90H, m), 3.48-3.43 (2.39H, m), 3.10 (2H, t, J=4.6 Hz), 1.92 (3H, s); $^{13}C$ NMR (100 MHz, $D_2O$) δ 174.47, 174.17, 100.19, 94.81, 90.50, 79.54, 79.25, 74.68, 74.49, 72.64, 72.36, 70.44, 70.40, 69.92, 69.88, 69.73, 69.58, 69.40, 69.16, 66.58, 66.29, 63.81, 60.16, 60.03, 56.06, 53.63, 39.06, 22.13, 21.84; HRMS: $[M+H]^+$ calcd for $C_{20}H_{39}N_2O_{13}^+$, 515.2447; found, 515.2442.

Benzyl 2-O-benzyl-4,6-O-benzylidene-3-O-p-methoxybenzyl-β-D-glucopyranosyl-(1→4)-2-azido-3,6-di-O-benzyl-2-deoxy-β-D-glucopyranoside (8)

To a solution of 7 (Yamaguchi et al., 2016 J Am Chem Soc 138:12472-85) (290 mg, 0.31 mmol) in MeOH (2.0 mL) was added sodium methoxide to maintain a pH of 10, the solution was heated to 50° C. and stirred overnight. After the complete disappearance of the starting material, the solution was diluted with $CH_2Cl_2$, successively washed with $H_2O$ and brine, then concentrated to dryness. The residue was dissolved in dry N,N-dimethylformamide (2.0 mL) and cooled to 0° C., sodium hydride (24 mg) and benzyl bromide (100 μL) were added successively, and the mixture was slowly warmed to room temperature. After the completion of the reaction as indicated by TLC, MeOH was added to quench the excess sodium hydride. The reaction was diluted with $CH_2Cl_2$, and successively washed with $H_2O$ and brine. The organic layer was dried over anhydrous $Na_2SO_4$. After concentration, the residue was purified by flash column chromatography (hexanes/EtOAc=10:1~5:1) to afford 8 (248 mg, 87% for 2 steps) as white solid. $R_f$=0.45 (hexanes/EtOAc=5:1); $^1H$ NMR (400 MHz, $CDCl_3$) δ 7.53-7.51, 7.45-7.26 (27H, m, Ar—H), 6.85-6.83 (2H, m, Ar—H), 5.52 (1H, s, PhCH), 4.97-4.93 (2H, m, $PhCH_2$), 4.88-4.83 (2H, m, $PhCH_2$), 4.78-4.68 (4H, m, $PhCH_2$), 4.63 (1H, d, J=12.1 Hz, $PhCH_2$), 4.56 (1H, d, J=7.8 Hz), 4.43 (1H, d, J=12.1 Hz, $PhCH_2$), 4.31 (1H, d, J=8.1 Hz), 4.21 (1H, dd, J=5.0 Hz, J=10.5 Hz), 4.06 (1H, dd, J=9.3 Hz, J=9.3 Hz), 3.88 (1H, dd, J=3.7 Hz, J=11.1 Hz), 3.82 (3H, s, $OCH_3$), 3.70-3.58 (3H, m), 3.54-3.45 (2H, m), 3.40-3.33 (2H, m), 3.30-3.26 (1H, m), 3.22-3.15 (1H, m); $^{13}C$ NMR (100 MHz, $CDCl_3$) δ 159.26, 138.37, 138.31, 138.05, 137.42, 136.89, 130.62, 129.70, 129.00, 128.48, 128.45, 128.32, 128.27, 128.25, 128.07, 127.97, 127.95, 127.82, 127.73, 127.68, 126.07, 113.75, 102.79, 101.14, 100.38, 82.54, 81.78, 81.33, 80.83, 76.46, 75.51, 75.25, 75.18, 74.75, 73.30, 70.79, 68.71, 67.62, 65.85, 65.73, 55.29; MALDI-TOF: $[M+Na]^+$ calcd for $C_{55}H_{57}N_3NaO_{11}^+$, 958.39; found, 958.05.

Benzyl 2,4-di-O-benzyl-3-O-p-methoxybenzyl-β-D-glucopyranosyl-(1→4)-2-azido-3,6-di-O-benzyl-2-deoxy-β-D-glucopyranoside (9)

To a solution of 8 (110 mg, 0.118 mmol) in $BH_3$·THF (1 M, 2.0 mL) was added a solution of $Bu_2BOTf$ in $CH_2Cl_2$ (1 M, 200 μL) under argon atmosphere at 0° C. and the mixture was stirred at 0° C. for 40 min when TLC indicated the completion of the reaction. $Et_3N$ (150 μL) was added to the mixture, followed by careful addition of MeOH (500 μL). The mixture was co-evaporated with MeOH for three times and the residue was purified by silica gel flash chromatography (hexanes/EtOAc=6:1~2:1) to afford 9 (100 mg, 91%) as a white solid. $R_f$=0.30 (hexanes/EtOAc=3:1); $^1H$ NMR (400 MHz, $CDCl_3$) δ 7.45-7.32, 7.25-7.23 (27H, m, Ar—H), 6.88-6.86 (2H, m, Ar—H), 5.00-4.96 (2H, m, $PhCH_2$), 4.88-4.84 (3H, m, $PhCH_2$), 4.83-4.78 (3H, m, $PhCH_2$), 4.73 (1H, d, J=12.0 Hz, $PhCH_2$), 4.67-4.62 (2H, m), 4.51-4.48 (2H, m), 4.34 (1H, d, J=8.1 Hz), 4.02 (1H, dd, J=9.4 Hz, J=9.4 Hz), 3.87 (1H, dd, J=3.7 Hz, J=11.1 Hz), 3.83 (3H, s, $OCH_3$), 3.73-3.66 (2H, m), 3.60-3.52 (2H, m), 3.48 (1H, dd, J=9.1 Hz, J=9.1 Hz), 3.41-3.31 (4H, m), 3.22-3.17 (1H, m), 1.68 (1H, s); $^{13}C$ NMR (100 MHz, $CDCl_3$) δ 159.28, 138.42, 138.36, 138.13, 137.96, 136.91, 130.65, 129.56, 128.51, 128.42, 127.99, 127.91, 127.89, 127.81, 127.74, 127.71, 127.41, 113.87, 102.51, 100.41, 84.48, 82.86, 81.35, 77.97, 76.46, 75.50, 75.19, 75.16, 75.08, 75.04, 74.87, 73.40, 70.81, 67.60, 65.91, 61.84, 55.32; MALDI-TOF: $[M+Na]^+$ calcd for $C_{55}H_{59}N_3NaO_{11}^+$, 960.40; found, 959.99.

Benzyl 2,4-di-O-benzyl-3-O-p-methoxybenzyl-β-D-glucopyranosyl-(1→4)-2-acetamido-3,6-di-O-benzyl-2-deoxy-β-D-glucopyranoside (10)

A solution of 9 (35.0 mg, 0.037 mmol) in a mixture of AcSH/pyridine/$CHCl_3$ (0.6 mL/0.4 mL/0.6 mL) was stirred at 50° C. for 15 h. After the completion of the reaction as monitored by TLC, the resulting mixture was concentrated and the residue was subjected to flash chromatography on silica gel (hexanes/Acetone=4:1~2:1) to afford 10 (31.6 mg, 89%) as white solid. $R_f$=0.20 (hexanes/Acetone=3:1); $^1H$ NMR (400 MHz, $CDCl_3$) δ 7.40-7.28, 7.23-7.21 (27H, m, Ar—H), 6.86-6.84 (2H, m, Ar—H), 5.65 (1H, d, J=7.6 Hz), 5.00 (1H, d, J=7.6 Hz), 4.94-4.92 (2H, m), 4.89-4.87 (1H, m), 4.86 (1H, m), 4.84-4.75 (3H, m), 4.67-4.58 (4H, m), 4.53-4.46 (2H, m), 4.19 (1H, dd, J=9.0 Hz, J=9.0 Hz), 3.89 (1H, dd, J=8.6 Hz, J=8.6 Hz), 3.87 (1H, dd, J=3.9 Hz, J=11.0 Hz), 3.82 (3H, s, $OCH_3$), 3.75-3.69 (2H, m), 3.59-3.54 (2H, m), 3.48-3.34 (4H, m), 3.23-3.20 (1H, m), 1.85 (3H, s); $^{13}C$ NMR (100 MHz, $CDCl_3$) δ 170.47, 159.23, 138.83, 138.37, 138.12, 138.08, 137.58, 130.68, 129.51, 128.47, 128.44, 128.41, 128.40, 127.98, 127.90, 127.87, 127.81, 127.78, 127.70, 127.51, 113.83, 102.63, 98.91, 84.41, 82.81, 77.95, 77.76, 77.34, 75.43, 74.99, 74.85, 74.28, 73.32, 70.86, 68.11, 61.96, 56.87, 55.29, 23.61; MALDI-TOF: $[M+Na]^+$ calcd for $C_{57}H_{63}NNaO_{12}^+$, 976.42; found, 976.25.

Benzyl 2,4-di-O-benzyl-3-O-p-methoxybenzyl-6-O-2-[2-(2-azidoethoxy)ethoxy]ethyl-β-D-glucopyranosyl-(1→4)-2-acetamido-3,6-di-O-benzyl-2-deoxy-β-D-glucopyranoside (11)

To a solution of 10 (23.0 mg, 0.024 mmol) and the tosylate linker (Orgueira et al., Chem Eur J 2003 9:140-69) (23.8 mg, 0.073 mmol) in anhydrous DMF (0.6 mL) was added 60% sodium hydride (5.0 mg, 0.125 mmol) at 0° C. After stirring for 0.5 h at 0° C. then 6 h at room temperature, MeOH (50 μL) and AcOH (10 μL) were added to the reaction mixture at 0° C. The reaction mixture was concentrated to dryness. The residue was then purified by column chromatography on silica-gel (hexanes/Acetone=5:1~3:2) to give 11 (22.7 mg, 85%) as a white solid. $R_f$=0.30 (hexanes/Acetone=2:1); $^1H$ NMR (400 MHz, $CDCl_3$) δ 7.39-7.26 7.22-7.20 (27H, m, Ar—H), 6.85-6.83 (2H, m, Ar—H), 5.67 (1H, d, NH, J=7.8 Hz), 4.94-4.82 (6H, m), 4.79-4.74 (2H, m), 4.68-4.63 (2H, m), 4.61-4.56 (2H, m), 4.51-4.45 (2H, m), 4.05-4.03 (2H, m), 3.88 (1H, dd, J=4.1 Hz, J=10.7 Hz), 3.81 (3H, s, $OCH_3$), 3.77-3.65 (3H, m), 3.61-3.48 (14H, m), 3.39 (1H, dd, J=8.1 Hz, J=8.1 Hz), 3.34-3.28 (3H, m), 1.82 (3H, s); $^{13}C$ NMR (100 MHz, $CDCl_3$) δ 170.14, 159.19, 139.09, 138.43, 138.40, 138.17, 137.66, 130.77, 129.49, 128.43, 128.41, 128.40, 128.33, 128.26, 128.13, 128.06, 127.96, 127.88, 127.85, 127.80, 127.74, 127.69, 127.66, 127.63, 127.47, 113.80, 102.82, 99.13, 84.50, 82.76, 77.86, 77.73, 76.92, 75.39, 75.06, 75.02, 74.99, 74.81, 73.61, 73.25, 70.87, 70.69, 70.59, 70.55, 69.93, 69.85, 68.38, 55.50, 55.29, 50.60, 23.50; MALDI-TOF MS: $[M+Na]^+$ calcd for $C_{63}H_{74}N_4NaO_{14}^+$, 1133.51; found, 1133.27.

6-O-2-[2-(2-aminoethoxy)ethoxy]ethyl-β-D-glucopyranosyl-(1→4)-2-acetamido-2-deoxy-β-D-glucopyranoside (12)

A mixture of 11 (20.0 mg, 0.018 mmol) and Pd/C (10 wt. % loading, 10 mg) in THF (1.5 mL) and $H_2O$ (0.5 mL) was added 3 M HCl (aq, 12 μL, 2 eq), then stirred under $H_2$ atmosphere overnight. After LC-MS analysis showed the complete deprotection and conversion of the azide to free amine, the reaction mixture was filtered through a Celite pad. The filtrate was concentrated, and the residue was purified by Sephadex LH-20 ($H_2O$) to give 12 (9.2 mg, 93%) as hydrochloride salt. $^1H$ NMR (400 MHz, $D_2O$) δ 5.09 (0.52H, m), 4.62 (0.43H, d, J=7.9 Hz), 4.43-4.39 (1.04H, m), 4.26-4.22 (0.22H, m), 4.04-4.01 (0.26H, m), 3.89-3.82 (1.40H, m), 3.80-3.73 (3.73H, m), 3.67-3.55 (13.8H, m), 3.55-3.51 (2.34H, m), 3.43-3.38 (1.57H, m), 3.36-3.31 (1.26H, m), 3.24-3.18 (1.31H, m), 3.11 (1.18, t, J=4.9 Hz), 1.94 (3H, s); $^{13}$C NMR (100 MHz, $D_2O$) δ 174.53, 174.29, 102.59, 94.78, 90.51, 79.45, 79.11, 75.35, 74.69, 74.48, 73.05, 72.42, 70.10, 70.02, 69.63, 69.58, 69.46, 69.20, 69.15, 66.56, 60.34, 59.99, 59.85, 56.22, 53.74, 39.11, 22.16, 21.87; HRMS: [M+H]$^+$ calcd for $C_{20}H_{39}N_2O_{13}^-$, 515.2447; found, 515.2440.

6-O-2-[2-(2-azidoethoxy)ethoxy]ethyl-β-D-glucopyranosyl-(1→4)-2-acetamido-2-deoxy-β-D-glucopyranoside (13)

To a solution of 12 (9.0 mg, 0.016 mmol) in $H_2O$ (1.0 mL) was added freshly prepared solution of $TfN_3$ Orgueira et al. 2003, Chem Eur J 9) in $CH_2Cl_2$ (0.5 mL, ~0.16 mmol) containing $K_2CO_3$ (6.8 mg) and $CuSO_4$ (0.8 mg) at 0° C. Then MeOH was added to make the solution homogenous, and the mixture was stirred at room temperature for 36 h. The reaction mixture was filtered, and the filtrate was concentrated to dryness. The residue was purified on a Sephadex LH-20 column by elution with $H_2O$. Fractions containing the product were pooled and lyophilized, then further purified by preparative RP-HPLC (gradient, 5-15% aq MeCN containing 0.1% FA for 30 min; flow rate, 4 mL/min) to give 13 (7.2 mg, 81%) as a white solid after lyophilization. $^1$H NMR (400 MHz, $D_2O$) δ 5.09 (0.58H, d, J=2.5 Hz), 4.61 (0.47H, d, J=7.7 Hz), 4.42-4.40 (0.97H, m), 3.88-3.83 (1.23H, m), 3.80-3.75 (2.89H, m), 3.75-3.73 (1.01H, m), 3.65-3.56 (12.9H, m), 3.53-3.49 (1.75H, m), 3.43-3.38 (2.83H, m), 3.36-3.31 (1.18H, m), 3.24-3.19 (1.20H, m), 1.94 (3H, s); $^{13}$C NMR (100 MHz, $D_2O$) δ 174.51, 174.27, 102.61, 94.79, 90.48, 79.57, 79.30, 75.34, 74.70, 74.50, 73.05, 72.40, 70.11, 69.58, 69.53, 69.49, 69.19, 69.14, 60.05, 59.90, 56.20, 53.74, 50.10, 22.14, 21.84; HRMS: [M+H]$^+$ calcd for $C_{20}H_{37}N_4O_{13}^+$, 541.2352; found, 541.2344.

2-Methyl-{6-O-2-[2-(2-azidoethoxy)ethoxy]ethyl-β-D-glucopyranosyl-(1→4)-1,2-dideoxy-α-D-glucopyrano}-[2,1-d]-2-oxazoline (14)

To a solution of 13 (3.3 mg, 6.1 μmol) in $H_2O$ (150 μL) were added $Et_3N$ (30 mol. equiv.) and 2-chloro-1,3-dimethylimidazolinium chloride (DMC, 20 mol. equiv.) at 0° C. The reaction mixture was kept at this temperature for 8 h then purified by gel filtration on a Sephadex G-10 column that was eluted with 0.1% aq $Et_3N$ to afford 14 (3.0 mg, 94%) as white solid after lyophilization with aq. NaOH (0.05 mol. equiv., to keep the product at a basic condition). $^1$H NMR (400 MHz, $D_2O$) δ 5.96 (1H, d, J=7.3 Hz), 4.35 (1H, d, J=7.9 Hz), 4.26-4.23 (1H, m), 4.08-4.06 (1H, m), 3.78-3.75 (1H, m), 3.70 (1H, dd, J=2.3 Hz, J=12.4 Hz), 3.64-3.57 (12H, m), 3.54-3.52 (1H, m), 3.47-3.43 (1H, m), 3.40-3.37 (2H, m), 3.34-3.29 (2H, m), 3.18-3.14 (1H, m), 2.88-2.86 (1H, m), 1.94 (3H, s); $^{13}$C NMR (100 MHz, $D_2O$) δ 168.29, 104.14, 99.72, 78.35, 75.35, 74.74, 72.98, 70.79, 70.22, 69.58, 69.48, 69.18, 65.12, 61.52, 50.07, 12.85; HRMS: [M+H]$^+$ calcd for $C_{20}H_{35}N_4O_{12}^+$, 523.2246; found, 523.2233.

Benzyl 2,3,4,6-tetra-O-acetyl-β-D-galactopyranosyl-(1→4)-2-azido-3,6-di-O-benzyl-2-deoxy-β-D-glucopyranoside (17)

A mixture of trichloroacetimidate donor 15 (Wu et al., ACS Chem Biol 2014 9:468-750) (810 mg, 1.65 mmol), acceptor 16 (570 mg, 1.2 mmol) and activated 4 Å molecular sieves (1.5 g) in anhydrous $CH_2Cl_2$ (15.0 mL) was stirred at room temperature under an argon atmosphere for 1.5 h. It was then cooled to −40° C., and TMSOTf (27 μL, 0.15 mmol) was added. After stirring at −40° C. for 50 min, the mixture was quenched with triethylamine (50 μL). The mixture was filtered, and the filtrate was concentrated in vacuo. The residue was purified by flash silica gel chromatography (hexanes/EtOAc=10:1~3:2) to give 17 (832 mg, 86%) as white foam. $R_f$=0.30 (hexanes/EtOAc=2:1); $^1$H NMR (400 MHz, $CDCl_3$) δ 7.46-7.30 (15H, m, Ar—H), 5.29 (1H, d, J=3.3 Hz), 5.13 (1H, dd, J=8.0 Hz, J=10.4 Hz), 4.99-4.93 (2H, m), 4.85 (1H, dd, J=3.5 Hz, J=10.4 Hz), 4.81-4.74 (2H, m), 4.70 (1H, d, J=12.0 Hz, PhCH), 4.60 (1H, d, J=8.0 Hz), 4.50 (1H, d, J=12.0 Hz, PhCH), 4.30 (1H, d, J=8.1 Hz), 4.07-4.01 (2H, m), 3.87 (1H, dd, J=6.0 Hz, J=11.1 Hz), 3.79-3.72 (2H, m), 3.59 (1H, dd, J=7.0 Hz, J=7.0 Hz), 3.50 (1H, dd, J=8.3 Hz, J=9.8 Hz), 3.37 (1H, dd, J=9.1 Hz, J=9.1 Hz), 3.32-3.30 (1H, m), 2.13 (3H, s), 2.01 (3H, s), 2.00 (3H, s), 1.99 (3H, s); $^{13}$C NMR (100 MHz, $CDCl_3$) δ 170.19, 170.07, 169.18, 138.21, 137.73, 136.76, 128.63, 128.49, 128.23, 128.13, 128.04, 128.00, 127.95, 127.93, 127.72, 100.51, 100.07, 80.95, 76.05, 75.14, 74.85, 73.70, 70.95, 70.93, 70.52, 69.58, 67.44, 66.80, 65.78, 60.60, 20.78, 20.66, 20.64, 20.59; MALDI-TOF: [M+Na]$^+$ calcd for $C_{41}H_{47}N_3NaO_{14}^+$, 828.29; found, 828.05.

Benzyl 2,3,4-tri-O-benzyl-6-O-(tert-Butyldiphenylsilyl)-β-D-galactopyranosyl-(1→4)-2-azido-3,6-di-O-benzyl-2-deoxy-β-D-glucopyranoside (18)

To a solution of 17 (340 mg, 0.422 mmol) in MeOH (4.0 mL) was added sodium methoxide until pH=10, the solution was heated to 50° C. and stirred overnight. After the complete disappearance of the starting material, the reaction mixture was diluted with $CH_2Cl_2$, successively washed with $H_2O$ and brine. The organic layer was dried over anhydrous $Na_2SO_4$ and filtered. The filtrate was concentrated to dryness to give the crude deacylated intermediate. The residue was then dissolved in dry N,N-dimethylformamide (3.0 mL), imidazole (144 mg, 2.11 mmol) and tert-Butyl(chloro)diphenylsilane (312 μL, 1.2 mmol) were added successively, and the resulting mixture was stirred at room temperature until the completion of the reaction as indicated by TLC. The reaction mixture was diluted with $CH_2Cl_2$, successively washed with $H_2O$ and brine. The organic layer was dried over anhydrous $Na_2SO_4$ and filtered. The filtrate was concentrated to dryness. Then the residue was dissolved in dry N,N-dimethylformamide (3.0 mL) and cooled to 0° C., sodium hydride (135 mg, 3.38 mmol) and benzyl bromide (300 μL, 2.53 mmol) were added successively, and the mixture was slowly warmed to room temperature. After the completion of the reaction as monitored by TLC, MeOH was added to quench the excess sodium hydride. The reaction mixture was diluted with $CH_2Cl_2$, successively washed with $H_2O$ and brine. The organic layer was dried over anhydrous $Na_2SO_4$ and filtered. The filtrate was concentrated and the residue was purified by flash column chromatography on silica gel (hexanes/EtOAc=15:1~8:1) to give 18 (328 mg, 68% for 3 steps) as colorless syrup. $R_f$=0.40 (hexanes/EtOAc=4:1); $^1$H NMR (400 MHz, $CDCl_3$) δ 7.59-7.55, 7.46-7.25 (40H, m, Ar—H), 5.12 (1H, d, J=11.4 Hz), 5.00 (1H, d, J=10.0 Hz), 4.94 (1H, d, J=12.1 Hz), 4.86-4.76 (4H, m), 4.71-4.62 (3H, m), 4.60-4.58 (2H, m), 4.44-4.37 (2H, m), 4.28 (1H, d, J=8.1 Hz), 4.07 (1H, d, J=2.3 Hz), 3.96 (1H, dd, J=9.2 Hz, J=9.2 Hz), 3.89-3.84 (2H, m), 3.79 (1H, dd, J=9.5 Hz, J=9.5 Hz), 3.73-3.70 (1H, m), 3.65 (1H, dd, J=9.5

Hz, J=5.0 Hz), 3.48-3.42 (2H, m), 3.33-3.23 (3H, m), 1.08 (9H, s); $^{13}$C NMR (100 MHz, CDCl$_3$) δ 139.27, 138.88, 138.68, 138.31, 138.01, 136.99, 135.57, 134.86, 133.25, 133.19, 129.85, 129.73, 128.54, 128.48, 128.37, 128.29, 128.17, 128.10, 128.04, 127.97, 127.92, 127.88, 127.81, 127.77, 127.71, 127.64, 127.58, 127.51, 127.38, 127.21, 102.75, 100.45, 82.44, 81.38, 80.22, 76.11, 75.50, 75.40, 75.32, 74.79, 74.33, 73.76, 73.26, 72.84, 70.76, 67.85, 65.67, 61.16, 27.02, 26.96, 26.62, 19.23; MALDI-TOF: [M+Na]$^+$ calcd for C$_{70}$H$_{75}$N$_3$NaO$_{10}$Si$^+$, 1168.51; found, 1168.22.

Benzyl 2,3,4-tri-O-benzyl-6-O-(tert-Butyldiphenyl-silyl)-β-D-galactopyranosyl-(1→4)-2-acetamido-3,6-di-O-benzyl-2-deoxy-β-D-glucopyranoside (19)

A solution of 18 (300 mg, 0.262 mmol) in a mixture of AcSH/pyridine/CHCl$_3$ (0.8 mL/0.6 mL/0.8 mL) was stirred at 50° C. for 14 h. After the completion of the reaction as monitored by TLC, the resulting mixture was concentrated and the residue was subjected to flash chromatography on silica gel (hexanes/EtOAc=4:1~1:1) to afford 19 (240 mg, 79%) as colorless syrup. R$_f$=0.30 (hexanes/EtOAc=2:1); $^1$H NMR (400 MHz, CDCl$_3$) δ 7.60-7.56, 7.44-7.23, 7.20-7.18 (40H, m, Ar—H), 5.78 (1H, d, J=7.7 Hz), 5.08 (1H, d, J=11.3 Hz), 4.97 (1H, d, J=6.8 Hz), 4.89 (1H, d, J=11.9 Hz), 4.86-4.77 (5H, m), 4.63-4.51 (4H, m), 4.42-4.39 (2H, m), 4.06-4.02 (2H, m), 3.94 (1H, dd, J=7.5 Hz, J=7.5 Hz), 3.89-3.76 (4H, m), 3.68-3.64 (2H, m), 3.55-3.49 (1H, m), 3.45 (1H, dd, J=9.8 Hz, J=2.8 Hz), 3.30-3.26 (1H, m), 1.81 (3H, s), 1.07 (9H, s); $^{13}$C NMR (100 MHz, CDCl$_3$) δ 170.12, 139.12, 138.70, 138.62, 138.50, 138.37, 137.68, 135.53, 133.14, 129.87, 129.75, 128.44, 128.32, 128.30, 128.22, 128.12, 128.10, 127.99, 127.89, 127.82, 127.79, 127.76, 127.68, 127.66, 127.56, 127.53, 127.37, 127.19, 103.13, 99.06, 82.26, 80.08, 77.13, 76.66, 75.32, 75.24, 74.65, 74.31, 73.84, 73.68, 73.16, 72.89, 70.74, 68.73, 61.38, 55.02, 26.95, 23.47, 19.19; MALDI-TOF: [M+Na]$^+$ calcd for C$_{72}$H$_{79}$NNaO$_{11}$Si$^+$, 1184.53; found, 1184.07.

Benzyl 2,3,4-tri-O-benzyl-β-D-galactopyranosyl-(1→4)-2-acetamido-3,6-di-O-benzyl-2-deoxy-β-D-glucopyranoside (20)

To a solution of 19 (215 mg, 0.185 mmol) in THF (2.0 mL) was added TBAF (1 M in THF, 900 μL), and the mixture was stirred at 40° C. for 2 h. After the completion of the reaction as monitored by TLC, the resulting mixture was concentrated and the residue was subjected to flash chromatography on silica gel (hexanes/EtOAc=5:1~1:1) to afford 20 (140 mg, 82%) as a colorless syrup. R$_f$=0.25 (hexanes/Acetone=2:1); $^1$H NMR (400 MHz, CDCl$_3$) δ 7.38-7.24 (30H, m, Ar—H), 5.70 (1H, d, J=7.8 Hz), 4.99-4.93 (3H, m), 4.90 (1H, d, J=12.1 Hz), 4.85-4.73 (4H, m), 4.64-4.54 (4H, m), 4.44-4.41 (2H, m), 4.13 (1H, dd, J=8.2 Hz, J=8.2 Hz), 3.96 (1H, dd, J=8.0 Hz, J=8.0 Hz), 3.88-3.78 (3H, m), 3.74-3.73 (1H, m), 3.69-3.62 (2H, m), 3.55-3.49 (1H, m), 3.45-3.36 (2H, m), 3.26-3.23 (1H, m), 1.85 (3H, s); $^{13}$C NMR (100 MHz, CDCl$_3$) δ 170.42, 138.67, 138.62, 138.49, 138.39, 138.29, 137.61, 128.47, 128.38, 128.36, 128.32, 128.25, 128.19, 128.10, 127.92, 127.77, 127.74, 127.57, 127.54, 127.50, 103.19, 98.95, 82.48, 79.92, 77.48, 75.34, 75.13, 75.00, 74.41, 74.38, 73.71, 73.17, 73.11, 70.72, 68.64, 62.00, 55.71, 23.57; MALDI-TOF: [M+Na]$^+$ calcd for C$_{56}$H$_{61}$NNaO$_{11}$$^+$, 946.41; found, 946.04.

Benzyl 2,3,4-tri-O-benzyl-6-O-2-[2-(2-azidoethoxy)ethoxy]ethyl-β-D-galactopyranosyl-(1→4)-2-acetamido-3,6-di-O-benzyl-2-deoxy-β-D-glucopyranoside (21)

To a solution of 20 (120 mg, 0.13 mmol) and the tosylate linker (128 mg, 0.39 mmol) in anhydrous DMF (2.5 mL) was added 60% sodium hydride (26 mg, 0.65 mmol) at 0° C. After stirring for 0.5 h at 0° C. then 6 h at room temperature, the reaction was diluted with CH$_2$Cl$_2$, successively washed with H$_2$O and brine and dried over anhydrous Na$_2$SO$_4$. The mixture was filtered, and the filtrate was concentrated. The residue was purified by column chromatography on silica-gel (hexanes/Acetone=6:1~2:1) to give 21 (120 mg, 85%) as a colorless syrup. R$_f$=0.30 (hexanes/Acetone=2:1); $^1$H NMR (400 MHz, CDCl$_3$) δ 7.37-7.23 (30H, m, Ar—H), 5.78 (1H, d, J=7.7 Hz), 4.99 (1H, d, J=11.5 Hz), 4.96-4.89 (3H, m), 4.87-4.80 (2H, m), 4.76-4.74 (2H, m), 4.64-4.54 (4H, m), 4.47-4.41 (2H, m), 4.07 (1H, dd, J=8.0 Hz, J=8.0 Hz), 4.00 (1H, dd, J=7.5 Hz, J=7.5 Hz), 3.93 (1H, d, J=2.5 Hz), 3.88-3.84 (1H, m), 3.81-3.77 (2H, m), 3.69-3.60 (8H, m), 3.57-3.51 (4H, m), 3.48-3.40 (4H, m), 3.35 (2H, t, J=5.0 Hz), 1.86 (3H, s); $^{13}$C NMR (100 MHz, CDCl$_3$) δ 170.12, 138.98, 138.88, 138.66, 138.50, 138.34, 137.68, 128.39, 128.34, 128.31, 128.21, 128.16, 127.99, 127.90, 127.84, 127.69, 127.59, 127.55, 127.49, 127.46, 103.15, 99.12, 82.26, 79.92, 75.34, 75.22, 74.62, 73.76, 73.60, 73.13, 72.72, 70.70, 70.61, 70.55, 70.39, 70.04, 69.05, 68.72, 55.12, 50.65, 23.53; MALDI-TOF: [M+Na]$^+$ calcd for C$_{62}$H$_{72}$N$_4$NaO$_{13}$$^+$, 1103.50; found, 1103.10.

6-O-2-[2-(2-aminoethoxy)ethoxy]ethyl-β-D-galactopyranosyl-(1→4)-2-acetamido-2-deoxy-β-D-glucopyranoside (22)

To a mixture of 21 (75.0 mg, 0.069 mmol) and Pd/C (10 wt. % loading, 40 mg) in THF (4.5 mL) and H$_2$O (1.5 mL) was added 3 M HCl (aq, 46 μL, 2 eq), then the mixture was stirred under a H$_2$ atmosphere overnight. After LC-MS indicated the completion deprotection and conversion of the azide to amine, the reaction mixture was filtered through a Celite pad. The filtrate was concentrated and the residue was purified by Sephadex LH-20 (H$_2$O) to give 22 (37.2 mg, 97%) as hydrochloride salt. $^1$H NMR (400 MHz, D$_2$O) δ 5.10 (0.56H, m), 4.62 (0.42H, d, J=7.6 Hz), 4.37 (1.05H, d, J=7.9 Hz), 3.90-3.82 (2.22H, m), 3.81-3.76 (3.46H, m), 3.74-3.70 (0.71H, m), 3.65-3.55 (15.61H, m), 3.47-3.42 (1.28H, m), 3.00-2.98 (1.61H, m), 1.94 (3H, s); $^{13}$C NMR (100 MHz, D$_2$O) δ 174.51, 174.26, 102.98, 94.83, 90.51, 79.40, 79.07, 74.69, 73.33, 72.48, 72.40, 71.67, 70.80, 70.09, 70.00, 69.87, 69.62, 69.55, 69.49, 69.42, 69.21, 68.67, 67.95, 67.91, 60.35, 60.08, 59.93, 56.12, 53.70, 39.30, 22.18, 21.89; HRMS: [M+H]$^+$ calcd for C$_{20}$H$_{39}$N$_2$O$_{13}$$^+$, 515.2447; found, 515.2440.

6-O-2-[2-(2-azidoethoxy)ethoxy]ethyl-β-D-galactopyranosyl-(1→4)-2-acetamido-2-deoxy-β-D-glucopyranoside (23)

To a solution of 22 (9.0 mg, 0.016 mmol) in H$_2$O (1.0 mL) was added a freshly prepared solution of TfN$_3$ (Orgueira et al., 2003 Chem eu J 2003 9:140-69) in CH$_2$Cl$_2$ (0.5 mL, ~0.16 mmol) containing K$_2$CO$_3$ (6.8 mg) and CuSO$_4$ (0.8 mg) at 0° C., then MeOH was added to make the solution homogenous. The mixture was stirred at room temperature for 36 h and then the reaction mixture was filtered. The filtrate was concentrated to dryness and the residue was purified on a Sephadex LH-20 column by elution with H$_2$O. Fractions containing the product were pooled and lyophilized, then further purified by preparative RP-HPLC (gradient, 5-15% aq MeCN containing 0.1% FA for 30 min; flow rate, 4 mL/min) to give 23 (7.5 mg, 85%) as white solid. $^1$H NMR (400 MHz, D$_2$O) δ 5.09 (0.64H, m), 4.61 (0.43H, d, J=7.6 Hz), 4.37 (1.01H, d, J=7.8 Hz), 3.88-3.82 (2.28H, m), 3.79-3.75 (3.59H, m), 3.74-3.70 (0.62H, m), 3.67-3.54 (15.67H, m), 3.51-3.50 (0.41H, m), 3.47-3.38 (2.97H, m), 3.12-3.09 (0.23H, m), 1.94 (3H, s); $^{13}$C NMR (100 MHz, D$_2$O) δ 174.50, 174.25, 102.98, 94.82, 90.47, 79.44, 79.17, 74.72, 73.36, 72.46, 72.40, 70.79, 70.12, 69.94, 69.57, 69.55, 69.49, 69.18, 68.64, 60.11, 59.96, 56.12, 53.71, 50.11, 22.14, 21.84; HRMS: [M+H]$^+$ calcd for C$_{20}$H$_{37}$N$_4$O$_{13}$$^+$, 541.2352; found, 541.2336.

2-Methyl-{6-O-2-[2-(2-azidoethoxy)ethoxy]ethyl-β-D-galactopyranosyl-(1→4)-1,2-dideoxy-α-D-glucopyrano}-[2,1-d]-2-oxazoline (24)

To a solution of compound 23 (5.3 mg, 9.8 μmol) in H$_2$O (200 μL) were added Et$_3$N (30 mol. equiv.) and 2-chloro-1,3-dimethylimidazolinium chloride (DMC, 20 mol. equiv.) at 0° C. The reaction mixture was kept at this temperature for 7 h then purified by gel filtration on a Sephadex G-10 column that was eluted with 0.1% aq Et$_3$N to afford 24 (4.9 mg, 96%) as white solid after lyophilization with aqueous NaOH (0.05 mol. equiv.). $^1$H NMR (400 MHz, D$_2$O) δ 5.98 (1H, d, J=7.3 Hz), 4.31 (1H, d, J=7.8 Hz), 4.29-4.27 (1H, m), 3.80 (1H, d, J=3.1 Hz), 3.74-3.69 (2H, m), 3.67-3.57 (14H, m), 3.56-3.50 (2H, m), 3.42-3.38 (3H, m), 3.36-3.32 (1H, m), 1.96 (3H, s); $^{13}$C NMR (100 MHz, D$_2$O) δ 168.22, 104.68, 99.86, 78.52, 73.50, 72.49, 71.02, 70.79, 70.23, 70.07, 69.57, 69.55, 69.51, 69.37, 69.20, 68.85, 65.29, 61.67, 50.12, 12.90; HRMS: [M+H]$^+$ calcd for C$_{20}$H$_{35}$N$_4$O$_{12}$$^+$, 523.2246; found, 523.2236.

Compound (25). A solution of commercial trastuzumab (100 μg) and oxazoline 6 (14 μg, 20 eq per glycosylation site) was incubated with wild-type Endo-S2 (0.1 μg) at 28° C. in 4 μL of 150 mM PBS buffer (pH=7.0), and the reaction was monitored by LC-MS of aliquots. Within 30 min, LC-MS analysis indicated the completion of the transglycosylation with conversion yield >95%. LC-MS: calculated for whole antibody, M=146909 Da; found (m/z), 146912 (deconvolution data); After IdeS digestion, LC-MS calculated for Fc part, M=24656 Da; found (m/z), 24656 (deconvolution data).

Compound (26). A solution of commercial trastuzumab (100 μg) and oxazoline 14 (10.5 μg, 15 eq per reaction site) was incubated with wild-type Endo-S2 (0.3 μg) at 28° C. in 4 μL of 150 mM PBS buffer (pH=7.0), and the reaction was monitored by LC-MS of aliquots. LC-MS analysis indicated the completion of the transglycosylation with conversion yield >95% within 2 h. LC-MS: calculated for whole antibody, M=146909 Da; found (m/z), 146911 (deconvolution data); After IdeS digestion, LC-MS calculated for Fc part, M=24656 Da; found (m/z), 24656 (deconvolution data).

Compound (27). A solution of commercial trastuzumab (100 μg) and oxazoline 24 (10.5 μg, 15 eq per reaction site) was incubated with wild-type Endo-S2 (0.5 μg) at 28° C. in 4 μL of 150 mM PBS buffer (pH=7.0), and the reaction was monitored by LC-MS of aliquots. LC-MS analysis indicated the completion of the transglycosylation within 2 h, with conversion yield >95%. LC-MS: calculated for whole antibody, M=146909 Da; found (m/z), 146912 (deconvolution data); After IdeS digestion, LC-MS calculated for Fc part, M=24656 Da; found (m/z), 24657 (deconvolution data).

Compound (29).
To a solution of bis-PEG5-NHS (6.0 mg, 11.3 μmol) in anhydrous DMSO (100 μL) was added 28 (3.2 mg, 2.8 μmol) in anhydrous DMSO (100 μL) in 5 portions every 10 min, and Et$_3$N was added to keep the pH=8.5. After the completion of the reaction as monitored by LC-MS, 10% TFA (aq) was added (60 μL), and the reaction mixture was directly purified by preparative-HPLC (gradient, 30-70% aq MeCN containing 0.1% TFA for 40 min, 4 mL/min) to give 29 (3.6 mg, 82%) as white foam. RP-HPLC retention time, t$_R$=22.5 min (gradient, 20-70% aq MeCN containing 0.1% FA for 30 min; flow rate, 0.4 mL/min). ESI-MS [M+H]$^+$ calcd for C$_{76}$H$_{122}$N$_{11}$O$_{22}$$^+$, 1540.88; found, 1541.29; [M+Na]$^+$ calcd for C$_{76}$H$_{121}$N$_{11}$NaO$_{22}$$^+$, 1562.86; found, 1563.28.

Compound (1). To a solution of 5 (1.4 mg, 2.55 μmol) and 29 (2.1 mg, 1.36 μmol) in anhydrous DMSO (40 μL) was added Et$_3$N (0.6 μL) to adjust pH=8.5. The mixture was kept at room temperature until the complete consumption of 29 to give the crude product 30 in DMSO that was directly used in the next step without further purification. RP-HPLC retention time for 30, t$_R$=16.9 min (gradient, 20-70% aq MeCN containing 0.1% FA for 30 min; flow rate, 0.4 mL/min). HRMS: [M+H]$^+$ calcd for C$_{92}$H$_{155}$N$_{12}$O$_{32}$$^+$, 1941.0898; found, 1941.0847. To the residue obtained in the first step was added H$_2$O (80 μL) and Et$_3$N (40 mol. equiv.), the mixture was cooled to 0° C. and 2-chloro-1,3-dimethylimidazolinium chloride (DMC, 30 mol. equiv.) was added. After 12 h at 0° C., the reaction was purified by preparative-HPLC (gradient, 25-60% aq MeCN containing 0.1% NH$_3$·H$_2$O for 40 min, 4 mL/min) to give oxazoline 1 (1.9 mg, 73% for 2 steps) as white foam. HRMS: [M+H]$^+$ calcd for C$_{92}$H$_{153}$N$_{12}$O$_{31}$$^+$, 1922.0759; found, 1922.0703.

Compound (2). To a solution of 12 (1.4 mg, 2.60 μmol) and 29 (2.0 mg, 1.30 μmol) in anhydrous DMSO (40 μL) was added Et$_3$N (0.6 μL) to adjust pH=8.5. The mixture was kept at room temperature until the complete consumption of 29 to give the crude product (31), which was used in the next step without further purification. RP-HPLC retention time for 31, t$_R$=17.1 min (gradient, 20-70% aq MeCN containing 0.1% FA for 30 min; flow rate, 0.4 mL/min). HRMS: [M+H]$^+$ calcd for C$_{92}$H$_{155}$N$_{12}$O$_{32}$$^+$, 1941.0898; found, 1941.0851. To the residue obtained in the first step was added H$_2$O (80 μL) and Et$_3$N (40 mol. equiv.). The mixture was cooled to 0° C. and 2-chloro-1,3-dimethylimidazolinium chloride (DMC, 30 mol. equiv.) was added. After 12 h at 0° C., the reaction was purified by preparative-HPLC (gradient, 25-60% aq MeCN containing 0.1% NH$_3$·H$_2$O for 40 min, 4 mL/min) to give oxazoline 2 (2.0 mg, 80% for 2 steps) as white foam. HRMS: [M+H]$^+$ calcd for C$_{92}$H$_{153}$N$_{12}$O$_{31}$$^+$, 1922.0759; found, 1922.0800.

Compound (3). To a solution of 22 (2.3 mg, 4.14 μmol) and 29 (3.2 mg, 2.07 μmol) in anhydrous DMSO (60 μL) was added Et$_3$N (0.8 μL) to adjust pH=8.5. The mixture was kept at room temperature until the complete consumption of 29 to give the crude product (32), which was used directly for the oxazoline formation without further purification. RP-HPLC retention time for 32, t$_R$=17.1 min (gradient, 20-70% aq MeCN containing 0.1% FA for 30 min; flow rate, 0.4 mL/min). HRMS: [M+H]$^+$ calcd for C$_{92}$H$_{155}$N$_{12}$O$_{32}$$^+$, 1941.0898; found, 1941.0836. To the residue obtained in the first step was added H$_2$O (100 μL) and Et$_3$N (40 mol. equiv.), the mixture was cooled to 0° C. and 2-chloro-1,3-dimethylimidazolinium chloride (DMC, 30 mol. equiv.) was added. After 12 h at 0° C., the reaction mixture was subjected to preparative-HPLC (gradient, 25-60% aq MeCN containing 0.1% NH$_3$·H$_2$O for 40 min, 4 mL/min) to give oxazoline 3

(2.8 mg, 70% for 2 steps) as a white foam. HRMS: [M+H]$^+$ calcd for $C_{92}H_{153}N_{12}O_{31}^+$, 1922.0759; found, 1922.0731.

Compound (33). A solution of commercial trastuzumab (500 µg) and oxazoline 1 (200 µg, 15 eq for glycosylation site) was incubated with wild-type Endo-S2 (1.0 µg) at 28° C. in 25 µL of 150 mM PBS buffer containing 5% of DMSO (pH=7.0). LC-MS monitoring indicated the complete transglycosylation after 1 h. The reaction mixture was diluted with 50 mM PB (3 mL) and filtered by 0.22 µm filter to remove most of the hydrophobic payload, and the residue was purified using protein A chromatography to give the antibody-drug conjugate (33) (470 µg, 95%). LC-MS: calculated for the whole ADC, M=149709 Da; found (m/z), 149709 (deconvolution data); After IdeS digestion, LC-MS calculated for the drug-conjugated Fc monomer, M=26056 Da; found (m/z), 26057 (deconvolution data).

Compound (34). A solution of commercial trastuzumab (500 µg) and oxazoline 2 (250 µg, 20 eq per reaction site) was incubated with wild-type Endo-S2 (10 µg) at 28° C. in 25 µL of 150 mM PBS buffer containing 5% of DMSO (pH=7.0), and the reaction was monitored by LC-MS of aliquots. After 1 h, another portion of oxazoline 2 (60 µg, 5 eq per reaction site) was added to push the reaction. Within 1.5 h, LC-MS analysis indicated the completion of the transglycosylation with a conversion yield of >95%. The reaction mixture was diluted with 50 mM PB (3 mL) and filtered by 0.22 µm filter to remove most of the hydrophobic payload, and the residue was purified using protein A chromatography to give 34 (460 µg, 93%). LC-MS: calculated for the ADC, M=149709 Da; found (m/z), 149708 (deconvolution data); After IdeS digestion, LC-MS calculated for the drug-conjugated Fc monomer, M=26056 Da; found (m/z), 26057 (deconvolution data).

Compound (35). A solution of commercial trastuzumab (500 µg) and oxazoline 3 (250 µg, 20 eq per glycosylation site) was incubated with wild-type Endo-S2 (5 µg) at 28° C. in 25 µL of 150 mM PBS buffer containing 5% of DMSO (pH=7.0), and the reaction was monitored by LC-MS analysis. After 1 h, another portion of oxazoline 3 (60 µg, 5 eq per glycosylation site) was added to push the reaction. Within 2 h, LC-MS analysis indicated the completion of the transglycosylation with a conversion yield of >95%. The reaction mixture was diluted with 50 mM PB (3 mL) and filtered by 0.22 µm filter to remove most of the hydrophobic payload. The residue was purified using protein A chromatography to give 35 (430 µg, 86%). LC-MS: calculated for the ADC, M=149709 Da; found (m/z), 149710 (deconvolution data); After IdeS digestion, LC-MS calculated for the drug-conjugated Fc monomer, M=26056 Da; found (m/z), 26057 (deconvolution data).

Culture conditions. SK-BR-3 cells (ATCC® HTB-30™) were maintained in suspension in McCoy's 5a Medium (ATCC® 30-2007) containing 10% fetal bovine serum (FBS, not heated), 100 U/mL penicillin and 100 µg/mL streptomycin in T-75 flasks (CELLTREAT). BT474 cells (ATCC® HTB-20™) were maintained in suspension in Hybri-Care Medium (ATCC® 46-X) containing 10% bovine serum (FBS), 100 U/mL penicillin and 100 µg/mL streptomycin in T-75 flasks (CELLTREAT). T47D cells (ATCC® HTB-133™) were maintained in suspension in RPMI-1640 Medium (ATCC® 30-2001) containing 10% fetal bovine serum (FBS), 4 mg/L insulin, 100 U/mL penicillin and 100 µg/mL streptomycin in T-75 flasks (CELLTREAT).

Cytotoxicity assays. For SK-BR-3 and T47D cell lines, the cells were plated into 96-well plates with 10,000 cells per well. These plates were incubated overnight at 37° C. and 5% $CO_2$. Serial 3-fold dilution was applied to the ADC samples with the corresponding medium from 5000 ng/mL to 0.085 ng/mL. The samples were added to three wells (150 µL per well) with every single concentration and the cells were cultured at 37° C. and 5% $CO_2$ for three days before the addition of Cell Counting Kit-8 (Sigma). The absorbance of formazan released by viable cells was measured at 450 nm using a spectrophotometer after incubation for 2-3 h at 37° C. and 5% $CO_2$. Finally, the $EC_{50}$ values and the cell viability curve were calculated by GraphPad Prism software. For the BT474 cell line, the cells were plated into 96-well plates with 4,000 cells per well. These plates were incubated overnight at 37° C. and 5% $CO_2$. Serial 3-fold dilution was applied to the ADC samples with the corresponding medium from 5000 ng/mL to 0.085 ng/mL. The samples were added to three wells (200 µL per well) with every single concentration and the cells were cultured at 37° C. and 5% $CO_2$ for six days before the addition of Cell Counting Kit-8 (Sigma). The absorbance of formazan released by viable cells was measured at 450 nm using a spectrophotometer after incubation for 2-3 h at 37° C. and 5% $CO_2$. Finally, the $EC_{50}$ values and the cell viability curve were calculated by GraphPad Prism software.

Example 3

Figure 31:
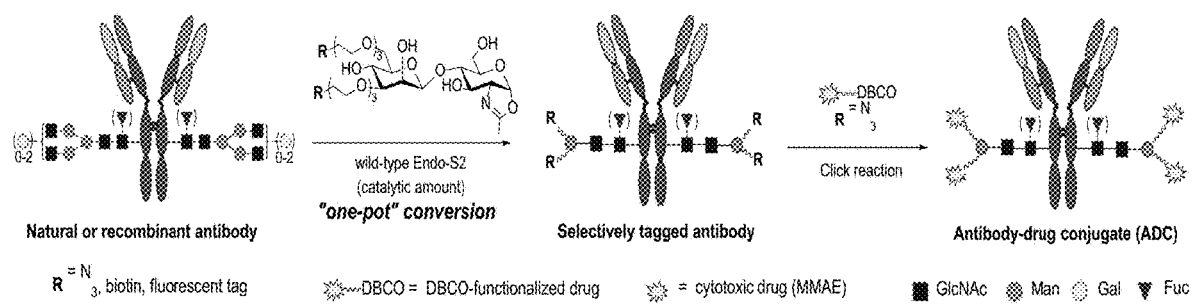
FIG. 31. One-pot and site-specific labeling and conjugation of antibodies enabled by simultaneous deglycosylation and transglycosylation with wild-type Endo-S2.

Described in this Example is the design, synthesis, and evaluation of a series of simple disaccharide oxazoline derivatives modified with different functional groups and the evaluation of them as donor substrates for antibody glycoengineering. The substrate specificity of different endoglycosidases (Endo-S, Endo-S2, Endo-F3, Endo-A, Endo-CC, and their mutants) toward these synthetic substrates in glycan remodeling of therapeutic antibodies, using trastuzumab (Herceptin) as a model antibody was studied. It was found that wild-type Endo-S2 exhibited the best activity in transferring the functionalized disaccharides with site-selectively modified azide, biotin, or fluorescent tags to antibodies, but the transglycosylation products, once formed, were resistant to hydrolysis by the wild-type enzyme, due to the truncated modifications. Combining with the excellent Fc deglycosylation activity of Endo-S2, a simple one-pot deglycosylation and transglycosylation method was devised for direct labeling and functionalization to give structurally well-defined and homogeneously tagged antibodies (FIG. 31). The site-specific introduction of varied numbers of azide groups enabled a highly efficient synthesis of homogeneous ADCs with precise control of the DARs via a copper-free strain-promoted click reaction. Cytotoxicity assays showed that ADCs with higher DARs were more potent in killing antigen-overexpressed cells than those with lower DARs.

Results

Figure 32:
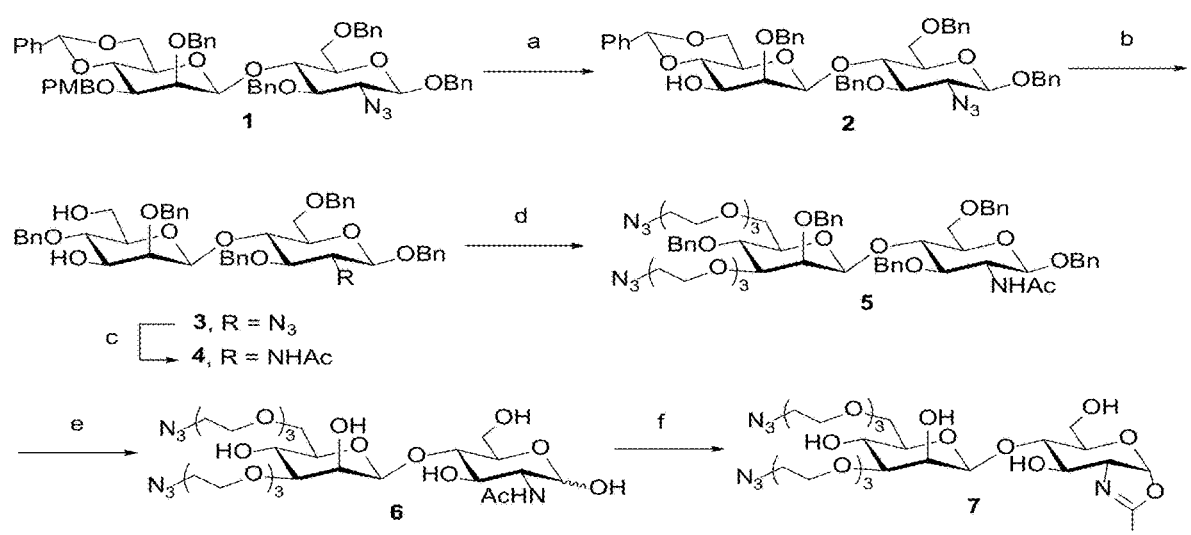
FIG. 32. Scheme 1. Synthesis of Disaccharide Oxazoline 7 Carrying Two Azide Tags. aReagents and conditions: (a) DDQ, CH2Cl2/H2O, 0° C.~RT, and 90%; (b) BH3·THF, Bu2BOTf, CH2Cl2, 0° C., and 94%; (c) AcSH, pyridine/CHCl3, RT, and 82%; (d) N3(CH2CH2O)3Ts, NaH, DMF, 0° C.~RT, and 78%; (e) NaBrO3, NaS2O4, EtOAc/H2O, RT, and 65%; and (f) DMC, Et3N, H2O, 0° C., and 90%

Chemical Synthesis of the Azido-Tagged Disaccharides. While it has been shown that smaller synthetic disaccharide oxazolines could serve as substrates of endoglycosidases Endo-A and Endo-M for transglycosylation (Zeng et al, 2006 Eu J 12:3355-3364) it is not clear whether these antibody-specific ENGases and their mutants can recognize the smaller substrates for trans-glycosylation using antibodies as acceptors. To test this hypothesis, a series of azido-tagged disaccharide oxazolines were synthesized. Considering the flexibility and solubility of PEGs, it was decided to introduce azido groups with PEG-derived scaffolds. Recently, Mizuno and co-workers have shown that PEGylated sugar oxazolines could serve as donor substrates of Endo-M for transglycosylation (Goto K et al., 2020 Tetrahedron Lett. 61:151475). Thus, a Manβ1,4GlcNAc oxazoline carrying two azide groups was designed as a first target, in which the PEG-linkers resembled the natural glycan branches, so that it might be recognized favorably by the endoglycosidases (FIG. 32; Scheme 1). The synthesis was started with the known disaccharide 1 (Ochiai et al., 2008 J Am Chem Soc 130:13790-13803) through selective removal of the PMB group with DDQ, giving 2 in 90% yield. Regioselective reductive ring-opening reaction on the benzylidene acetal of 2 provided the diol 3. After conversion of the azido group to an acetamido group with AcSH to afford 4, two azide-tagged polyethylene chains were introduced at the 3' and 6' positions of the disaccharide by treatment of 4 with NaH and $N_3(CH_2CH_2O)_3Ts$, giving 5 in 78% yield. To selectively remove the benzyl groups in the presence of azides, a biphasic oxidative condition ($NaBrO_3/Na_2S_2O_4$) was adopted (Niemietz M et al., 2011 47:10485-10487) which furnished the desired free disaccharide derivative 6 in 65% yield. Finally, oxazoline formation was achieved in a single step by treatment of 6 with an excess amount of 2-chloro-1,3-dimethylimidazolinium chloride (DMC) and TEA in water, affording the desired disaccharide oxazoline 7 carrying two azide groups in 90% isolated yield.

Figure 33:
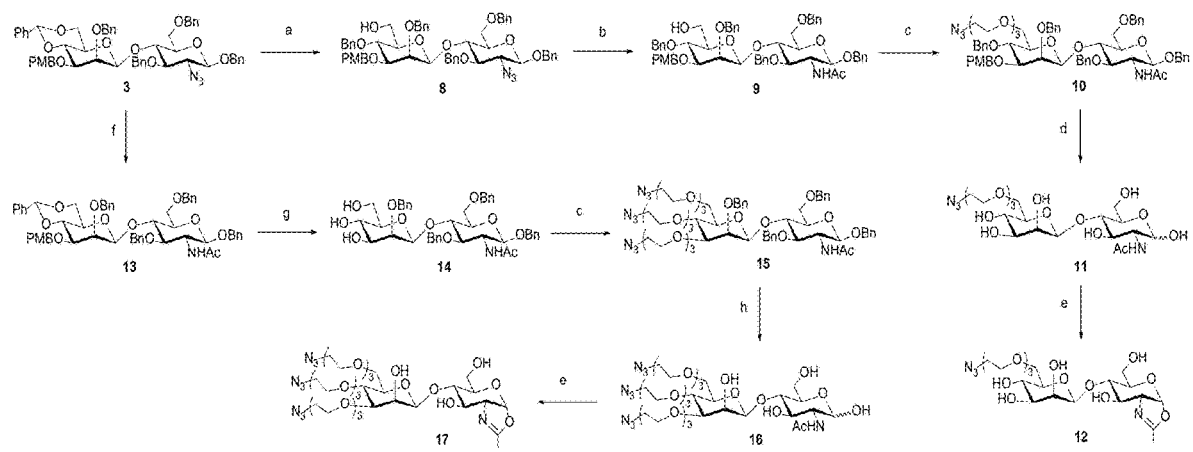
FIG. 33. Scheme 2. Synthesis of Disaccharide Oxazolines 12 and 17 Carrying One or Three Azide TagS. Reagents and conditions: (a) BH3·THF, Bu2BOTf, CH2Cl2, 0° C., and 91%; (b) AcSH, pyridine/CHCl3, RT, and 84%; (c) N3(CH2CH2O)3Ts, NaH, DMF, 0° C.~RT, 10, 89%, 15, and 73%; (d) NaBrO3, NaS2O4, EtOAc/H2O, RT, and 90%; (e) DMC, Et3N, H2O, 0° C., 12, 90%, 17, and 85%; (f) AcSH, pyridine/CHCl3, 60° C., and 85%; (g) TFA, CH2Cl2, −20-0° C., and 82%; (h) Pd/C, H2, HCl (aq), THF/H2O, then, TfN3, K2CO3, CuSO4, CHCl2/MeOH/H2O, RT, and 66%.
Figure 34:
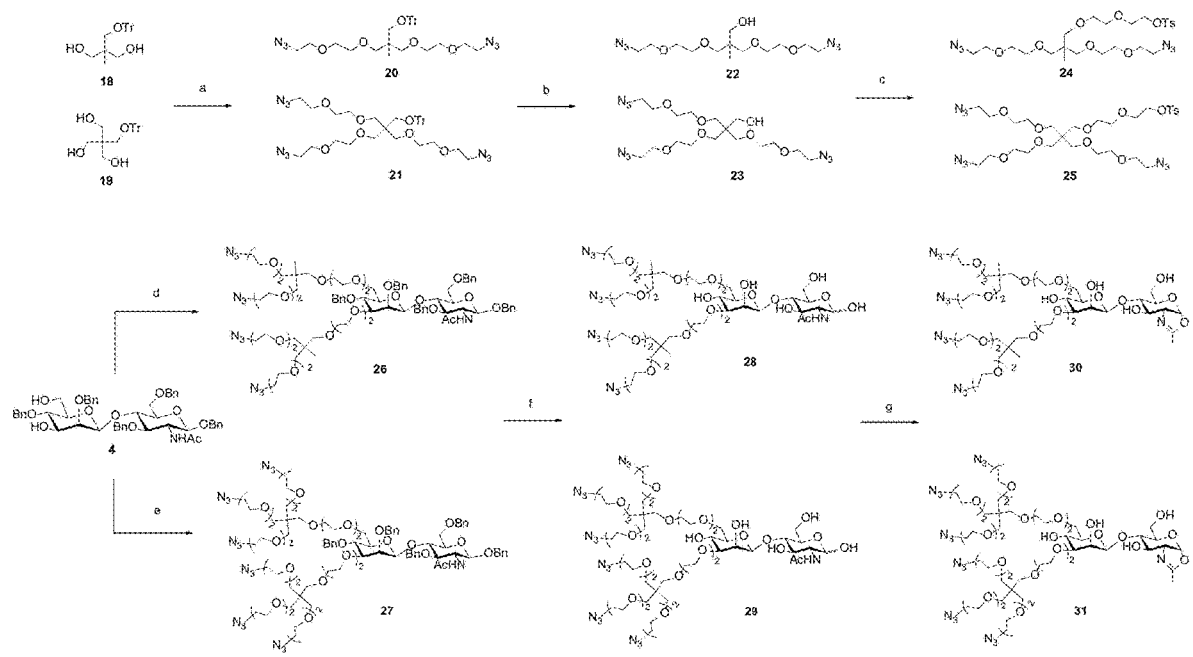
FIG. 34. Scheme 3. Synthesis of Disaccharide Oxazolines 30 and 31 Carrying Four or Six Azide Tags. aReagents and conditions: (a) N3(CH2CH2O)2Ts, NaH, DMF, and 0° C.~RT; (b) TsOH, MeOH, 60° C., 20, 72% for two steps, 21, and 54% for two steps; (c) TsO(CH2CH2O)2Ts, NaH, DMF, 0° C.~RT, 22, 85%, 23, and 72%; (d) 24, NaH, DMF, 0° C.~RT, and 78%; (e) 25, NaH, DMF, 0° C.~RT, and 74%; (f) Pd/C, H2, HCl (aq), THF/H2O, then TfN3, K2CO3, CuSO4, CH2Cl2/MeOH/H2O, RT, 28, 67%, 29, and 59%; and (g) DMC, Et3N, H2O, 0° C., 30, 89%, 31, and 84%.

Next, the disaccharides were synthesized with one or three azido groups (FIG. 33; Scheme 2). The 6-position of the mannose residue was selected for the introduction of a single azido-ended PEG linker. Regioselective ring-opening of 3 smoothly exposed the hydroxyl group to obtain disaccharide 8. After the reduction of the azido group to an acetamido group, the PEG-spaced azide group was introduced in high yield to afford 10. Selective debenzylation under oxidative conditions proved to be efficient, giving the free disaccharide 11 in 90% yield, which was converted to oxazoline 12 after treatment with DMC/TEA in water. In parallel, the synthesis of a three azido-tagged disaccharide also started from 3. Upon the reduction of the azido group to the acetamido group, the benzylidene and PMB groups were simultaneously removed under acidic conditions (Ochiai et al., 2008 J Am Chem Soc 130:13790-13803) yielding 14 with a free hydroxyl group at the 3',4', and 6' positions. Next, the azide-terminated PEG chains were introduced at the three free hydroxyl groups to yield 15. Following the same debenzylation conditions, it was found that the reaction proceeded very fast, but the desired product was isolated in low yield along with some decomposed byproducts as monitored by ESI-MS. It was speculated that the increase in the PEG component resulted in higher water solubility; thus, the partially deprotected intermediate migrated to the aqueous phase and directly interacted with the free radical (Adinofi et al. 1999 Tetrahedron Lett 40:8439-8441) which led to a rapid reaction but undesired products. To address this issue, we attempted a two-step deprotection method (Ochiaia et al., 2008 J Am Chem Soc 130:13790-13803). First, the benzyl groups in 15 were removed by catalytic hydrogenation. Under these conditions, the azido groups were simultaneously reduced to amino groups, which were then transformed back to azido functionality by the copper-catalyzed diazo transfer reaction, 52 giving 16 in 66% yield in two steps. Finally, standard oxazoline formation by treatment of 16 with DMC/TEA in water gave the disaccharide 17 carrying three azide groups in excellent yield (FIG. 33; Scheme 2).

Chemical Synthesis of the Disaccharide Derivatives Carrying a Cluster of Azide Groups. Previous studies have demonstrated that ADCs with higher DARs tend to provide increased target cell killing potency (Strop et al., 2015 Nat. Biotechno 33:694-696; Lyon et al., 2015 Nat Biotechnol 33:733-735). In a handful of cases, a DAR as high as 8 has been achieved through the use of hydrophilic linker payloads, as exemplified with clinically approved Enhertu and Trodelvy (Lyon et al., 2015 Nat Biotechnol 33:733-735; Barida et al., 2019 N Eng J Med 380:741-751; Viricel et al., 2019 Chem Sci 10:4048-4053). To equip antibodies with more biorthogonal tags, we designed disaccharides carrying four or six azido groups. The synthesis commenced with the branched scaffolds (FIG. 28; Scheme 3). First, the diol 18 (Linclau et al., 2012 Ange Chem Int Ed 51:1232-1235) and triol 19 (Tanaka et al., 2008 Chem Lett 37:440-441) were extended by an azido-ended linker, which, respectively, furnished 22 and 23 after the removal of the trityl group. The exposed OH in 22 and 23 was further extended with a bistosyl linker to give 24 and 25, respectively, which were ready for conjugation. Next, disaccharide 4, which carries free hydroxyl groups at the 4' and 6' positions, was reacted with the tosyl derivatives (24 and 25) in the presence of NaH, giving 26 and 27, respectively. Finally, the two-step deprotection followed by oxazoline formation gave disaccharide oxazolines 30 and 31 carrying four and six azido groups, respectively (FIG. 28; Scheme 3).

Figure 29:
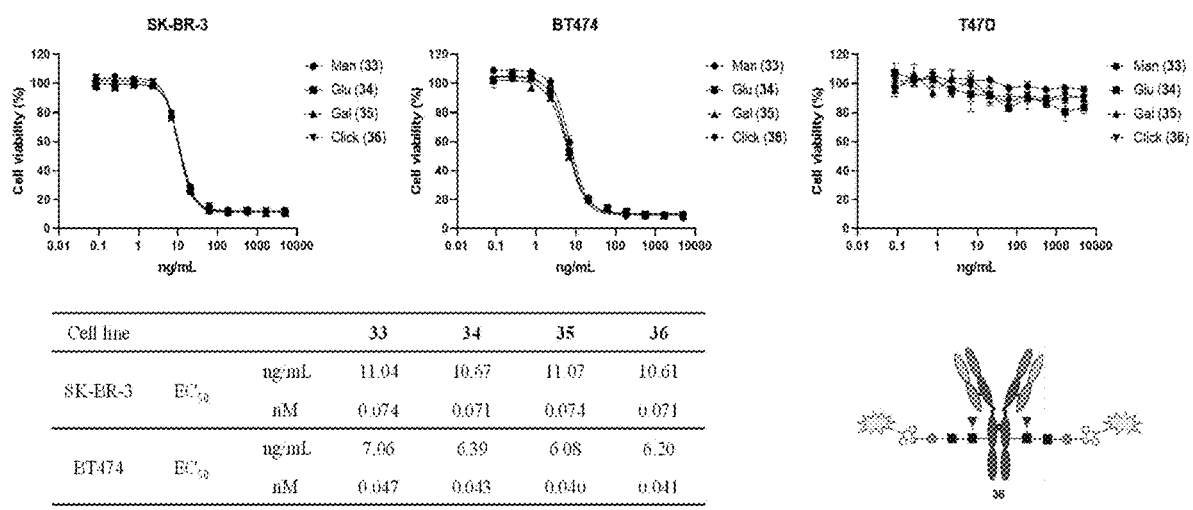
FIG. 29. Cell killing studies in breast cancer cell line SK-BR-3, BT474 (HER2 overexpression) and T47D (HER2 low expression). All assays were performed in triplicate.

Evaluation of the Synthetic Disaccharide Oxazolines as Donor Substrates for Enzymatic Antibody Glycan Remodeling. With the disaccharide oxazolines in hand, their suitability as donor substrates for antibody-glycan remodeling was tested by the catalysis of different endoglycosidases. For the purpose, trastuzumab was chosen, an anti-Her2 antibody (Herceptin), as a typical monoclonal antibody and the synthetic disaccharide oxazoline (7) carrying two PEG-spaced azide groups as the donor substrate to examine the enzymatic reactions. The results are summarized in FIG. 29. Trastuzumab (Herceptin) was first deglycosylated with wild-type Endo-S2 to provide the Fucα1,6GlcNAc glycoform of Herceptin as the acceptor (32). (Li et al., 2016 J Biol Chem 291:16508-165518)

Among the endoglycosidases tested, it was found that Endo-S2,58 an endoglycosidase from *Streptococcus pyogenes* of serotype M49 (Endo-S2) with relaxed substrate specificity, exhibited remarkable activity toward the azido-tagged disaccharide oxazoline 7 for transglycosylation. With only a catalytic amount of enzyme (0.1%, w/w, enzyme/antibody) and 20 mol equivalents of the azido-disaccharide oxazoline, the reaction could reach completion within 1 h under mild conditions [rt, phosphate-buffered saline (PBS) buffer, and pH 7.0]. It was found that the transglycosylation product (33), once formed, was largely resistant to hydrolysis by the wild-type enzyme, mainly due to truncated modifications. The Endo-S2 mutant (D184M), a glycosynthase with broad substrate specificity and diminished hydrolytic activity (Li et al., 2016 J Biol Chem 291:16508-165518).

It was also tested and found that the D184M mutant could also use the azide-disaccharide oxazoline for transglycosylation, but the activity was lower than that of the wild-type enzyme, and a relatively large amount of the mutant enzyme (1%, w/w) was required to drive the reaction. Again, the transglycosylation product was not hydrolyzed by the mutant, allowing accumulation of the product. Next, wild-type Endo-S, the first endoglycosidase from *Streptococcus pyogenes* that shows Fc-specific deglycosylation activity was tested. (Goodfellow et al., 2012 J Am Chem Soc 134:8030-8033; Collinet al., 2001 EMBO J 20:3046-3055) Endo-S could transfer the modified disaccharide oxazoline (7), but, in contrast to wild-type Endo-S2, at least 10-fold more enzyme was required to drive the reaction. Similarly, the Endo-S D233Q mutant, which was a glycosynthase that could act efficiently on complex type N-glycan oxazoline and azido-Man3GlcNAc oxazoline corresponding to the N-glycan core for Fc glycan remodeling (Huang et al., 2012 J Am Chem Soc 134:12308-12318) just showed very low activity on 7, probably because the minimal structure and the modification made it a poor substrate for the enzyme.

In addition to Endo-S2 and Endo-S, several other endoglycosidases were tested. Endo-F3 is an endoglycosidase from *Elizabethkingia meningoseptica* that efficiently hydrolyzes core-fucosylated complex-type N-glycans (Tarentino et al., 1995 Glycobiology 5:599-601). It has been previously reported that wild-type Endo-F3 and its mutant Endo-F3 D165A can transfer with complex-type glycan oxazoline and core Man3GlcNAc oxazoline for N-glycopeptide synthesis and antibody glycan remodeling (Huang et al., 2011 Chem Bio Chem 12:932-941: Giddens et al., 2018 Proc Natl Acad USA 115:12023-12027: Giddens et al., 2016 J Biol Chem 291:9356-9370). However, it was found that neither wild-type Endo-F3 nor its glycosynthase mutant (D165A) could efficiently act on the azido-tagged disaccharide oxazoline for transglycosylation. As for endoglycosidases Endo-A (from *Arthrobacter protophormiae*) (Takegawa et al., 1997 Arch-Biochem Biophys 338:22-28; Ochiai et al., J Am Chem Soc 130:13790-13803) Endo-D) Fan et al., 2012 J Biol Chem 287:11272-11281) and Endo-CC (Eshima et al, 2015 PLoS One 10 No e0132859) it was found that they were not able to transfer the azide-disaccharide oxazoline (7) to the Fucα1,6GlcNAc-Herceptin. This is expected, as these three endoglycosidases cannot accept core-fucosylated GlcNAc as an acceptor. To test if nonfucosylated GlcNAc-Herceptin could serve as an acceptor, the core-fucose was removed from the Fucα1,6Glc-NAc-Herceptin (32) by treatment with an α-fucosidase (BfFucH) to produce the nonfucosylated Fc glycoform. However, Endo-A, Endo-D, and Endo-CC were not able to show the transglycosylation product, as monitored by LC-ESI-MS analysis, when even a large amount of enzyme (10%, w/w) was used (FIG. 35). These studies established wild-type Endo-S2 as a remarkably efficient endoglycosidase to act on the azido-tagged disaccharide oxazoline for transglycosylation without product hydrolysis.

Figure 36:
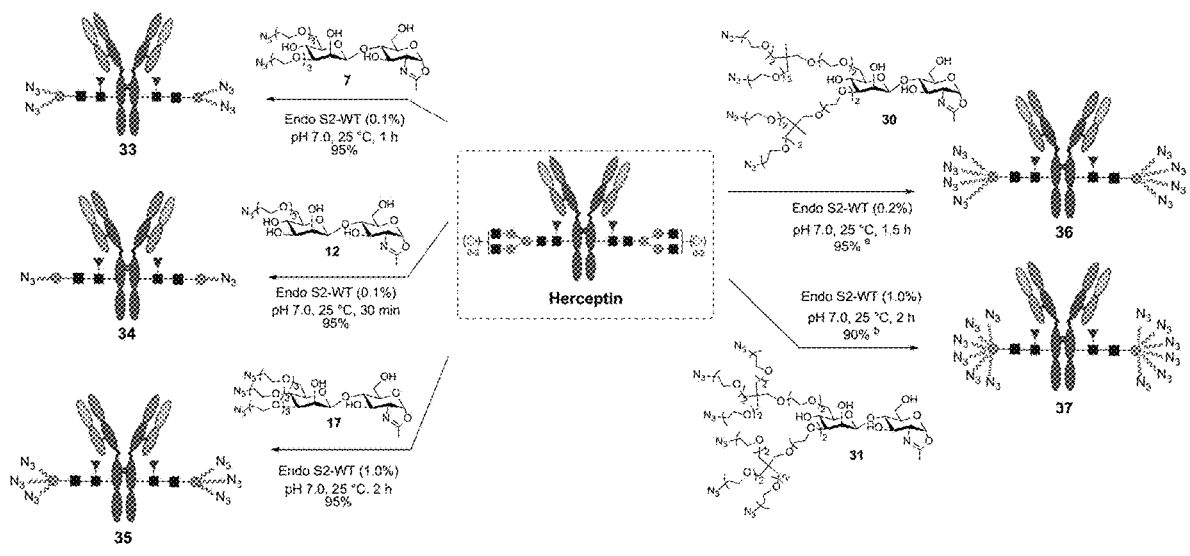
FIG. 36. Scheme 4. One-Pot Transglycosylation with Different Azido-Tagged Disaccharide Oxazolines. Reagents and conditions: the reactions were conducted with 20 equiv oxazolines in PBS buffer at 25° C.; (a) one additional portion of oxazoline (10 equiv) was added after 1 h; (b) three more portions of oxazoline (10 equiv each) were added every 30 min.

One-Pot Chemoenzymatic Fc Glycan Remodeling with Different Azido-Tagged Disaccharide Oxazolines using Wild-Type Endo-S2. Given the observation that wild-type Endo-S2 could act on the minimal azido-disaccharide oxazoline for efficient transglycosylation without product hydrolysis and the fact that Endo-S2 is highly active for antibody Fc deglycosylation, it was envisioned that a "one-pot" and site-specific Fc glycan remodeling of antibodies should be possible to produce homogeneous azido-tagged antibody glycoforms. Indeed, when commercial Herceptin was treated with Endo-S2 together with the azido-disaccharide oxazoline (7) at rt in a PBS buffer (pH 7.0), LC-ESI-MS monitoring indicated that the Herceptin deglycosylation was complete within 10 min, followed by the appearance and accumulation of the transglycosylation product (33). The transglycosylation was complete within 1 h under the described conditions (FIG. 36; Scheme 4) to give essentially quantitative transformation without the need of isolating the intermediates. The one-pot reactions was then tested with other synthetic disaccharide oxazolines carrying varied numbers of azide functional groups. Although these azide-functionalized disaccharide derivatives showed different activities toward wild-type Endo-S2, with the heavily functionalized disaccharide being less active, it was found that all of them could serve as donor substrates for Endo-S2-catalyzed transglycosylation and excellent yields were obtained in a one-pot manner within 1-3 h when the enzyme amount was adjusted (0.1-1.0%, w/w); FIG. 36; Scheme 4). Notably, one portion of oxazoline was enough to achieve complete conversion for the disaccharides carrying one-three azido groups, because 7 and 12 were such good substrates that the transglycosylation could be finished within 1 h, whereas 17 was resistant to hydrolysis, and as a result, a relatively larger amount of enzyme but no additional oxazoline was needed. However, for the disaccharide carrying four (30) or six (31) azido groups, an additional portion of oxazoline was necessary to drive the reaction to completion due to the moderate hydrolytic activity of Endo-S2 toward these oxazo-line donors. The final product was isolated by the protein A affinity column, and their identity and homogeneity were confirmed by LC-ESI-MS analysis of the intact whole antibody and the Fc domain glycoforms after IdeS treatment to disconnect the Fab and Fc domains. It should be mentioned that in the case when a large excess of glycan oxazolines were used to drive the reaction, the excess glycan oxazoline could be recovered in the form of free oligosaccharide during protein A purification, which could be further purified by RP-HPLC and then converted into the glycan oxazoline in a single step with DMC/TEA, thus permitting the recycling of glycan oxazoline for transglycosylation.

One-Pot Chemoenzymatic Fc Glycan Remodeling with Biotin- and Fluorophore-tagged Disaccharide Oxazolines. Encouraged by the one-pot introduction of the azido functionality, it was investigated whether one could directly transfer a more complex structure, such as biotin- or fluorophore-tagged disaccharide, to an intact antibody with Endo-S2; in this way, the antibody could be labeled in one step, which would be attractive for diagnostics and in vivo imaging and as tools for molecular biology (Freise et al., 2015 Mol Immunol 67:142-152; Zhou et al., 2017 Biomedicines 5:64; Boeggeman et al., 2009 20:1228-1236). To this end, biotin or TAMRA was introduced to the disaccharide, either via amine coupling reaction (39) or click chemistry (40), and it was found that the modified disaccharide oxazolines could still serve as good substrates of Endo-S2. The biotinylated disaccharide was transferred to the intact antibody to give 41 in 95% yield within 1.5 h with the catalytic amount of enzyme (0.1%, w/w), and the TAMRA-tagged disaccharide oxazoline could afford about 85% of product (42) if additional portions of oxazoline were added (FIG. 37; Scheme 5). Taken together, the chemoenzymatic remodeling method described here showed great potential for one-step labeling of intact antibodies.

Synthesis of Structurally Well-Defined, Homogeneous ADCs by Copper-free Strain-Promoted Click Reactions. With these azido-tagged antibodies in hand, next, click chemistry was tried to make ADCs, using monomethyl auristatin E (MMAE) as a model warhead, a microtubule-disrupting agent that has been used for making the FDA-approved ADCs (FIG. 38; Scheme 6) (Walsh et al., 2021 Chem Soc Rev 50:1305-1353; do Pazo et al., 2021 Nat Rev Drug Discovery 20:853584). The dibenzoazacy-clooctyne (DBCO)-ended MMAE derivative with a cleavable dipeptide linker was incubated with the azido-tagged antibodies, and the reactions were monitored by LC-ESI-MS. It was found that the click chemistry gradually afforded the desired compounds (43-47). Take the reaction between 8N$_3$-modified Herceptin (36) and DBCO-PEG5-VC-PAB-MMAE as an example. All the eight sites were conjugated with drugs within 20 h as indicated by LC-ESI-MS (FIG. 39). To further verify that the drugs were specifically conjugated to the Fc domain, the product was digested with the protease IdeS followed by LC-ESI-MS analysis (Anami et al., 2018 Nat Commun 9:2512). The results showed that the shift of molecular weight was consistent with the attached payloads (calculated for the Fc domain glycoform, M=32,140; observed, 32,143, deconvoluted data), thus confirming the structure of the product. Notably, ion fragments (asterisked peaks in FIG. 39) derived from the whole antibody or Fc domain were detected in ESI-MS analysis, which corresponded to a loss of the drug fragment (~762 Da) that has been reported in previous studies. (Anami et al., 2018 Nat Commun 9:2512; Anami et al, 2017 Org Biomol Chem 15:5635-5642). Finally, the Man3-derived antibody carrying four azido groups was also conjugated with the payloads, affording another DAR4-ADC (48) that allowed us to investigate the influence of different components (FIG. 38; Scheme 6).

Figure 40:
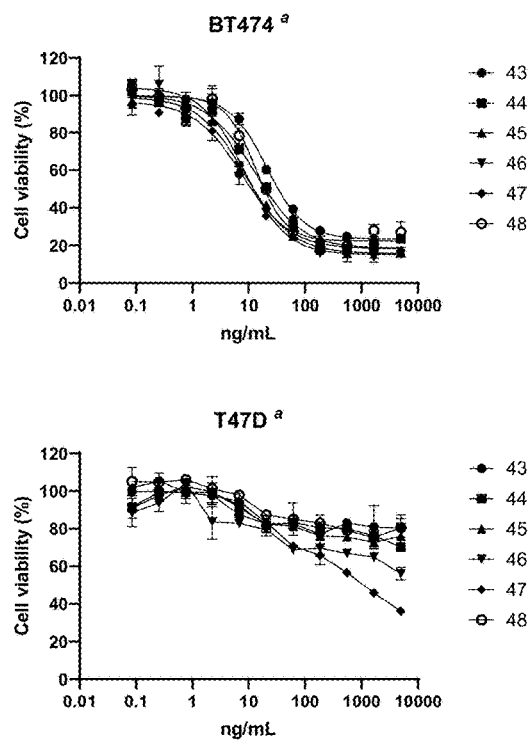
FIG. 40. Cell killing studies in the breast cancer cell line BT474 (HER2 overexpression) and T47D (HER2 low expression). All assays were performed in triplicate. [a]Representative results of two independent assays. [b]Average of two independent assays for the BT474 cell line.
Figure 41:
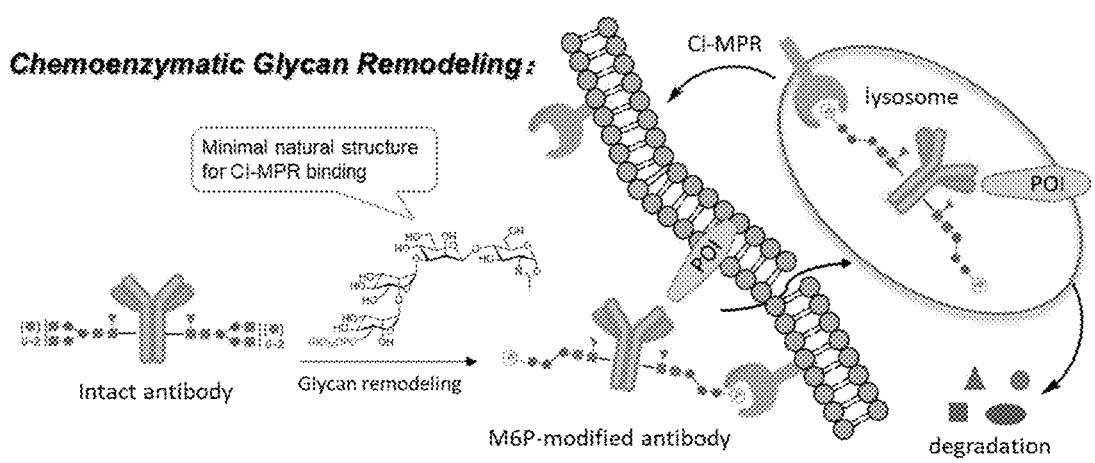
FIG. 41. Chemoenzymatic Glycan Remodeling
Figure 44:
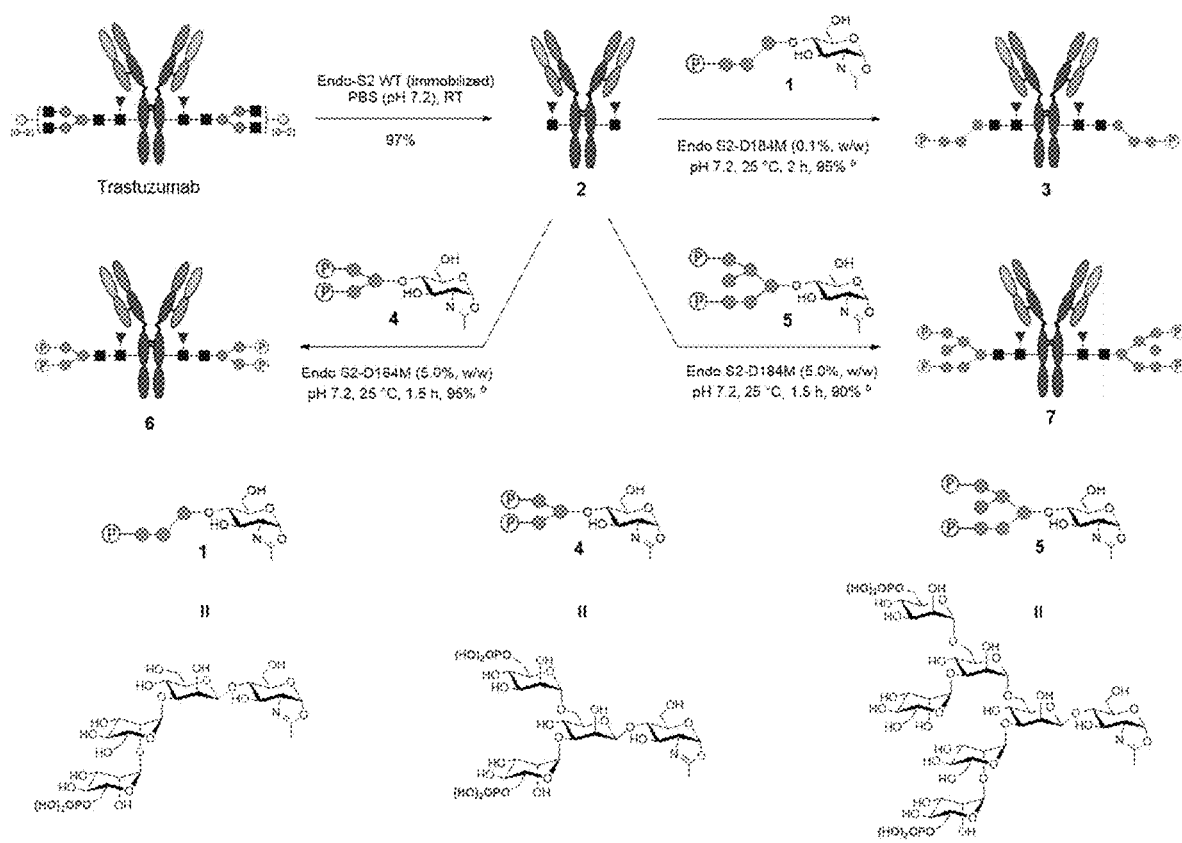
FIG. 44. Scheme 1. Chemoenzymatic glycan remodeling of trastuzumab with phosphorylated glycan oxazolines. The reactions were conducted in PBS buffer and the yields were based on protein A purification. a. 10 eq of oxazoline with antibody concentration of 10 mg/mL; b. 30 eq of oxazoline with antibody concentration of 20 mg/mL.
Figure 45:
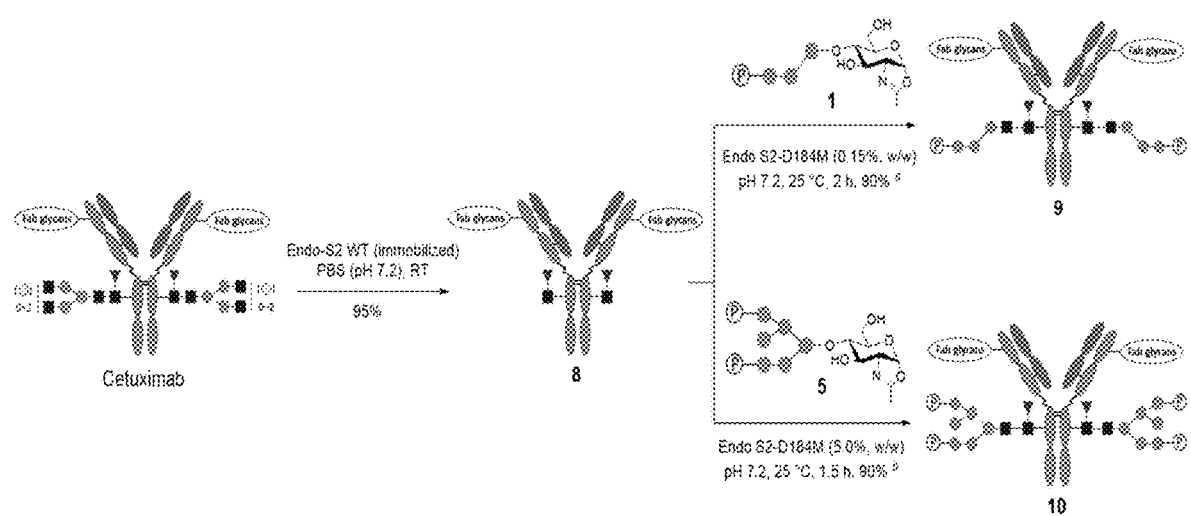
FIG. 45. Scheme 2 Chemoenzymatic glycan remodeling of cetuximab. The reactions were conducted in PBS buffer and the yields were based on protein A purification. a. 10 eq of the glycan oxazoline (1) and an antibody concentration of 10 mg/mL were used. b. 30 eq of the glycan oxazoline (5) and an antibody concentration of 20 mg/mL were used.

Comparative Study of the Cancer Cell Killing Potency of the ADCs with Different DARs. To demonstrate the potency of ADCs with different DARs, cytotoxicity assays in breast cancer cell lines expressing high or low levels of HER2 were conducted. The results showed that all the ADCs achieved significant cell killing of the high target (HER2)-expressing cell line BT474- and ADCs with higher DARs were more potent, as indicated by the half-maximal effective concentration (EC50) values (FIG. 40). It was found that the potency of the ADCs for cell killing was proportional to the DAR of the ADCs. For example, the EC50 of 44 (0.104 nM) was reduced to about a half of that of 43 (0.170 nM) when the DAR increased from 2 to 4; the EC50 of 46 (0.080 nM) was reduced to about threefold of that of 43 when the DAR was increased from 2 to 8 (FIG. 40). These results are consistent with the previously reported observation, where site-specifically conjugated ADCs with varied DARs (2-8) are compared. 13 In addition, the site-specific high-loaded ADC (e.g., DAR8) is substantially more efficacious than the low-loaded ADC (e.g., DAR2) in a mouse xenograft model.13 On the other hand, no substantial killing was observed in the T47D cell line that expresses a low level of HER2 by ADCs with DAR 2-6 under the tested concentrations, indicating the high selectivity of the ADCs for the target cells. However, for ADCs with higher DARs, non-specific cell killing was observed under high concentrations especially for the ADC (47) with DAR12, which was not surprising since ADCs carrying multiple hydrophobic linkers tended to attach to the cell surface nonspecifically, resulting in cytotoxicity to normal cells independent of specific antigen expression. Swapping with hydrophilic payloads might be a solution to overcome the nonspecific cell killing. Taken together, the results indicate that ADCs made by this method carrying 6-8 payloads per antibody might result in an optimal potency and safety profile. In addition to ADCs, the azido-tagged antibodies described here can be also used for other antibody conjugations, such as site-selective construction of antibody-enzyme conjugates (Gray et al., 2020 Nat Chem Biol 16:1376-13840; Xiao et al., Proc Natl Acad Sci USA 2016 113:10304-10309), antibody-cell conjugates, (Wang et al., 2021 ACS Chem Bio 16:724-730; Li et al., 2018 ACS Cent Sci 4: 1633-1641) antibody-antibiotic conju-gates (Lehar et al., Nature 2015 527:323-328), and lysosome-targeting chimeras for targeted protein degradation (Ahn et al., Nat Chem Biol 17:937-946; Banik et al., 2020 Nature 584:291-297; Zhou et al., 2021 ACS Cent Sci 7:499-506; Powell et al., 2021 ACS Infect Dis 7:2050-2067)

Accordingly, a general and robust chemoenzymatic method for Fc glycan-mediated antibody labeling and conjugation is established. This method is enabled by the design, synthesis, and evaluation of various functionalized disaccharide oxazolines as donor substrates for Fc-specific endoglycosidase-catalyzed transglycosylation. The discovery that wild-type Endo-S2 exhibited excellent activity toward various selectively modified disaccharide oxazolines for transglycosylation, yet the resulting modified antibodies were resistant to enzymatic hydrolysis due to the modifications has led to a general platform for site-specific antibody labeling and conjugation. In particular, the relaxed substrate specificity of Endo-S2 allows direct labeling of antibodies with azide-, biotin-, or fluorescent tags, making it possible to achieve single-step labeling of intact antibodies in a site-selective manner. The flexibility to introduce varied numbers of azide functional groups provides a general and robust strategy to produce homogeneous ADCs with well-defined DARs ranging from 2 to 12. Since all the IgG antibodies carry highly conserved Fc-N-glycans, it is expected that this general Fc-glycan-mediated labeling and conjugation method will find wide applications not only for antibody-drug conjugation but also for cell labeling, imaging, and diagnosis.

Materials and Methods

Chemical Synthesis of Glycan Substrates. General. All chemicals, reagents, and solvents were purchased from Sigma-Aldrich and TCI and unless specially noted applied in the reaction without further purification. Thin-layer chromatography was performed using silica gel on glass plates (Sigma-Aldrich), and spots were detected under UV light (254 nm) and then charred with 5% (v/v) sulfuric acid in EtOH or cerium molybdate stain followed by heating at 150° C. Silica gel (200-425 mesh) for flash chromatography was purchased from Sigma-Aldrich. NMR spectra were recorded on a 400 MHz spectrometer (Bruker, Tokyo, Japan) with CDCl3 or D2O as the solvent. The chemical shifts were assigned in ppm, and multiplicities are indicated by s (singlet), d (doublet), t (triplet), q (quartet), and m (multiplet). Coupling constants (J) are reported in Hertz. MALDI-TOF was performed on a Bruker Autoflex speed mass spectrometer in the positive reflectron mode with DHB (ACN/H2O=1:1) as the matrix. HRMS was performed on an Exactive Plus Orbitrap mass spectrometer (Thermo Scientific) equipped with a C18 column. Preparative HPLC was performed with a Waters 600 HPLC instrument and Waters C18 columns (7.0 m, 19×300 mm). The column was eluted with a suitable gradient of MeCN—H2O containing 0.1% FA at a flow rate of 10 mL/min. The detailed procedures for the chemical synthesis of the disaccharide derivatives and other small-molecule compounds (1-31, 39, and 40) are provided in the Supporting Information of (ACS Chem Biol 2021 Nov. 19; 16(11) incorporated herein in its entirety. The syntheses of antibody conjugates are described below.

Preparation of Azido-, Biotin-, or TAMRA-Functionalized Antibodies. General. LC-MS analysis was performed on an Ultimate 3000 HPLC system coupled to an Exactive Plus Orbitrap mass spectrometer (Thermo Fisher Scientific) with a C4 (whole antibody, gradient, 5-95% aq MeCN containing 0.1% FA for 6 min, 0.4 mL/min) or C8 (IdeS digestion, gradient, 25-35% aq MeCN containing 0.1% FA for 6 min, 0.4 mL/min, or 5-95% aq MeCN containing 0.1% FA for 6 min, 0.4 mL/min) column. Deconvolution data were transformed using MagTran software.

Synthesis of 33 (FIG. 36). A solution of commercial Herceptin (1.0 mg) and oxazoline 7 (186 μg, 20 eq per reaction site) was incubated with wild-type Endo-S2 (1.0 μg) at 25° C. in 40 μL of 150 mM PBS buffer (pH=7.0), and the reaction was monitored by LC-MS of aliquots. Within 1 h, LC-MS analysis indicated the completion of the transglycosylation with conversion yield >95%; the product was purified using protein A chromatography to give 33 (920 μg as measured using Nanodrop). LC-MS: calculated for the whole antibody, M=147,224 Da; found (m/z), 147,224 (deconvolution data); after IdeS digestion, LC-MS calculated for the Fc part, M=24,813 Da; found (m/z), 24,814 (deconvolution data).

Synthesis of 34 (FIG. 36). A solution of commercial Herceptin (1.0 mg) and oxazoline 12 (143 μg, 20 equiv per reaction site) was incubated with wild-type Endo-S2 (1.0 μg) at 25° C. in 40 μL of 150 mM PBS buffer (pH=7.0), and the reaction was monitored by LC-MS of aliquots. Within 30 min, LC-MS analysis indicated the completion of the transglycosylation with conversion yield >95%; the product was purified using protein A chromatography to give 34 (900 μg as measured using Nanodrop). LC-MS: calculated for the whole antibody, M=146,909 Da; found (m/z), 146,912 (deconvolution data); after IdeS digestion, LC-MS calculated for the Fc part, M=24,656 Da; found (m/z), 24,656 (deconvolution data).

Synthesis of 35 (FIG. 36). A solution of commercial Herceptin (1.0 mg) and oxazoline 17 (230 μg, 20 equiv per reaction site) was incubated with wild-type Endo-S2 (10 μg) at 25° C. in 40 μL of 150 mM PBS buffer (pH=7.0), and the reaction was monitored by LC-MS of aliquots. After 2 h, LC-MS analysis indicated the completion of the transglycosylation with conversion yield >95%; the product was purified using protein A chromatography to give 35 (900 μg as measured using Nanodrop). LC-MS: calculated for the whole antibody, M=147,538 Da; found (m/z), 147,539 (deconvolution data); after IdeS digestion, LC-MS calculated for the Fc part, M=24,970 Da; found (m/z), 24,972 (deconvolution data).

Synthesis of 36 (FIG. 36). A solution of commercial Herceptin (1.0 mg) and oxazoline 30 (328 μg, 20 equiv per reaction site) was incubated with wild-type Endo-S2 (2.0 μg) at 25° C. in 40 μL of 150 mM PBS buffer (pH=7.0), and the reaction was monitored by LC-MS of aliquots. After 1 h, another portion of oxazoline (164 μg, 10 equiv per reaction site) was added, and the reaction was incubated for another 30 min. When LC-MS analysis indicated the completion of the trans-glycosylation with conversion yield >95%, the product was purified using protein A chromatography to give 36 (900 μg as measured using Nanodrop). LC-MS: calculated for the whole antibody, M=148,260 Da; found (m/z), 148,262 (deconvolution data); after IdeS digestion, LC-MS calculated for the Fc part, M=25,332 Da; found (m/z), 25,332 (deconvolution data).

Synthesis of 37 (FIG. 36. A solution of commercial Herceptin (1.0 mg) and oxazoline 31 (400 μg, 20 equiv per reaction site) was incubated with wild-type Endo-S2 (10 μg) at 25° C. in 40 μL of 150 mM PBS buffer (pH=7.0), and the reaction was monitored by LC-MS of aliquots. After 30 min, another portion of oxazoline (200 μg, 10 equiv per reaction site) was added, and the reaction was incubated for another 30 min. This procedure was repeated 2-3 times until LC-MS analysis indicated the conversion yield >90%, and the product was purified using protein A chromatography to give 37 (900 μg as measured using Nanodrop). LC-MS: calculated for the whole antibody, M=148,776 Da; found (m/z), 148,778 (deconvolution data); after IdeS digestion, LC-MS calculated for the Fc part, M=25,590 Da; found (m/z), 25,590 (deconvolution data).

Figure 38:
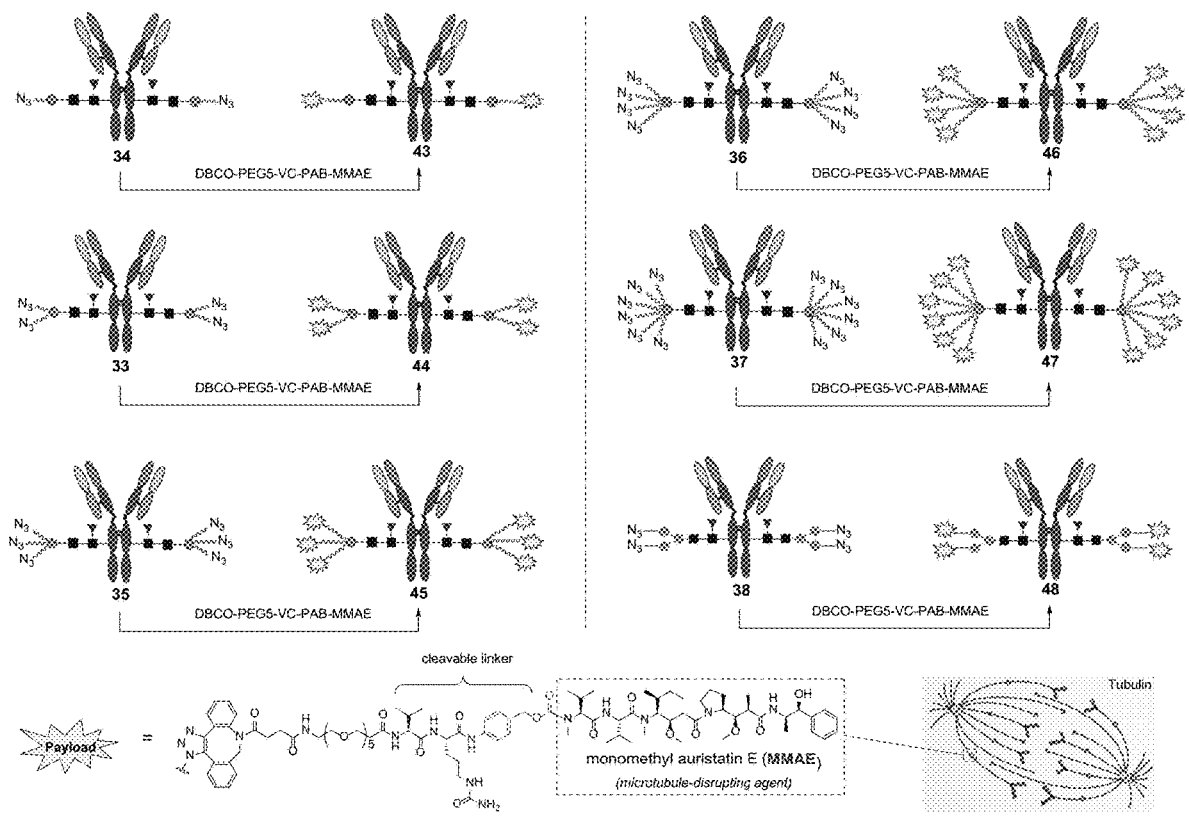
FIG. 38. Scheme 6. Synthesis of Structurally Defined ADCs with Different DARs by Click Chemistry. Reagents and conditions: the azido-tagged antibodies (final concentration 2 mg/mL) were incubated with DBCO-PEG5-VC-PAB-MMAE (3.3-5.0 equiv/per azido group) in DMSO/50 mM PB (3:7, v/v) at room temperature for 8-24 h.
Figure 39:
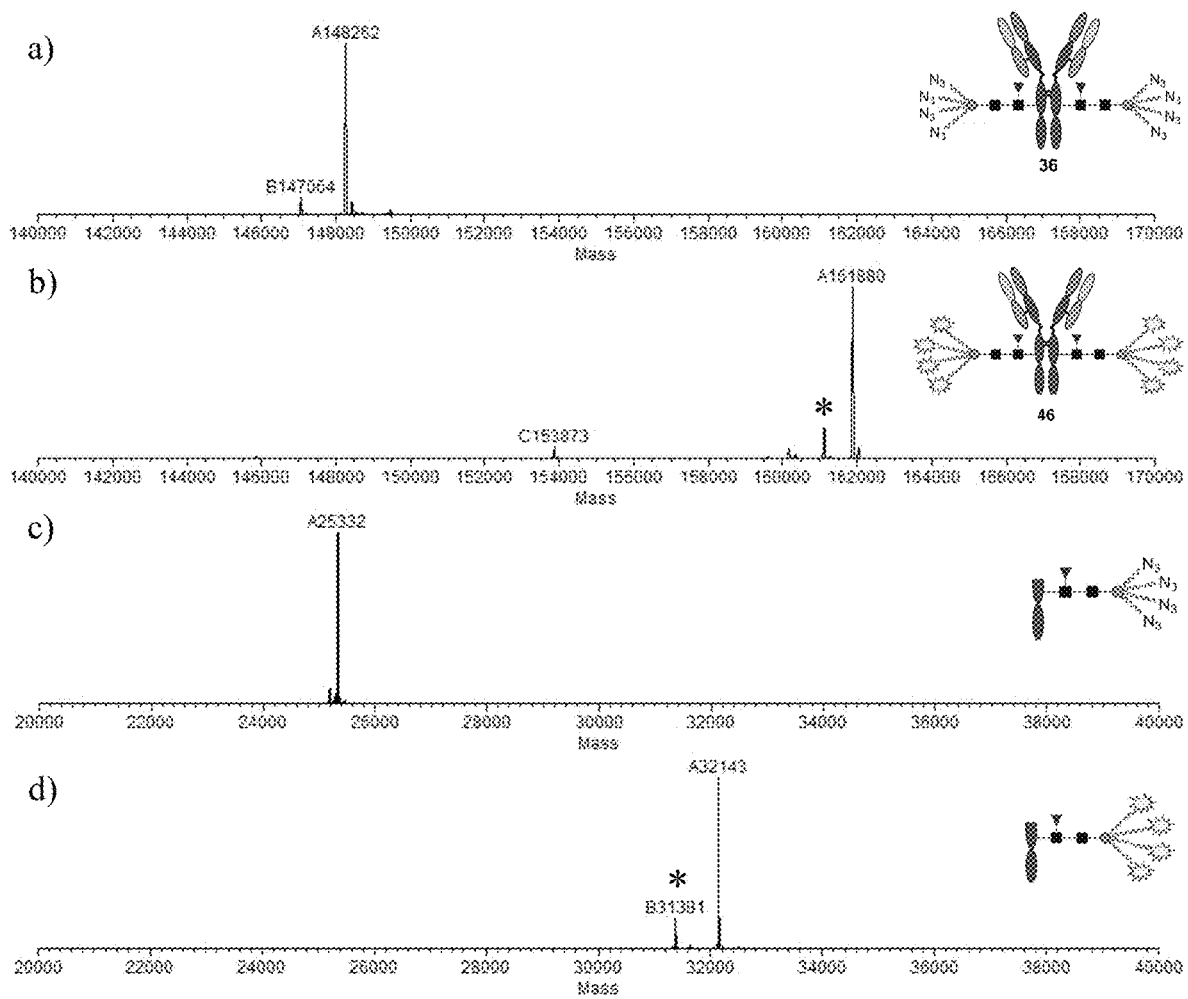
FIG. 39A-D. LC-ESI-MS analysis of ADC 46.

Synthesis of 38 (FIG. 38). A solution of deglycosylated Herceptin 32 (1.0 mg) and Man3GlcNAc tetrasaccharide oxazoline 35 (200 μg, 20 equiv per reaction site) was incubated with Endo-S2 D184M (10 μg) at 25° C. in 100 μL of 150 mM PBS buffer (pH=7.4), and the reaction was monitored by LC-MS of aliquots. Within 30 min, LC-MS analysis indicated the completion of the transglycosylation with conversion yield >95%, and the product was purified using protein A chromatography to give 38 (910 μg as measured using Nanodrop). LC-MS: calculated for the whole antibody, M=147,344 Da; found (m/z), 147,346 (deconvolution data); after IdeS digestion, LC-MS calculated for the Fc part, M=24,873 Da; found (m/z), 24,874 (deconvolution data).

Figure 37:
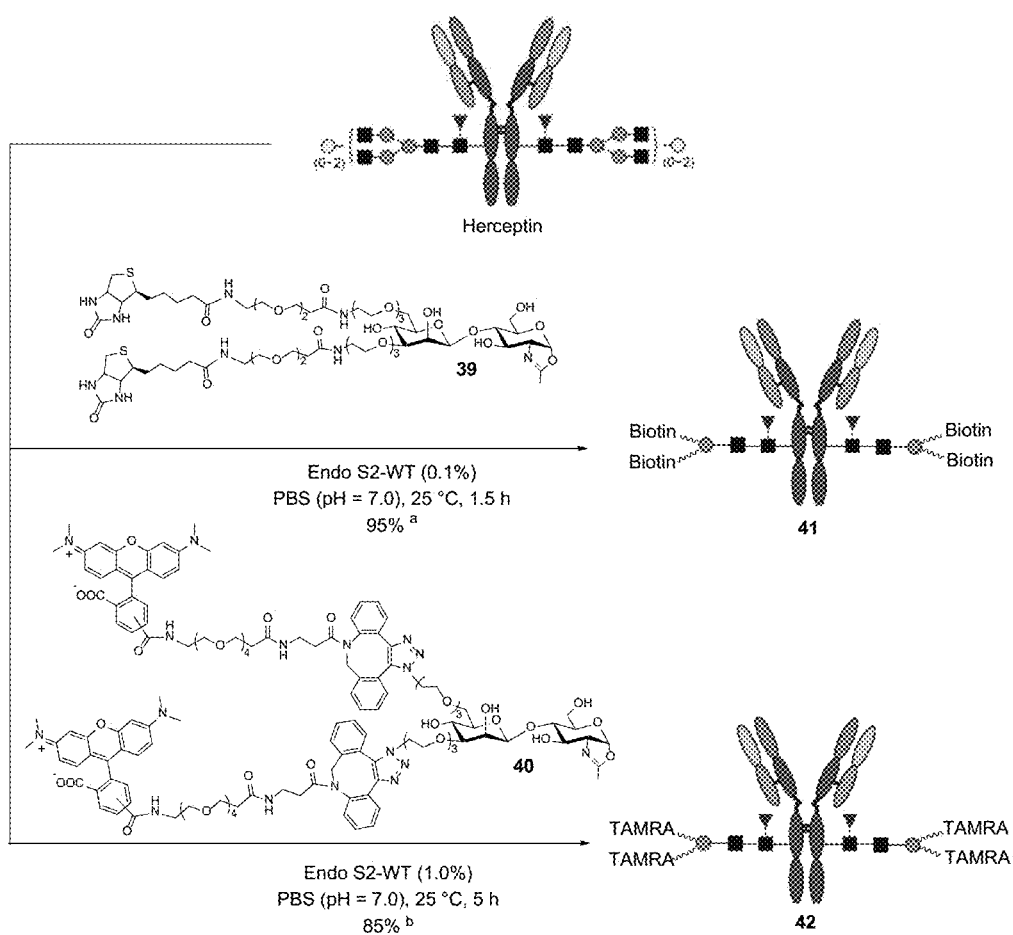
FIG. 37. Scheme 5. Reagents and conditions: the reactions were conducted with 20 equiv oxazolines in PBS buffer; (a) in the case of the biotin tag, one additional portion (10 equiv) of oxazoline 39 was added after 60 min; (b) in the case of the fluorescent tag, four more portions (10 equiv each) of oxazoline 40 were added every 60 min to push the reaction to completion.

Synthesis of 41 (FIG. 37). A solution of commercial Herceptin (100 pig) and Biotin-tagged oxazoline 39 (38.4 μg, 20 equiv per reaction site) was incubated with wild-type Endo-S2 (0.1 μg) at 25° C. in 5 μL of 150 mM PBS buffer (pH=7.0), and the reaction was monitored by LC-MS of aliquots. After 1 h, another portion of oxazoline (19.2 μg, 10 equiv per reaction site) was added, and the reaction was incubated for another 30 min. LC-MS analysis indicated the completion of the transglycosylation with conversion yield >95%. LC-MS: calculated for the whole antibody, M=148,660 Da; found (m/z), 148,663 (deconvolution data); after IdeS digestion, LC-MS calculated for the Fc part, M=25,532 Da; found (m/z), 25,533 (deconvolution data).

Synthesis of 42 (FIG. 37). A solution of commercial Herceptin (100 jig) and TAMRA-tagged oxazoline 40 (70 μg, 20 equiv per reaction site) was incubated with wild-type Endo-S2 (1.0 μg) at 25° C. in 5 μL of 150 mM PBS buffer (pH=7.0), and the reaction was monitored by LC-MS of aliquots. After 60 min, another portion of oxazoline (35 μg, 10 equiv per reaction site) was added, and the reaction was incubated for another 60 min. This procedure was repeated 4-5 times, and LC-MS analysis indicated that the conversion yield was ca. 85%. LC-MS: calculated for the whole antibody, M=150,968 Da; found (m/z), 150,967 (deconvolution data); after IdeS digestion, LC-MS calculated for the Fc part, M=26,687 Da; found (m/z), 26,685 (deconvolution data).

Synthesis of 43 (FIG. 38). To a solution of 34 (200 μg) in a mixture of 50 mM PB/DMSO (70 μL/25 μL) was added the drug payload (DBCO-PEG5-VC-PAB-MMAE)43 (5.0 mg/mL, 4.6 μL, 10 equiv), and the reaction was incubated at room temperature. After LC-MS analysis indicated the completion of the reaction, the mixture was diluted with 50 mM PB (3 mL) and filtered using a 0.22 μm filter to remove most of the hydrophobic payload, and the residue was purified using protein A chromatography to give 43 (150 μg as measured using Nanodrop). LC-MS: calculated for the whole antibody, M=150,313 Da; found (m/z), 150,314 (deconvolution data); after IdeS digestion, LC-MS calculated for the Fc part, M=26,358 Da; found (m/z), 26,359 (deconvolution data).

Synthesis of 44 (FIG. 38). To a solution of 33 (200 μg) in a mixture of 50 mM PB/DMSO (70 μL/20 μL) was added the drug payload (5.0 mg/mL, 9.2 μL, 20 equiv), and the reaction was incubated at room temperature. After LC-MS analysis indicated the completion of the reaction, the mixture was diluted with 50 mM PB (3 mL) and filtered using a 0.22 μm filter to remove most of the hydrophobic payload, and the residue was purified using protein A chromatography to give 44 (142 μg as measured using Nanodrop). LC-MS: calculated for the whole antibody, M=154,032 Da; found (m/z), 154,034 (deconvolution data); after IdeS digestion, LC-MS calculated for the Fc part, M=28,217 Da; found (m/z), 28,219 (deconvolution data).

Synthesis of 45 (FIG. 38). To a solution of 35 (200 μg) in a mixture of 50 mM PB/DMSO (70 μL/19 μL) was added the drug payload (5.0 mg/mL, 11.3 μL, 25 equiv), and the reaction was incubated at room temperature. After LC-MS analysis indicated the completion of the reaction, the mixture was diluted with 50 mM PB (3 mL) and filtered using a 0.22 µm filter to remove most of the hydrophobic payload, and the residue was purified using protein A chromatography to give 45 (120 µg as measured using Nanodrop). LC-MS: calculated for the whole antibody, M=157,750 Da; found (m/z), 157,753 (deconvolution data); after IdeS digestion, LC-MS calculated for the Fc part, M=30,076 Da; found (m/z), 30,079 (deconvolution data).

Synthesis of 46 (FIG. 38). To a solution of 36 (200 µg) in a mixture of 50 mM PB/DMSO (70 µL/15 µL) was added the drug payload (5.0 mg/mL, 13.6 µL, 30 equiv), and the reaction was incubated at room temperature. After LC-MS analysis indicated the completion of the reaction, the mixture was diluted with 50 mM PB (3 mL) and filtered using a 0.22 µm filter to remove most of the hydrophobic payload, and the residue was purified using protein A chromatography to give 46 (120 µg as measured using Nanodrop). LC-MS: calculated for the whole antibody, M=161,876 Da; found (m/z), 161,880 (deconvolution data); after IdeS digestion, LC-MS calculated for the Fc part, M=32,140 Da; found (m/z), 32,143 (deconvolution data).

Synthesis of 47 (FIG. 38). To a solution of 37 (200 µg) in a mixture of 50 mM PB/DMSO (70 µL/10 µL) was added the drug payload (5.0 mg/mL, 18.5 µL, 40 equiv), and the reaction was incubated at room temperature. After LC-MS analysis indicated the completion of the reaction, the mixture was diluted with 50 mM PB (3 mL) and filtered using a 0.22 m filter to remove most of the hydrophobic payload, and the residue was purified using protein A chromatography to give 47 (100 µg as measured using Nanodrop). LC-MS: calculated for the whole antibody, M=169,200 Da; found (m/z), 169,205 (deconvolution data); after IdeS digestion, LC-MS calculated for the Fc part, M=35,802 Da; found (m/z), 35,805 (deconvolution data).

Synthesis of 48 (FIG. 38). To a solution of 38 (200 µg) in a mixture of 50 mM PB/DMSO (70 µL/20 µL) was added the drug payload (5.0 mg/mL, 9.2 µL, 20 equiv), and the reaction was incubated at room temperature. After LC-MS analysis indicated the completion of the reaction, the mixture was diluted with 50 mM PB (3 mL) and filtered using a 0.22 µm filter to remove most of the hydrophobic payload, and the residue was purified using protein A chromatography to give 48 (130 µg as measured using Nanodrop). LC-MS: calculated for the whole antibody, M=154,151 Da; found (m/z), 154,154 (deconvolution data); after IdeS digestion, LC-MS calculated for the Fc part, M=28,277 Da; found (m/z), 28,279 (deconvolution data).

Cell Killing Studies with Breast Cancer Cell Lines. BT474 cells (ATCC HTB-20) were maintained in a suspension in Hybri-Care medium (ATCC 46-X) containing 10% fetal bovine serum (FBS), 100 U/mL penicillin, and 100 µg/mL streptomycin in T-75 flasks (CELLTREAT). T47D cells (ATCC HTB-133) were maintained in a suspension in RPMI-1640 medium (ATCC 30-2001) containing FBS, 4 mg/L insulin, 100 U/mL penicillin, and 100 µg/mL streptomycin in T-75 flasks (CELLTREAT). For the cytotoxicity assays, cells were plated into 96-well plates with 10,000 cells per well. These plates were incubated overnight at 37° C. and 5% $CO_2$. Serial threefold dilution was applied to the ADC samples with the corresponding medium from 5000 to 0.085 ng/mL. The samples were added to three wells (150 µL per well) with every single concentration, and the cells were cultured at 37° C. and 5% CO2 for three days before the addition of cell counting kit-8 (Sigma). The absorbance of formazan released by viable cells was measured at 450 nm using a spectrophotometer after incubation for 2-3 h at 37° C. and 5% $CO_2$. Finally, the EC50 values and the cell viability curve were calculated using GraphPad Prism software.

Example 4

Lysosome-targeting chimeras (LYTACs) offer an opportunity for the degradation of extracellular and membrane-associated proteins of interest. Described herein is an efficient chemoenzymatic method that enables a single-step and site-specific conjugation of high-affinity mannose-6-phosphate (M6P) glycan ligands to antibodies without the need of protein engineering and conventional click reactions that would introduce "unnatural" moieties, yielding homogeneous antibody-M6P glycan conjugates for targeted degradation of membrane-associated proteins. Using trastuzumab and cetuximab as model antibodies, it was shown that the wild-type endoglycosidase S (Endo-S) could efficiently perform the antibody deglycosylation and simultaneous transfer of a M6P-glycan from a synthetic M6P-glycan oxazoline to the deglycosylated antibody in a one-pot manner, giving structurally well-defined antibody-M6P glycan conjugates. A two-step procedure, using wild-type Endo-S2 for deglycosylation followed by transglycosylation with an Endo-S2 mutant (D184M), was also efficient to provide M6P glycan-antibody conjugates. The chemoenzymatic approach was highly specific for Fc glycan remodeling when both Fc and Fab domains were glycosylated, as exemplified by the selective Fc-glycan remodeling of cetuximab. SPR binding analysis indicated that the M6P-conjugates possessed a nanomolar range of binding affinities for the cation-independent mannose-6-phosphate receptor (CI-MPR). Preliminary cell-based assays showed that the M6P-trastuzumab and M6P-cetuximab conjugates were able to selectively degrade the membrane-associated HER2 and EGFR, respectively. This modular glycan-remodeling strategy is expected to find wide applications for antibody-based lysosome-targeted degradation of extracellular and membrane proteins.

Results

Screening of endoglycosidases for site-specific enzymatic transfer of phosphorylated glycans to antibodies. The phosphorylated tetrasaccharide oxazoline (1) corresponding to the α-1,3-branch of the N-glycans has recently been identified as a good substrate of wild-type Endo-A and Endo-F3 for transglycosylation to yield high-affinity ligands for CI-MPR (Zhang et al., Chem Sci 2021 12:12451-12462). To test if this M6P-glycan oxazoline can be efficiently transferred to an intact antibody by an enzyme, a panel of endoglycosidases were screened using the deglycosylated trastuzumab (Herceptin) as the acceptor and the phosphorylated tetrasaccharide oxazoline (1) as the donor substrate. The results were summarized in FIG. 43. Starting with wild-type Endo S that has been previously found to be active and specific for Fc deglycosylation of intact IgG antibodies and also for enzymatic transfer of truncated N-glycans (Haung et al., J Am Chem Soc. 2012 134:12308-18; Tong et al., Bioorg Med Chem 2018 26:1347-1355; Collin et al., EMBO J 2001 20:3046-55) with a catalytic amount of enzyme (0.2% w/w), it was found that Endo S-WT was quite efficient for transglycosylation, and the reaction went to completion within 2 h when a total of 30 mol. equiv. of the M6P tetrasaccharide oxazoline (1) was added in two portions. Only marginal (less than 1%) hydrolysis of the attached glycans was observed under this condition, which allowed for the accumulation of product. Considering the potent transglycosylation activity, together with its efficient hydrolysis of the complex-type N-glycans from the commercial antibody, wild-type Endo-S provides a practical one-pot strategy for remodeling of heterogeneous glycoforms of antibody to produce a homogeneous M6P-antibody conjugate, as the deglycosylation and transglycosylation could be performed in a one-pot manner without the need of isolating the wild-type enzyme and the deglycosylated antibody intermediate. Its mutant, Endo-S D233Q, was then tested which could efficiently transfer large biantennary glycan oxazolines to antibodies (Huang et al., J Am Chem Soc 2012 134:12308-18). It was found that the enzymatic reaction with the D233Q mutant was much slower than that of the wild type Endo-S, and it required larger amounts of enzyme and sugar oxazoline to drive the reaction to completion. Endo-S2, another endoglycosidase from the *Streptococcus pyogenes* of serotype M49 (Sjogren et al., Biochem J 2013 455:107-18) also exhibited rapid transglycosylation of the phosphorylated glycan (1) to the antibody when a catalytic amount of enzyme (0.1%, w/w) was used. But it was found that the wild-type Endo-S2 also hydrolyzed the glycan oxazoline (1) rapidly, although its hydrolysis of the resulting "ground-state" transglycosylation product was relatively slow. Thus, the wild type Endo-S2 was less efficient in this case than the Endo-S enzyme. To reduce the hydrolysis of glycan oxazoline substrate, the D184M mutant of Endo-S2, a glycosynthase with broad substrate specificity and diminished hydrolytic activity was tested. (Li et al., J Biol Chem 2016 291:16508-18). It was found that found that the D184M mutant exhibited excellent transglycosylation activity. With a catalytic amount of the enzyme (0.1%~0.2% w/w) and even reduced equivalents of the oxazoline (1) (10 equiv.), the reaction went on smoothly to afford the transglycosylation product within 1 h. As expected, no additional oxazoline was needed and the transglycosylation product was resistant to hydrolysis by the mutant. Thus, the Endo-S2 D184M mutant provided another practical method for production of M6P-containing antibodies. In addition to the Endo-S, Endo-S2, and their mutants, several other endoglycosidases were tested. Endo-F3, which prefers to hydrolyze core-fucosylated complex-type N-glycans (Giddens et al., J Biol Chem 2016 291:9356-9370) and has been successfully used for the M6P-glycan remodeling of a multiply glycosylated protein (Zhang et al., Chem Sci 2021 12:12451-12462) showed only a slow transglycosylation even if a large amount of enzyme (10%, w/w) was added. The Endo-F3 D165A mutant, a glycosynthase mutant that has been used for remodeling of both Fab and Fc glycans of a therapeutic antibody (Giddens et al., Proc Natl Acad Sci USA 2018 115:12023-12027) didn't show apparent activity toward this phosphorylated tetrasaccharide, as only trace amount of transglycosylation product was detected (FIG. 37). As for Endo-A, Endo-D and Endo-CC that prefer non-fucosylated substrates, the GNF-trastuzumab (2) was treated with a fucosidase (BfFucH) to produce an afucosylated Fc glycoform. However, all these three enzymes could not yield any product even if a large amount of the enzyme (10%, w/w) was used (FIG. 37). Taken together, the results suggest that the wild-type Endo-S and the glycosynthase mutant (D184M) of Endo-S2 are the best enzymes for antibody bioconjugation using the synthetic phosphorylated N-glycan oxazoline (1) as the donor substrate, and the wild-type Endo-S could perform simultaneous deglycosylation and glycosylation, allowing a one-pot bioconjugation with a M6P glycan ligand to produce a homogeneous antibody-M6P glycan conjugate.

Evaluation of additional M6P-glycan oxazolines as donor substrates for antibody glycan remodeling. After identifying the D184M mutant of Endo-S2 as an efficient mutant for glycosylation of trastuzumab with synthetic M6P-tetrasaccharide oxazoline (1), the glycosylation of the deglycosylated trastuzumab with two additional phosphorylated N-glycan oxazolines (4 and 5) that we have previously synthesized was examined and compared (Yamaguchi et al., J Am Chem Soc 2016 138:12472-85). As expected, the D184M mutant of Endo-S2 could efficiently act on glycan oxazoline 1 to produce the glycoform (3) carrying the corresponding M6P-containing N-glycan at the Fc domain (FIG. 28; Scheme 1). The D184M mutant could also use the larger bis-phosphorylated glycans (4 and 5) as donor substrates for transfer to give the two M6P antibody glycoforms (6 and 7), respectively, but a relatively large amount of enzyme and higher concentration of the antibody were required to drive the reaction to completion. These results indicate that the glycan oxazolines carrying two M6P moieties are not as good as the M6P tetrasaccharide oxazoline (1) as the donor substrate. Nevertheless, the data indicate that the Endo-S2 mutant can tolerate the modifications on the glycans to afford antibody glycoforms with different patterns of phosphorylation. The antibody products were purified on a protein A column and their identities were confirmed by LC-ESI-MS analysis. Finally, excess glycan oxazolines were recovered in the form of free oligosaccharides during purification, which were readily converted into the glycan oxazolines in a single step with DMC/Et$_3$N (Noguchi et al. J Org Chem 2009 74:2210-2212) thus permitting the recycling of glycan oxazolines for transglycosylation.

Figure 46:
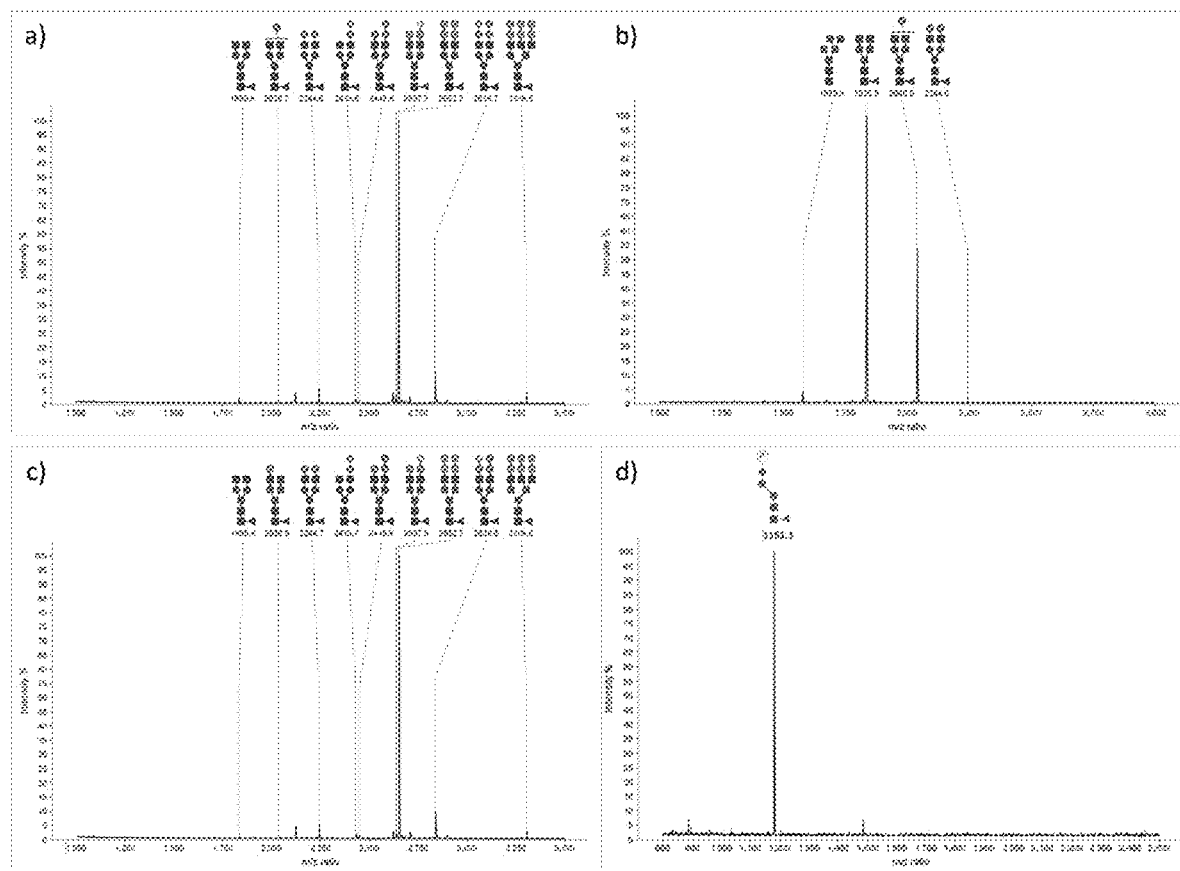
FIG. 46A-D. MALDI-TOF-MS analysis (positive-ion mode) of the Fc and Fab N-glycans of the commercial cetuximab and the glycoengineered cetuximab (9). The Fab and Fc domains were disconnected by IdeS treatment followed by protein L separation. The N-glycans were then released by PNGase F treatment, followed by permethylation before MALDI-TOF MS analysis, except for the M6P-containing glycan which resulted in loss of the phosphate group.

In addition to trastuzumab, M6P-glycan remodeling of cetuximab was also performed, a therapeutic antibody that targets the epidermal growth factor receptor (EGFR) for the treatment of colorectal cancer and squamous-cell carcinoma (Chung et al., N Engl J Med 2008 358:1109-1117). Cetuximab is glycosylated in both Fab and Fc domains with tremendous heterogeneity in the N-glycan structures (Qian et al., Anal Biochem 2007 364:8-18) Previous studies have shown that wild-type Endo-S2 is highly specific for hydrolyzing the Fc glycans. (Giddens et al., Proc Natl Acad Sci USA 2018 115:12023-12027). Thus, the commercial cetuximab was first treated with wild-type Endo-S2 to produce the deglycosylated Fc glycoform. Then the resulting GNF-cetuximab (8) was used as an acceptor for Endo-S2 D184M-catalyzed transglycosylation with glycan oxazoline 1 and 5, affording the M6P-glycan remodeled cetuximab 9 and 10, respectively. It was found that the M6P-glycan remodeling of cetuximab was equally efficient as that of trastuzumab, and the products (9 and 10) were isolated in over 90% yield after protein A purification. To further verify that the M6P glycans were specifically conjugated to the Fc domain, the antibody products (9 and 10) were digested with the protease IdeS followed by LC-ESI-MS analysis of the Fab and Fc domains (Chevreux et al., Anal Biochem 2011 415:22-4) LC-ESI-MS analysis showed that the change of molecular weight of the Fc domain monomer was consistent with the attachment of the corresponding M6P glycan in antibody 9 and 10, respectively, but the Fab domains appeared as a mixture of glycoforms that did not change before and after the enzymatic glycoengineering procedures. These results confirm that the chemoenzymatic glycan remodeling approach is highly selective at the Fc domain without modification of the Fab domains. In addition, MALDI-TOF MS analysis of the N-glycans released from the Fc and Fab domains of antibody 9 further confirmed that the Fc domain of 9 carried a single M6P glycan, while the Fab glycans were intact before and after the glycan remodeling (FIG. 46).

Figure 47:
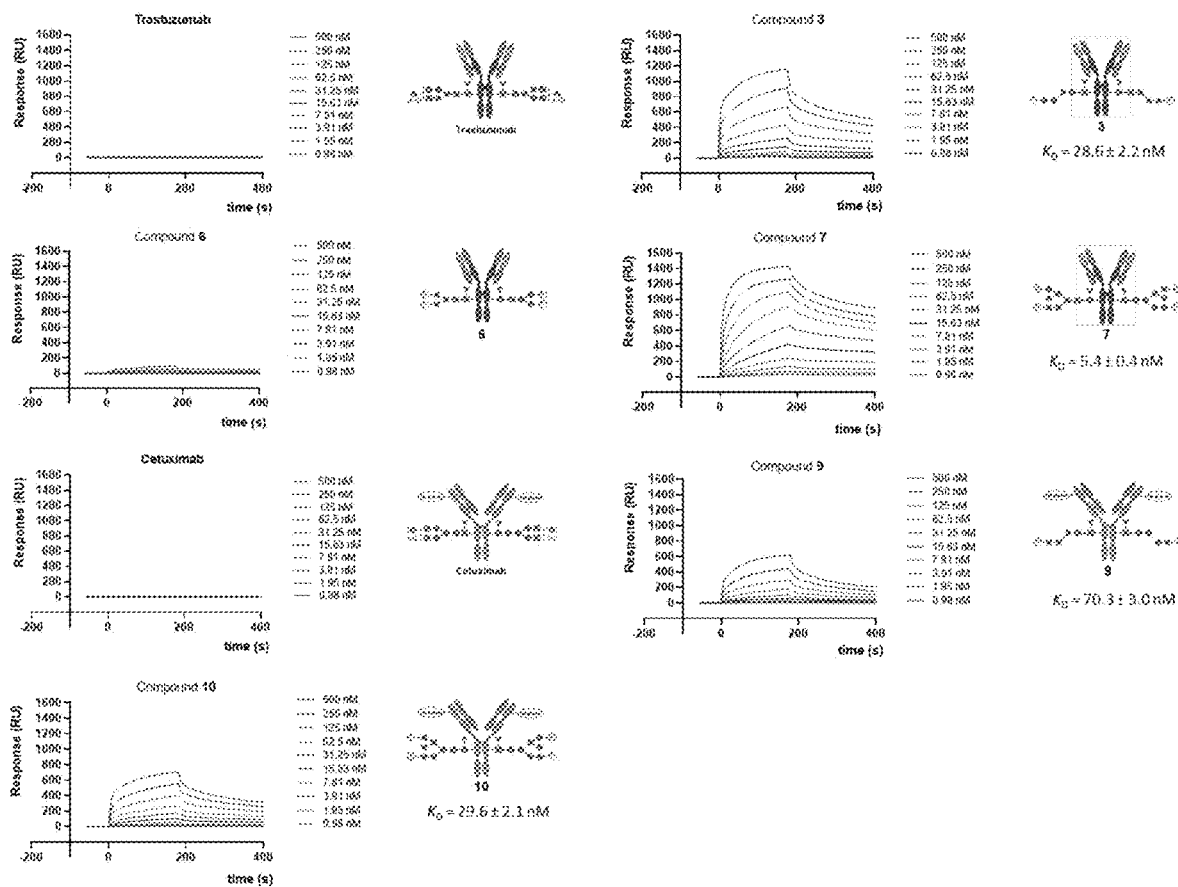
FIG. 47. SPR binding data of the CI-MPR with M6P-containing antibodies. The analytes were flowed over an immobilized chip with 2-fold serial dilution of the highest concentration of 500 nM. The sensorgrams are representative of two independent experiments.

SPR binding studies. Next, the binding affinities of the M6P-modified antibodies to the lysosomal-targeting receptor (CI-MPR) using the SPR technology was evaluated. It was found that the antibodies carrying the M6P tetrasaccharide moiety corresponding to the α-1,3-branch (3 and 9) and the bis-phosphorylated heptasaccharide moiety (7 and 10) showed high-affinity for the M6P receptor, CI-MPR (FIG. 47). In the case of trastuzumab, the $K_D$ values of binding were determined to be 28.6 nM and 5.4 nM for glycoforms 3 and 7, respectively. The data indicates that the affinity of the glycoform (7) carrying the bis-phosphorylated heptasaccharide moiety was about 4-fold higher than that of the glycoform (3) carrying the M6P tetrasaccharide moiety. On the other hand, the $K_D$ values for the two cetuximab glycoforms (9 and 10) were 70.3 nM and 29.6 nM, respectively. Thus, the affinity of the glycoform (10) carrying the large bis-phosphorylated N-glycan was about 2-fold as that of the one carrying the smaller M6P tetrasaccharide moiety (9). These data indicate that the nature of the antibody context also has a moderate effect on the affinity of the attached M6P glycan for the M6P receptor (CI-MPR). Interestingly, the antibody glycoform carrying the M6P-Man$_3$GlcNAc$_2$ glycan (6) showed only weak affinity for CI-MPR under the SPR measurement conditions. While the global fitting using the Langmuir binding model did not give reliable kinetic data for glycoform 6, a steady-state fitting gave an estimated $K_D$ value of ca. 0.70 μM. This result is consistent with the previous observation on the affinity of different M6P glycan ligands for CI-MPR. (Zhang et al., Chem Sci 2021 12: 12451-12462). Previous structure-affinity relationship studies of the M6P-glycopeptides have shown that a Man6P-α1,2-Man disaccharide moiety constitutes an essential structural motif that retains strong binding affinity for the CI-MPR receptor. The glycopeptide carrying the M6P-Man$_3$GlcNAc glycan lacks this motif, and shows only weak binding to CI-MPR, with a $K_D$ of ca. 0.84 μM, the affinity of which is much lower than that of the glycopeptides carrying the glycan with a Man6P-α1,2-Man disaccharide moiety. (Zhang et al., Chem Sci 2021 12: 12451-12462). Thus, the minimal M6P-tetrasaccharide oxazoline (1) that carries the essential high-affinity Man6P-α1,2-Man motif and is much easier to synthesize than the larger bis-M6P glycan oxazoline (5), was identified as a suitable donor substrate for direct Fc glycan remodeling to construct antibody-M6P-glycan conjugates with high-affinity for CI-MPR.

Figure 48:
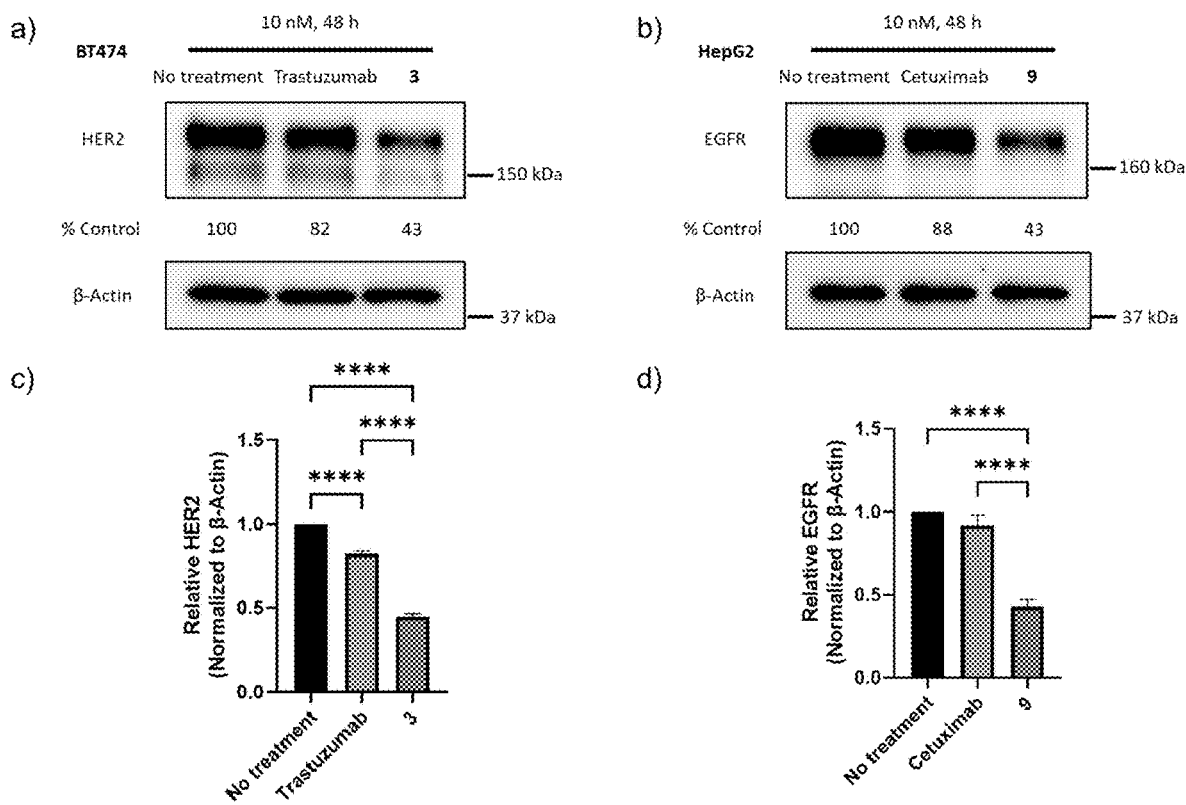
FIG. 48A-D. Western blot analysis of total HER2 and EGFR levels. Cells were treated with native or M6P-modified antibodies at a final concentration of 10 nM, then lysed in RIPA buffer after 48 h, set no-treatment cells as control. 48A Representative degradation of HER2 with trastuzumab or 3; 48B Representative degradation of EGFR with cetuximab or 9; 48C HER2 levels after treatment with trastuzumab or 3; 48D EGFR levels after treatment with cetuximab or 9. All assays were performed in triplicate.

Degradation of membrane-associated antigens with the M6P glycan-remodeled antibodies. Two antibodies were selected, the M6P-modified trastuzumab (3) that recognizes HER2 and the M6P-modified cetuximab (9) that targets EGFR, to examine their potential for targeted degradation of the respective antigens in a cell-based assay. Thus, BT474 (with endogenous HER2 expression) and HepG2 (with endogenous EGFR expression) cell lines were incubated with 3 and 9 for 48 h, respectively, and the total antigen levels were measured by Western blot. It was found that M6P-modified trastuzumab (3) could degrade 55% of HER2 with a concentration as low as 10 nM, while trastuzumab alone degraded HER2 at 18% (FIG. 48). Similar degradation of EGFR was observed (57%) by the M6P-modified cetuximab (9) (FIG. 48).

Figure 49:
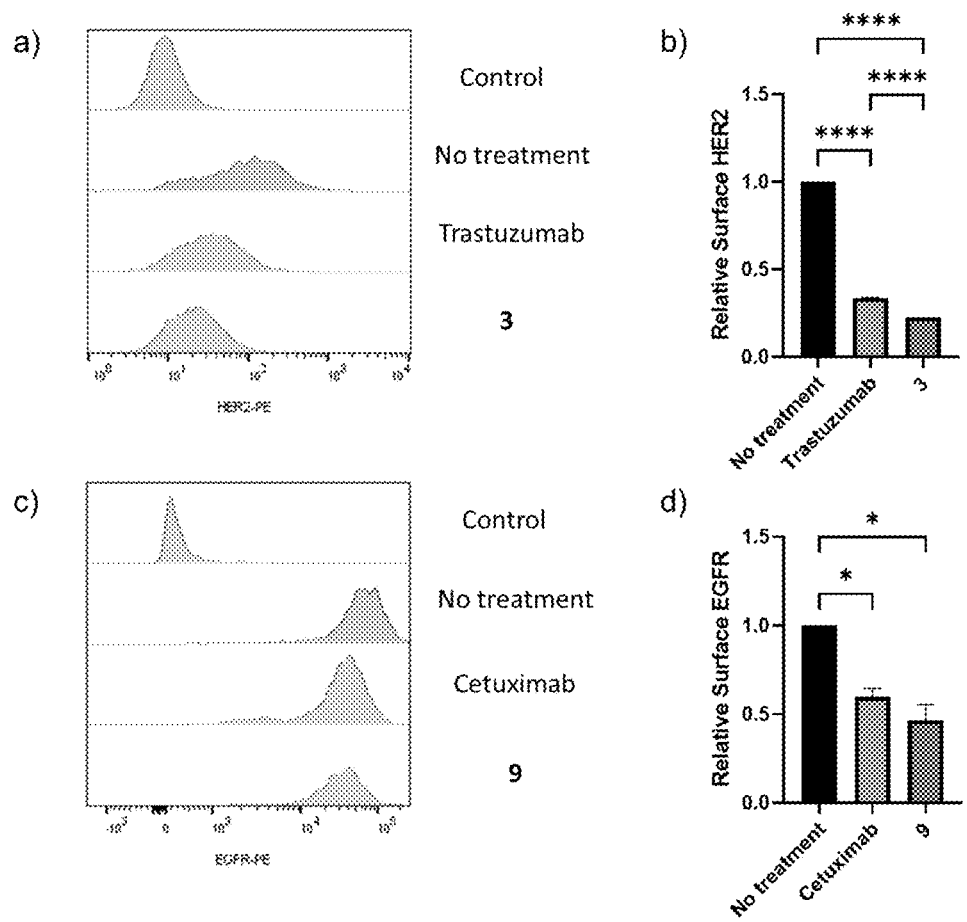
FIG. 49A-D. Degradation of cell surface HER2 or EGFR as determined by live-cell flow cytometry following 48 h of treatment with 10 nM native or M6P-modified antibodies.

The targeted degradation EGFR by the cetuximab-M6P glycan conjugate (9) produced in the present method was comparable to the cetuximab conjugate carrying the polymeric M6Pn-glycopeptide, where ca. 70% EGFR degradation was observed. (Banik et al., Nature 584:291-297). Next, the surface levels of HER2 and EGFR was measured by flow cytometry after the cells were treated with native or M6P-modified antibodies (FIG. 49). The results showed that both cetuximab and the M6P-modified cetuximab could efficiently internalize the cell surface EGFR, as demonstrated by the significant reduction of the EGFR binding signals (FIG. 49). However, the M6P-modified cetuximab showed much better effect than the unmodified cetuximab on reducing the total EGFR (FIG. 48). The data indicates that the M6P-modified antibodies could efficiently drive the antigens to lysosomes for degradation. The results confirm the feasibility of the structurally well-defined M6P glycan remodeled antibodies for degradation of member-associated proteins.

A highly efficient chemoenzymatic method for site-specific bioconjugation of high-affinity M6P glycan ligands to antibodies is established herein. The method provides structurally well-defined homogeneous M6P glycan-antibody conjugates that show high-affinity for the CI-MPR. The cell-based assays indicate that the M6P-trastuzumab and M6P-cetuximab conjugates can selectively degrade the membrane-associated HER2 and EGFR, respectively. This study provides the first example of endoglycosidase-catalyzed transfer of synthetic phosphorylated N-glycans to antibodies. This modular glycan-remodeling strategy enables the construction of homogeneous antibody-M6P-glycan conjugates in a single-step and site-specific manner without the need of protein engineering and conventional click reactions that would introduce "unnatural" moieties. It is expected that this method could be equally applicable to other antibodies to generate M6P-antibody conjugates for targeted degradation of extracellular and membrane proteins of interest.

Methods and Methods

Enzymatic glycosylation of the deglycosylated antibodies with phosphorylated glycan oxazolines as the donor substrates. General. LC-ESI-MS analysis was performed on an Ultimate 3000 HPLC system coupled to an Exactive Plus Orbitrap mass spectrometer (Thermo Fisher Scientific) with C4 (whole antibody, gradient, 5-95% aq MeCN containing 0.1% FA for 6 min, 0.4 mL/min) or C8 (IdeS digestion, gradient, 25-35% aq MeCN containing 0.1% FA for 6 min, 0.4 mL/min) column. Deconvolution data was transformed by MagTran software.

Synthesis of trastuzumab M6P-glycoform 3. A solution of the deglycosylated trastuzumab (2) (2.1 mg) and oxazoline 1 (220 μg, 10 eq per reaction site) was incubated with Endo S2-D184M (2.1 μg) at 25° C. in 210 μL of 150 mM PBS buffer (pH=7.2), and the reaction was monitored by LC-ESI-MS of the aliquots. Within 2 h, LC-ESI-MS analysis indicated the completion of the transglycosylation, the product was purified using protein A chromatography to give 3 (2.0 mg, 95%). ESI-MS: calculated for whole antibody, M=147403 Da; found (m/z), 147406 (deconvolution data); calculated for the Fc monomer after IdeS digestion, M=24903 Da; found (m/z), 24904 (deconvolution data).

Synthesis of trastuzumab M6P-glycoform 6. A solution of the deglycosylated trastuzumab (2) (300 μg) and oxazoline 4 (70 μg, 20 eq per reaction site) was incubated with Endo S2-D184M (15 μg) at 25° C. in 15 μL of 150 mM PBS buffer (pH=7.2), and the reaction was monitored by LC-ESI-MS of the aliquots. After 1 h, another portion of oxazoline 4 (35 μg, 10 eq per reaction site) was added and the reaction was carried out for another 30 min when LC-ESI-MS indicated the completion of transglycosylation. The product was purified on protein A column to give 6 (285 μg, 95%). ESI-MS: calculated for whole antibody, M=147563 Da; found (m/z), 147564 (deconvolution data); calculated for the Fc monomer after IdeS digestion, M=24983 Da; found (m/z), 24984 (deconvolution data).

Synthesis of trastuzumab M6P-glycoform 7. A solution of the deglycosylated trastuzumab (2) (300 μg) and oxazoline 5 (110 μg, 20 eq per reaction site) was incubated with Endo S2-D184M (15 μg) at 25° C. in 15 μL of 150 mM PBS buffer (pH=7.2), and the reaction was monitored by LC-ESI-MS of the aliquots. After 1 h, another portion of oxazoline 5 (55 μg, 10 eq per reaction site) was added and the reaction was run for another 30 min when LC-ESI-MS indicated the completion of the transglycosylation reaction. The product was purified using protein A chromatography to give 7 (270 μg, 90%). ESI-MS: calculated for whole antibody, M=148535 Da; found (m/z), 148537 (deconvolution data); calculated for the Fc monomer after IdeS digestion, M=25470 Da; found (m/z), 25470 (deconvolution data).

Synthesis of cetuximab M6P-glycoform 9. A solution of the deglycosylated cetuximab (8) (2.1 mg) and the M6P tetrasaccharide oxazoline (1) (220 μg, 20 eq per reaction site) was incubated with Endo S2-D184M (3.0 μg) at 25° C. in 210 μL of 150 mM PBS buffer (pH=7.2), and the reaction was monitored by LC-ESI-MS of the aliquots. The reaction was complete after 2 h and the product was purified using protein A chromatography to give 9 (1.9 mg, 90%). ESI-MS, calculated for the Fc monomer after IdeS digestion, M=24903 Da; found (m/z), 24904 (deconvolution data).

Synthesis of cetuximab M6P-glycoform 10. A solution of the deglycosylated cetuximab (8) (300 μg) and the glycan oxazoline (5) (110 μg, 20 eq per reaction site) was incubated with Endo S2-D184M (15 μg) at 25° C. in 15 μL of 150 mM PBS buffer (pH=7.2), and the reaction was monitored by LC-ESI-MS of the aliquots. After 1 h, another portion of oxazoline 5 (55 μg, 10 eq per reaction site) was added and the mixture was incubated for another 30 min when LC-ESI-MS indicated the completion of the reaction. The product was purified using protein A chromatography to give 10 (270 μg, 90%). ESI-MS: calculated for the Fc monomer after IdeS digestion, M=25470 Da; found (m/z), 25470 (deconvolution data).

Surface Plasmon Resonance (SPR) Measurements. SPR experiments were performed on a Biacore T200 instrument (GE Healthcare). Recombinant human IGF-II R (CI-MPR) was purchased from R&D Systems. Approximately 6000 resonance units (RU) of CI-MPR was immobilized on a CM5 sensor chip in a sodium acetate buffer (25 μg/mL, pH 4.0) at 25° C., using the amine coupling kit provided by the manufacturer. M6P-modified antibodies were determined at 25° C. under a flow rate of 10 μL/min. HBS-P+ buffer (10 mM HEPES, 150 mM NaCl, 0.05% surfactant P20, pH 7.4) was used as sample buffer and running buffer. Association was measured for 3 min and dissociation for 10 min at the same flow rate (10 μL/min). The surface regeneration was performed by 2 M $MgCl_2$ at a flow rate of 10 μL/min for 60 s. Antibody analytes were flowed over an immobilized chip with 2-fold serial dilution of the highest concentration of 500 nM. Kinetic analyses were performed by global fitting of the binding data to a 1:1 Langmuir binding model using BIAcore T200 evaluation software.

Western blot. BT474 (ATCC® HTB-20™) or HepG2 (ATCC® HB-8065™) cells were treated with native or M6P-modified antibodies at a final concentration of 10 nM, whole-cell lysate in Laemmli sample buffer was subjected to SDS-PAGE and Western blotting. The primary antibodies used in this study were against EGFR (Cell signaling technology), HER2 (Cell signaling technology), and Beta-actin (Life technology). Horseradish peroxidase-conjugated anti-rabbit IgG was used in this study as the secondary antibody. The specific reactions were detected with chemiluminescence substrate, and the signal was recorded digitally using ChemiDoc MP Imaging System (Bio-Rad). Relative band intensity was calculated using ImageJ software (NIH).

Flow Cytometry. HER2 or EGFR expression on the target cell surface were examined by flow cytometry. BT474 or HepG2 cells were trypsinized, centrifuged for 5 min at 2000 rpm, then washed with PBS, cells were stained with PE conjugated anti-human CD340 (erbB2/HER2) antibody (BioLegend) or PE conjugated anti-human EGFR (BioLegend) or PE conjugated Isotype control antibody in PBS at 4 degree for 30 min. After staining, cells were washed with PBS, then fixed with 2.5% formalin, Flow cytometry was performed using FACSCanto II cell sorter (BD), data were analyzed using FlowJo software (BD).

The documents listed below and referenced herein are incorporated herein by reference in their entireties, except for any statements contradictory to the express disclosure herein, subject matter disclaimers or disavowals, and except to the extent that the incorporated material is inconsistent with the express disclosure herein, in which case the language in this disclosure controls. Incorporation by reference of the following shall not be considered an admission by the applicant that the incorporated materials are prior art to the present disclosure, nor shall any document be considered material to patentability of the present disclosure.

```
                    Sequence Listings

Amino acid sequences of:
Endo-S2 wild type (SEQ ID NO. 1)
Endo-S wild type (SEQ ID NO. 4)
Endo-F3 wild type (SEQ ID NO. 5)
Endo-S2 D184 and mutants (D184M
(SEQ ID NO. 10), D184E (SEQ ID NO. 8),
D184C (SEQ ID NO. 7), D184G (SEQ ID NO. 9),
D184A (SEQ ID NO. 6), D184N (SEQ ID NO. 11),
D184Q (SEQ ID NO. 12), D184S (SEQ ID NO. 13),
D184T (SEQ ID NO. 14))
Endo-S D233A (SEQ ID NO. 3), D233Q (SEQ ID NO.
2), D233 M (SEQ ID NO. 15) mutants
Endo-F3 D165A (SEQ ID NO. 16) mutant
Signal peptide is marked gray
            EndoS2 (37-819)

10         20         30         40
MDKHLLVKRT LGCVCAATLM GAALATHHDS LNTVKAEEKT 50         60         70         80
VQTGKTDQQV GAKLVQEIRE GKRGPLYAGY FRTWHDRAST
         90        100        110        120
GIDGKQQHPE NTMAEVPKEV DILFVFHDHT ASDSPFWSEL
        130        140        150        160
KDSYVHKLHQ QGTALVQTIG VNELNGRTGL SKDYPDTPEG
        170        180        190        200
NKALAAAIVK AFVTDRGVDG LDIDIEHEFT NKRTPEEDAR
        210        220        230        240
ALNVFKEIAQ LIGKNGSDKS KLLIMDTTLS VENNPIFKGI
        250        260        270        280
AEDLDYLLRQ YYGSQGGEAE NDTINSDWNQ YQNYIDASQF
        290        300        310        320
MIGFSFFEES ASKGNLWFDV NEYDPNNPEK GKDIEGTRAK
        330        340        350        360
KYAEWQPSTG GLKAGIFSYA IDRDGVAHVP STYKNRTSTN
        370        380        390        400
LQRHEVDNIS HTDYTVSRKL KTLMTEDKRY DVIDQKDIPD
```

Sequence Listings

Endo-S sequence: (37-995) (SEQ ID NO. 2) (continued)

```
         410         420         430         440
  PALREQIIQQ  VGQYKGDLER  YNKTLVLTGD  KIQNLKGLEK
         450         460         470         480
  LSKLQKLELR  QLSNVKEITP  ELLPESMKKD  AELVMVGMTG
         490         500         510         520
  LEKLNLSGLN  RQTLDGIDVN  SITHLTSFDI  SHNSLDLSEK
         530         540         550         560
  SEDRKLLMTL  MEQVSNHQKI  TVKNTAPENQ  KPGYYPQTY
         570         580         590         600
  DTKEGHYDVD  NAEHDILTDF  VFGTVTKRNT  FIGDEEAFAI
         610         620         630         640
  YKEGAVDGRQ  YVSKDYTYEA  FRKDYKGYKV  HLTASNLGET
         650         660         670         680
  VTSKVTATTD  ETYLVDVSDG  EKVVHHMKLN  IGSGAIMMEN
         690         700         710         720
  LAKGAKVIGT  SGDFEQAKKI  FDGEKSDRFF  TWGQTNWIAF
         730         740         750         760
  DLGEINLAKE  WRLFNAETNT  EIKTDSSLNV  AKGRLQILKD
         770         780         790         800
  TTIDLEKMDI  KNRKEYLSND  ENWTDVAQMD  DAKAIFNSKL
         810         820         830         840
  SNVLSRYWRF  CVDGG
```

Endo-S sequence: (37-995) (SEQ ID NO. 2)

```
          10          20          30          40
  MDKHLLVKRT  LGCVCAATLM  GAALATHHDS  LNTVKAEEKT
          50          60          70          80
  VQVQKGLPSI  DSLHYLSENS  KKEFKEELSK  AGQESQKVKE
          90         100         110         120
  ILAKAQQADK  QAQELAKMKI  PEKIPMKPLH  GPLYGGYFRT
         130         140         150         160
  WHDKTSDPTE  KKDKVNSMGEL PKEVDLAFIF  HDWTKDYSLF
         170         180         190         200
  WKELATKHVP  KLNKQGTRVI  RTIPWRFLAG  GDNSGIAEDT
         210         220         230         240
  SKYPNTPEGN  KALAKAIVDE  YVYKYNLDGL  DVDVEHDSIP
         250         260         270         280
  KVDKKEDTAG  VERSIQVFEE  IGKLIGPKGV  DKSRLFIMDS
         290         300         310         320
  TYMADKNPLI  ERGAPYINLL  LVQVYGSQGE  KGGWEPVSNR
         330         340         350         360
  PEKTMEERWQ  GYSKYIRPEQ  YMIGFSFYEE  NAQEGNLWYD
         370         380         390         400
  INSRKDEDKA  NGINTDITGT  RAERYARWQP  KTGGVKGGIF
         410         420         430         440
  SYAIDRGVA   HQPKKYAKQK  EFKDATDNIF  HSDYSVSKAL
         450         460         470         480
  KTVMLKDKSY  DLIDEKDFPD  KALREAVMAQ  VGTRKGDLER
         490         500         510         520
  TNGTLRLDNP  AIQSLEGLNK  FKKLAQLDLI  GLSRITKLDR
         530         540         550         560
  SVLPANMKPG  KDTLETVLET  YKKDNKEEPA  TIPPVSLKVS
         570         580         590         600
  GLTGLKELDL  SGFDRETLAG  LDAATLTSLE  KVDISGNKLD
         610         620         630         640
  LAPGTENRQI  FDTMLSTISN  HVGSNEQTVK  FDKQKPTGHY
         650         660         670         680
  PDTYGKTSLR  LPVANEKVDL  QSQLLFGTVT  NQGTLINSEA
         690         700         710         720
  DYKAYQNHKI  AGRSFVDSNY  HYNNFKVSYE  NYTVKVTDST
         730         740         750         760
  LGTTTDKTLA  TDKEETYKVD  FFSPADKTKA  VHTAKIVVGD
         770         780         790         800
  EKTMMVNLAE  GATVIGGSAD  PVNARKVFDG  QLGSETDNIS
         810         820         830         840
  LGWDSKQSII  FKLKEDGLIK  HWRFFNDSAR  NPETTNKPIQ
         850         860         870         880
  EASLQIFNIK  DYNLDNLLEN  PNKFDDEKYW  ITVDTYSQGG
         890         900         910         920
  ERATAFSNTL  NNITSKYWRV  VFDTKGDRYS  SPVVPELQIL
         930         940         950         960
  GYPLPNADTI  MKTVTTAKEL  SQQKDKFSQK  MLDELKIKEM
         970         980         990
  ALETSLNSKI  FDVTAINANA  GVLKDCIEKR  QLLKK
```

Endo-F3 sequence: (40-329) (SEQ ID NO. 5)

```
          10          20          30          40
  MKKIFFAQCS  ILLLMLGSCS  KMTEDMTPES  VNKEASVKSA
          50          60          70          80
  TALAGSNGVC  IAYYITDGRN  PTFKLKDIPD  KVDMVILFGL
          90         100         110         120
  KYWSLQDTTK  LPGGTGMMGS  FKSYKDLDTQ  IRSLQSRGIK
         130         140         150         160
  VLQNIDDDVS  WQSSKPGGFA  SAAAYGDAIK  SIVIDKWKLD
         170         180         190         200
  GISLDIEHSG  AKPNPIPTFP  GYAATGYNGW  YSGSMAATPA
         210         220         230         240
  FLNVISELTK  YFGTTAPNNK  QLQIASGIDV  YAWNKIMENF
         250         260         270         280
  RNNFNYIQLQ  SYGANVSRTQ  LMMNYATGTN  KIPASKMVFG
         290         300         310         320
  AYAEGGTNQA  NDVEVAKWTP  TQGAKGGMMI  YTYNSNVSYA
  NAVRDAVKN
```

EndoS2 Mutant sequences (SEQ ID NO. 6):
D184A (X = A); D184C (X = C); D184E (X = E);
D184G (X = G); D184M (X = M); D184N (X = N);
D184Q (X = Q) D184S (X = S); D184T (X = T)

```
          10          20          30          40
  MDKHLLVKRT  LGCVCAATLM  GAALATHHDS  LNTVKAEEKT
          50          60          70          80
  VQTGKTDQQV  GAKLVQEIRE  GKRGPLYAGY  FRTWHDRAST
          90         100         110         120
  GIDGKQQHPE  NTMAEVPKEV  DILFVFHDT   ASDSPFWSEL
         130         140         150         160
  KDSYVHKLHQ  QGTALVQTIG  VNELNGRTGL  SKDYPDTPEG
         170         180         190         200
  NKALAAAIVK  AFVTDRGVDG  LDIXIEHEFT  NKRTPEEDAR
         210         220         230         240
  ALNVPKEIAQ  LIGKNGSDKS  KLLIMDTTLS  VENNPIFKGI
         250         260         270         280
  AEDLDYLLRQ  YYGSQGGEAE  VDTINSDWNQ  VQNYIDASQF
         290         300         310         320
  MIGFSFFEES  ASKGNLWFDV  NEYDPNNPEK  GKDIEGTRAK
         330         340         350         360
  KYAEWQPSTG  GLKAGIFSYA  IDRDGVAHVP  STYKNRTSTN
         370         380         390         400
  LQRHEVDNIS  HTDYTVSRKL  KTLMTEDKRY  KVIDQKDIPD
         410         420         430         440
  PALREQIIQQ  VGQYKGDLER  YNKTLVLTGD  KIQNLKGLEK
         450         460         470         480
  LSKLQKLELR  QLSNVKEITP  ELLPESMKKD  AELVMVGMTG
         490         500         510         520
  LEKLNLSGLN  RQTLDGIDVN  SITHLTSFDI  SHNSLDLSEK
         530         540         550         560
  SEDRKLLMTL  MEQVSNHQKI  TVKNTAFENQ  KPGYYPQTY
         570         580         590         600
  DTKEGHYDVD  NAEHDILTDF  VFGTVTKRNT  FIGDEEAFAI
         610         620         630         640
  YKEGAVDGRQ  YVSKDYTYEA  FRKDYKGYKV  HLTASNLGET
         650         660         670         680
  VTSKVTATTD  ETYLVDVSDG  EKVVHHMKLN  IGSGAIMMEN
         690         700         710         720
  LAKGAKVIGT  SGDFEQAKKI  FDGEKSDRFF  TWGQTNWIAF
         730         740         750         760
  DLGEINLAKE  WRLFNAETNT  EIKTDSSLNV  AKGRLQILKD
         770         780         790         800
  TTIDLEKMDI  KNRKEYLSND  ENWTDVAQMD  DAKAIFNSKL
         810         820         830         840
  SNVLSRYWRD  CVDGGASSY
```

Endo-S Mutant sequence: D233A (X = A); D233Q (X = Q); D233M (X = M)

```
        10         20         30         40
MDKHLLVKRT LGCVCAATLM GAALATHHDS LNTVKAEEKT
        50         60         70         80
VQVQKGLPSI DSLHYLSENS KKEFKEELSK AGQESQKVKE
        90        100        110        120
ILAKAQQADK QAQELAKMKI PEKIPMKPLH GPLYGGYFRT
       130        140        150        160
WHDKTSDPTE KDKVNSMGEL PKEVDLAFIF HDWTKDYSLF
       170        180        190        200
WKELATKHVP KNLKQGTRVI RTIPWRFLAG GDNSGIAEDT
       210        220        230        240
SKYPNTPEGN KALAKAIVDE YVVKYNLDGL DVXVEHDSIP
       250        260        270        280
KVDKKEDTAG VERSIQVFEE IGKLIGPKGV DKSRLFIMDS
       290        300        310        320
TYMADKNPLI ERGAPYINLL LVQVYGSQGE KGGWEPVSNR
       330        340        350        360
PEKTMEERWQ GYSKYIRPEQ YMIGFSFYEE NAQEGNLWYD
       370        380        390        400
INSRKDEDKA NGINTDITGT RAERYARWQP KTGGVKGGIF
       410        420        430        440
SYAIDRDGVA HQPKKYAKQK EFKDATDNIF HSDYSVSKAL
       450        460        470        480
KTVMLKDKSY DLIDEKDFFD KALREAVMAQ VGTRKGDLER
       490        500        510        520
FNGTLRLDNP AIQSLEGLNK FKKLAQLDLI GLSRITKLDR
       530        540        550        560
SVLPANMKPG KDTLETVLET YKKDNKEEPA TIPPVSLKVS
       570        580        590        600
FLTGLKELDL SGFDRETLAG LDAATLTSLE KVDISGNKLD
       610        620        630        640
LAPGTENRQI FDTMLSTISN HVGSNEQTVK FDKQKPTGHY
       650        660        670        680
PDTYGKTSLR LPVANEKVDL QSQLLFGTVT NQGTLINSEA
       690        700        710        720
DYKAYQNHKI AGRSFVDSNY HYNNFKVSYE NYTVKVTDST
       730        740        750        760
LGTTTDKTLA TDKEETYKVD FFSPADKTKA VHTAKVIVGD
       770        780        790        800
EKTMMVNLAE GATVIGGSAD PVNARKVFDG QLGSETDNIS
       810        820        830        840
LGWDSKQSII FKLKEDGLIK HWRFFNDSAR NPETTNKPIQ
       850        860        870        880
EASLQIFNIK DYNLDNLLEN PNKFDDEKYW ITVDTYSAQG
       890        900        910        920
ERATAFSNTL NNITSKYWRV VFDTKGDRYS SPVVPELQIL
       930        940        950        96)
GYPLPNADTI MKTVTTAKEL SQQKDKFSQK MLDELKIKEM
       970        980        990
ALETSLNSKI FDVTAINANA GVLKDCIEKR    QLLKK
```

Endo-F3 mutant sequence: Endo-F3 D165A

```
        10         20         30         40
MKKIFFAQCS ILLLMLGSCS KMTEDMTPES VNKEASVKSA
        50         60         70         80
TALAGSNGVC IAYYITDGRN PTFKLKDIPD KVDMVILFGL
        90        100        110        120
KYWSLQDTTK LPGGTGMMGS FKSYKDLDTQ IRSLQSRGIK
       130        140        150        160
VLQNIDDDVS WQSSKPGGFA SAAAYGDAIK SIVIDKWKLD
       170        180        190        200
GISLAIEHSG AKPNPIPTFT GYAATGYNGW YSGSMAATPA
       210        220        230        240
FLNFISELTK YFGTTAPNNK QLQIASGIDV YAWNKIMENF
       250        260        270        280
RNNFNYIQLQ SYGANVSRTQ LMMNYATGTN KIPASKMVFG
       290        300        310        320
AYAEGGTNQA NDVEVAKWTP TQGAKGGMMI YTYNSNVSYA
NAVRDAVKN
```

What is claimed:

1. A one pot Fc glycan remodeling method that uses a single enzyme for both deglycosylation and transglycosylation, to provide a remodeled site-specifically functionalized antibody, the method comprising the steps of:
   (a) providing a single reactor, container, column, or pot;
   (b) introducing a single endoglycosidase having both deglycosylation and transglycosylation activity;
   (c) introducing an antibody for deglycosylation by the single endoglycosidase, thereby providing a deglycosylated intermediate that contains at least one N-acetylglucosamine (GlcNAc) or core-fucosylated N-acetylglucosamine (Fucα1,6GlcNAc) acceptor;
   (d) providing a modified glycan oxazoline comprising a disaccharide core; and
   (e) transglycosylating the modified glycan oxazoline to the N-acetylglucosamine (GlcNAc) or core-fucosylated N-acetylglucosamine (Fucα1,6GlcNAc) acceptor by the introduced single endoglycosidase of step (b), to provide a remodeled site-specifically functionalized antibody; wherein:
   said modified glycan oxazoline is a Group II Glcβ1,4GlcNAc based disaccharide oxazolines, comprising a glucose-β1,4-N-acetylglucosamine disaccharide core and the enzyme is Endo S (SEQ ID NO. 4), or Endo S2 (SEQ ID NO. 1).

2. The one pot Fc glycan remodeling method of claim 1, wherein the modified glycan oxazoline comprises a tag.

3. The one pot Fc glycan remodeling method of claim 2, wherein the tag is selected from the group consisting of a therapeutic agent, drug, ligand, azide, biotin, fluorescent probe, and diagnostic reagent.

4. The one pot Fc glycan remodeling method of claim 1, wherein the endoglycosidase comprises an affinity fusion peptide or protein.

5. The one pot Fc glycan remodeling method of claim 1, wherein the modified glycan oxazoline comprises oligoethylene spacers or polyethylene (PEG) linkers.

6. The one pot Fc glycan remodeling method of claim 1, wherein the modified glycan oxazoline comprises multiple molecular linkers attached to the disaccharide core to form a dendrimer.

7. The one pot Fc glycan remodeling method of claim 1, wherein the site-specifically functionalized antibody comprises alpha-Gal, rhamnose (Rha), tri-GalNAc moiety, or mannose-6-phosphate (M6P).

8. The one pot Fc glycan remodeling method of claim 3, wherein the remodeled site-specifically functionalized antibody is tagged with azide and is further modified with click conjugation to a therapeutic agent, drug, ligand, or diagnostic agent to provide an antibody-conjugate modified with a therapeutic agent, drug, ligand, or diagnostic agent.

9. A one pot Fc glycan remodeling method that uses a single enzyme for both deglycosylation and transglycosylation to provide a remodeled site-specifically functionalized antibody, the method comprising the steps of:
   (a) providing a single reactor, container, column, or pot;
   (b) introducing a single endoglycosidase having both deglycosylation and transglycosylation activity;
   (c) introducing an antibody for deglycosylation by the single endoglycosidase, thereby providing a deglycosylated intermediate that contains at least one N-acetylglucosamine (GlcNAc) or core-fucosylated N-acetylglucosamine (Fucα1,6GlcNAc) acceptor;
   (d) providing a modified glycan oxazoline comprising a disaccharide core; and
   (e) transglycosylating the modified glycan oxazoline to the N-acetylglucosamine (GlcNAc) or core-fucosylated N-acetylglucosamine (Fucα1,6GlcNAc) acceptor by the introduced single endoglycosidase of step (b), to provide a remodeled site-specifically functionalized antibody;
   wherein said modified glycan oxazoline is a Group I Manβ1,4GlcNAc based disaccharide oxazolines comprising a mannose-β1,4-N-acetylglucosamine disaccharide core and the enzyme is Endo S2 (SEQ ID NO. 1).

10. A one pot Fc glycan remodeling method that uses a single enzyme for both deglycosylation and transglycosylation to provide a remodeled site-specifically functionalized antibody, the method comprising the steps of:
   (a) providing a single reactor, container, column, or pot;
   (b) introducing a single endoglycosidase having both deglycosylation and transglycosylation activity;

(c) introducing an antibody for deglycosylation by the single endoglycosidase, thereby providing a deglycosylated intermediate that contains at least one N-acetylglucosamine (GlcNAc) or core-fucosylated N-acetylglucosamine (Fucα1,6GlcNAc) acceptor;
(d) providing a modified glycan oxazoline comprising a disaccharide core; and
(e) transglycosylating the modified glycan oxazoline to the N-acetylglucosamine (GlcNAc) or core-fucosylated N-acetylglucosamine (Fucα1,6GlcNAc) acceptor by the introduced single endoglycosidase of step (b), to provide a remodeled site-specifically functionalized antibody;
wherein said modified glycan oxazoline is a Group III Galβ1,4GlcNAc based disaccharide oxazolines, comprising a galactose-β1,4-N-acetylglucosamine disaccharide core wherein the enzyme is Endo S (SEQ ID NO. 4).

* * * * *